//  US010398769B2

United States Patent
Weiner et al.

(10) Patent No.: US 10,398,769 B2
(45) Date of Patent: Sep. 3, 2019

(54) INFLUENZA NUCLEIC ACID MOLECULES AND VACCINES MADE THEREFROM

(71) Applicants: The Trustees of the University of Pennsylvania, Philadelphia, PA (US); Inovio Pharmaceuticals, Inc., Plymouth Meeting, PA (US); David B. Weiner, Merion, PA (US); Jian Yan, Wallingford, PA (US)

(72) Inventors: David B. Weiner, Merion, PA (US); Jian Yan, Wallingford, PA (US)

(73) Assignees: THE TRUSTEES OF THE UNIVERSITY OF PENNSYLVANIA, Philadelphia, PA (US); INOVIO PHARMACEUTICALS, INC., Plymouth Meeting, PA (US)

( * ) Notice: Subject to any disclaimer, the term of this patent is extended or adjusted under 35 U.S.C. 154(b) by 397 days.

(21) Appl. No.: 14/910,136

(22) PCT Filed: Aug. 4, 2014

(86) PCT No.: PCT/US2014/049551
§ 371 (c)(1),
(2) Date: Feb. 4, 2016

(87) PCT Pub. No.: WO2015/023461
PCT Pub. Date: Feb. 19, 2015

(65) Prior Publication Data
US 2016/0175427 A1    Jun. 23, 2016

Related U.S. Application Data

(60) Provisional application No. 61/862,689, filed on Aug. 6, 2013.

(51) Int. Cl.
  A61K 39/145   (2006.01)
  A61K 39/12    (2006.01)
  C12N 7/00     (2006.01)
  C07K 14/005   (2006.01)
  A61K 39/00    (2006.01)

(52) U.S. Cl.
  CPC ........... *A61K 39/145* (2013.01); *A61K 39/12* (2013.01); *C07K 14/005* (2013.01); *C12N 7/00* (2013.01); *A61K 2039/53* (2013.01); *C12N 2760/16122* (2013.01); *C12N 2760/16134* (2013.01)

(58) Field of Classification Search
  None
  See application file for complete search history.

(56) References Cited

U.S. PATENT DOCUMENTS

| | | | | |
|---|---|---|---|---|
| 2011/0159031 A1* | 6/2011 | Falkner | ............... | A61K 39/145 424/199.1 |
| 2011/0182938 A1* | 7/2011 | Weiner | ............... | A61K 31/7088 424/209.1 |
| 2013/0052222 A1 | 2/2013 | Weiner et al. | | |

FOREIGN PATENT DOCUMENTS

| | | |
|---|---|---|
| WO | 2007100584 A2 | 9/2007 |
| WO | 2007122517 A2 | 11/2007 |
| WO | 2012052384 A1 | 4/2012 |

OTHER PUBLICATIONS

GenBank Accession # HQ244407, Influenza A virus (A/Anas crecca/Spain/1460/2008(H7N9)) segment 4 hemagglutinin (HA) gene, complete cds, 2010.*
GenBank Accession # ADN34738, hemagglutinin [Influenza A virus (A/Anas crecca/Spain/1460/2008(H7N9))], 2010.*
Gen Bank Accession # YP_009118475, hemagglutinin [Influenza A virus (A/Shanghai/02/2013 (H7N9))], 2015.*
Gen Bank Accession: AGR49435, hemagglutinin [Influenza A virus (A/chicken/Shanghai/S1076/2013(H7N9))], Jul. 2013.*
Gen Bank Accession: CY146972, Influenza A virus (A/chicken/Shanghai/S1076/2013(H7N9)) hemagglutinin (HA) gene, complete cds, Jul. 2013.*
Yan et al., "Highly Optimized DNA Vaccine Targeting Human Telomerase Reverse Transcriptase Stimulates Potent Antitumor Immunity", Cancer Immunol Res, 1(3): 179-189, 2013.
Chen et al., "Human infections with the emerging avian influenza A H7N9 virus from wet market poultry: clinical analysis and characterisation of viral genome", Lancet, 381: 1916-1925, 2013.

* cited by examiner

*Primary Examiner* — Benjamin P Blumel
(74) *Attorney, Agent, or Firm* — Riverside Law LLP

(57) ABSTRACT

Provided herein are nucleic acid sequences that encode novel consensus amino acid sequences of HA Influenza A of serotype H7N9 alone and in combination with HA hemagglutinin and/or influenza B hemagglutinin, as well as genetic constructs/vectors and vaccines expressing the sequences. Also provided herein are methods for generating an immune response against one or more influenza A serotypes and/or influenza B serotypes, or combinations thereof, using the vaccines that are provided.

26 Claims, 32 Drawing Sheets
Specification includes a Sequence Listing.

FIGURE 2
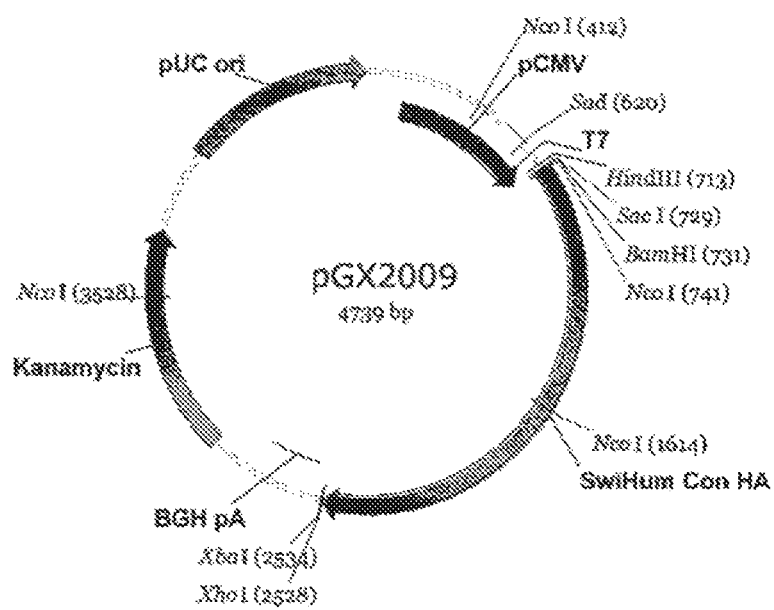
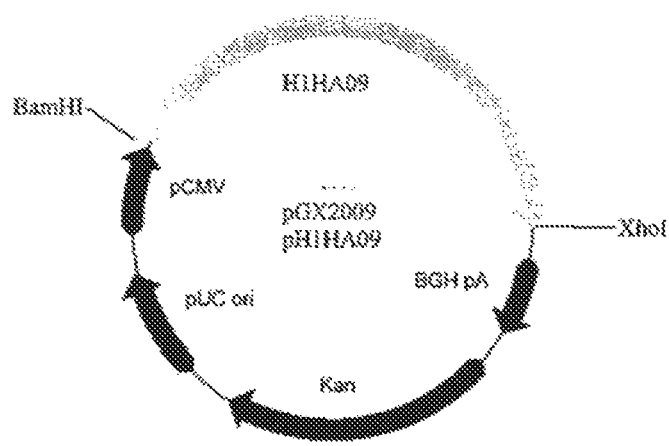

H1 tree of all viruses from last 20 years as well as South Carolina and where the constructs are located

FIGURE 6

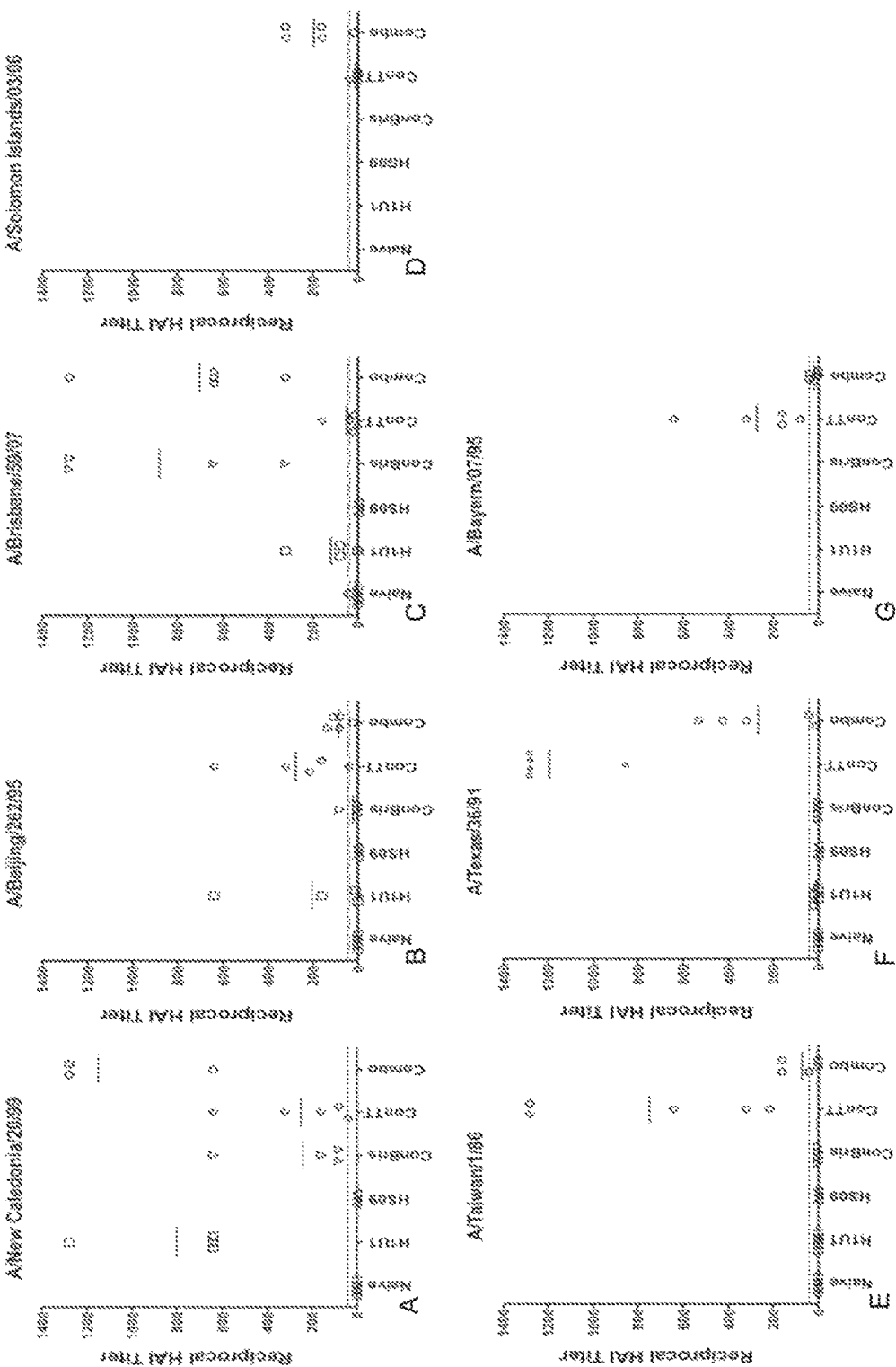
Mouse HAIs against seasonal viruses
FIGURES 7A-G

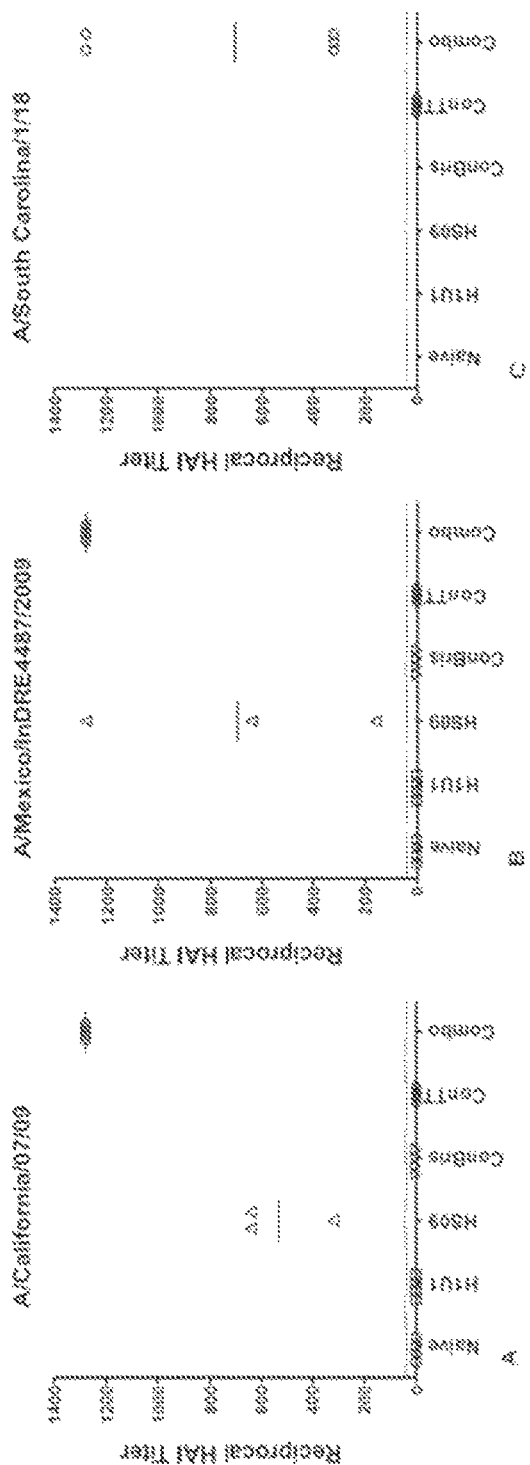
Mouse HAIs against pandemic viruses
FIGURES 8A-C

GUINEA PIGS COMBO VAX

GUINEA PIGS COMBO VAX

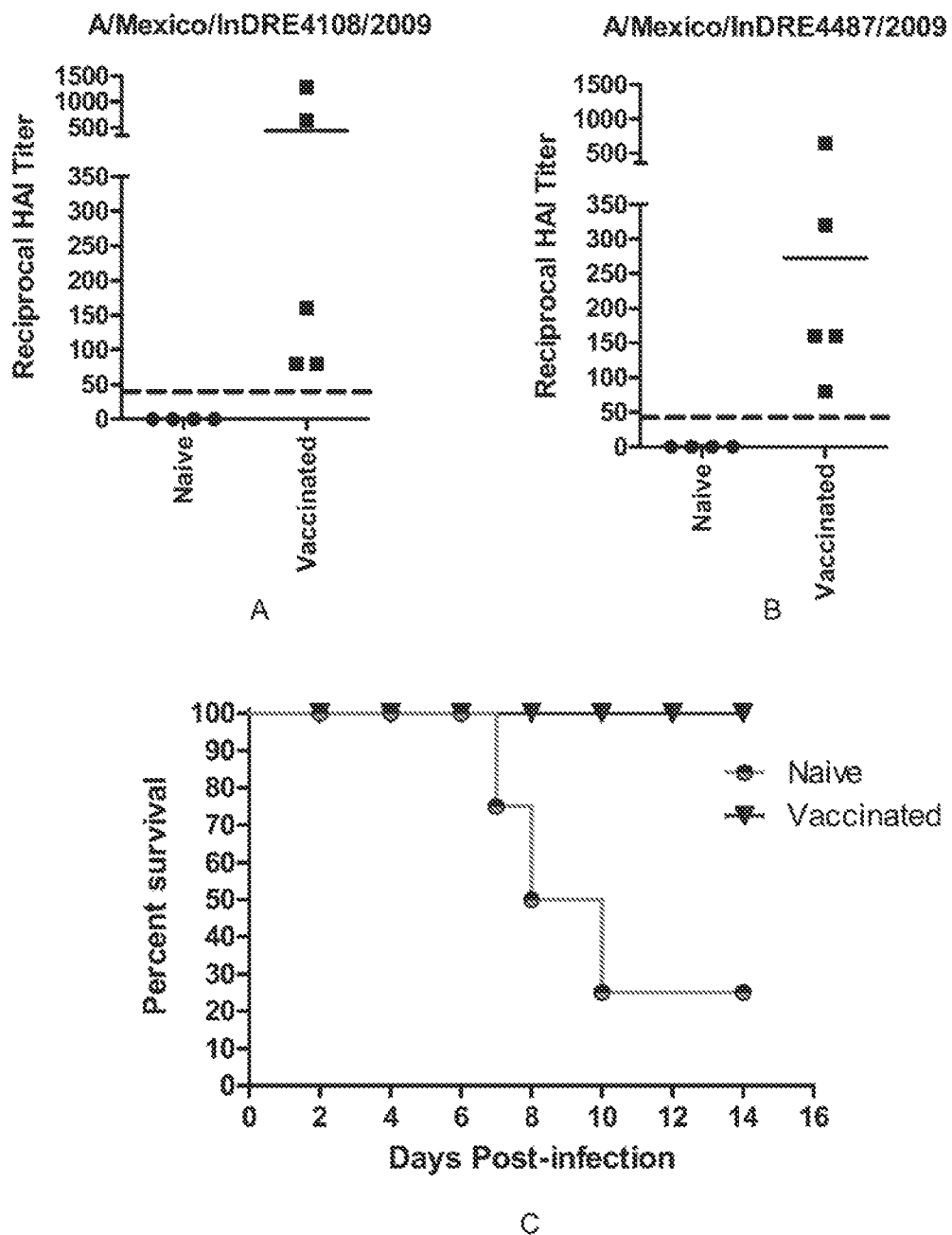
FERRETS VAX WITH HS09 & H1U, CHALLENGE STUDY
FIGURES 11A-C

FluB tree of all viruses from last 20 years and where the constructs are located

FIGURE 12

Mouse HAIs

FIGURES 13A-F

Mouse HAIs

FIGURES 14A-C

GUINEA PIG DATA

FIGURES 15A-D

GUINEA PIG DATA

FIGURES 16A-C

GUINEA PIG DATA

FIGURES 17A-C

Flu H3 tree of all viruses from last 20 years and where the constructs are located

Mouse HAIs

FIGURES 20A-F

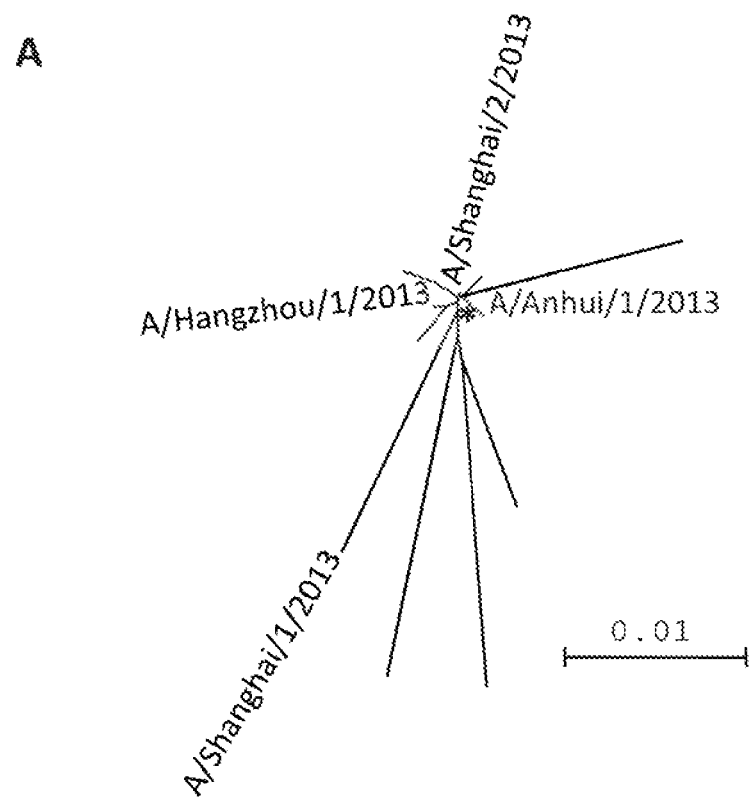
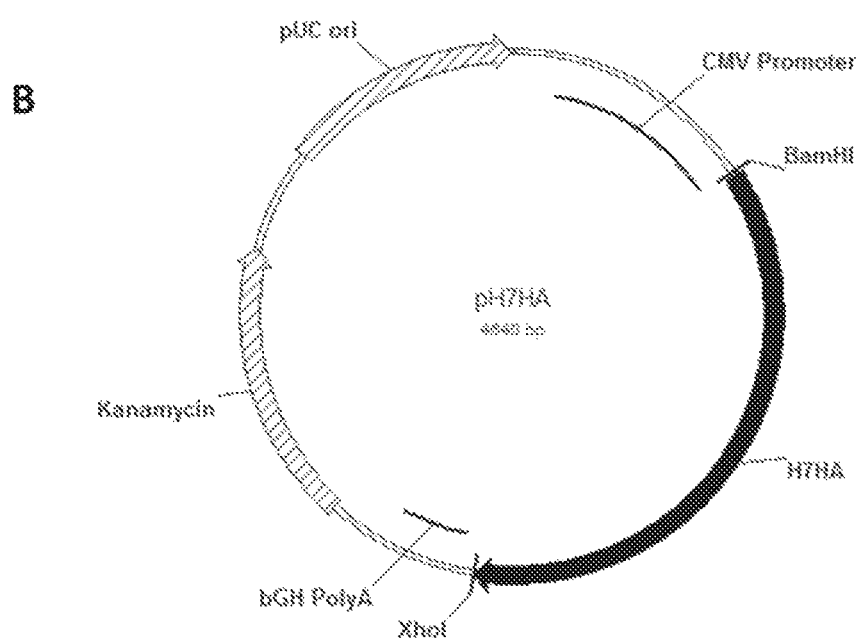
Figure 21

INFLUENZA NUCLEIC ACID MOLECULES AND VACCINES MADE THEREFROM

CROSS-REFERENCE TO RELATED APPLICATIONS

This application is the U.S. national stage application filed under 35 U.S.C. § 371 claiming benefit to International Patent Application No. PCT/US14/049551, filed Aug. 4, 2014, which is entitled to priority under 35 U.S.C. § 119(e) to U.S. Provisional Application No. 61/862,689, filed Aug. 6, 2013, each of which is hereby incorporated by reference in its entirety.

FIELD OF THE INVENTION

The present invention relates to improved H7N9 influenza viral vaccines, improved methods for inducing immune responses against influenza, improved methods for diagnosing vaccinated vs. infected influenza mammalian hosts and for prophylactically and/or therapeutically immunizing individuals against influenza.

BACKGROUND OF THE INVENTION

Influenza, commonly referred to as the flu, is an infectious disease caused by RNA viruses of the family Orthomyxoviridae. Influenza or flu viruses infect birds and mammals. Three of the five genera of Orthomyxoviridae are influenza viruses: Influenza A, Influenza B and Influenza C. Of these, Influenza A is the most common.

Influenza is typically transmitted through the air in aerosols produced by coughs or sneezes and by direct contact with body fluids containing the virus or contaminated surfaces. Seasonal epidemics of influenza occur worldwide and result in hundreds of thousands of deaths annually. In some years, pandemics occur and cause millions of deaths. In addition, livestock, particularly poultry and swine, are also susceptible to annual epidemics and occasional pandemics which cause large numbers of animal deaths and monetary losses. The newly emerged Chinese avian influenza A (H7N9) virus is one subgroup among the larger group of H7 viruses (10). As of Jul. 4, 2013, there have been a total of 133 laboratory-confirmed cases and 43 people have died, indicating a very high mortality rate (32.3%

Structurally, influenza viruses are similar, having generally spherical or filamentous virus particles of about 80-120 nm made up of similar molecular component. A central core comprising viral proteins and viral RNA is covered by a viral envelope made up of two different glycoproteins and a lipid coat derived from the cell that the viral particle is produced in. Two additional different glycoproteins are anchored within the viral envelope and include portions which project outward on the surface. The H7N9 virus exhibits several genetic features of mammalian influenza viruses, including the specificity of their HA protein binding to mammalian cellular receptors; a deletion in NA stalk associated with increased virulence in mammals; and an important mutation in the PB2 protein that is essential for the efficient replication of avian viruses in mammalian species. The efficient transmission of H7N9 virus in ferrets suggested that human-to-human transmission of this virus might be possible under appropriate conditions. As a result, the emergence of the novel H7N9 has raised concerns about its pandemic potential, as well as that of related influenza viruses.

New synthetic DNA vaccines have emerged as an attractive approach against various infectious diseases and cancers. Conceptually, DNA vaccines have many useful attributes over traditional vaccination strategies, such as live-attenuated vaccines, protein/peptide-based vaccines. While DNA vaccines have been shown to be capable of eliciting balanced CD4+ and CD8+ T cell responses as well as humoral immune responses in small-animal models, their progress in the clinic historically has been hampered by difficulties in generating sufficiently potent T cell and humoral responses in humans. Until recently, the DNA platform has been used primarily in prime-boost strategies along with viral vectors and proteins, thus creating an inordinately long testing and development window for addressing emerging pandemics rapidly. In order to address the technical hurdles associated with weak vaccine-induced immunity, we have recently applied many synthetic DNA design strategies, including codon/RNA optimization, the addition of highly efficient immunoglobulin leader sequences, use of 'centralized' immunogens to broaden immunity and remove dependence on any individual viral sequence, new formulations combined with highly efficient DNA delivery methods such as in vivo electroporation (EP), to improve the induction of immune responses induced by DNA vaccines in small animals, macaques, and most importantly, in humans.

Accordingly, there remains a need for an immunogenic influenza consensus hemagglutinin protein, for nucleic acid constructs that encode such a protein and for compositions useful to induce immune responses in mammals that are broadly cross reactive against multiple strains of influenza. There remains a need for effective vaccines against influenza that are economical and effective across numerous influenza subtypes for treating individuals, including ability to cross protect against multiple strains of influenza.

SUMMARY OF THE INVENTION

The present invention is directed to an isolated nucleic acid comprising a nucleic acid sequence encoding an amino acid sequence selected from the group consisting of SEQ ID NO: 40, an amino acid sequence that is 95% identical over the entire length of the amino acid sequence of SEQ ID NO: 40, a fragment of SEQ ID NO: 40 comprising at least 30 amino acids, and an amino acid sequence that is 95% identical to a fragment of SEQ ID NO: 40 comprising at least 30 amino acids. The isolated nucleic acid can comprise a nucleic acid sequence selected from the group consisting of SEQ ID NO: 39, a nucleic acid sequence that is 95% identical over the entire length of the nucleic acid sequence of SEQ ID NO: 39, a fragment of SEQ ID NO: 39 comprising at least 90 nucleotides, and a nucleic acid sequence that is 95% identical to a fragment of SEQ ID NO: 39 comprising at least 90 nucleotides. The isolated nucleic acid can comprise a nucleic acid sequence selected from the group consisting of a nucleic acid sequence that is 95% identical over the entire length of the nucleic acid sequence of SEQ ID NO: 39 and a nucleic acid sequence that is 95% identical to a fragment of SEQ ID NO: 39 comprising at least 90 nucleotides. A recombinant vector can comprise the isolated nucleic acid. An expression vector can comprise the isolated nucleic acid operably linked to regulatory elements. The regulatory elements can be functional in a human cell. The expression vector can be a plasmid. The expression vector can be pGX0001.

The present invention is directed to an isolated nucleic acid comprising a nucleic acid sequence encoding an amino acid sequence of SEQ ID NO: 40. The isolated nucleic acid can consist of a nucleic acid sequence encoding an amino acid sequence of SEQ ID NO: 40. The isolated nucleic acid can consist of a nucleic acid sequence of SEQ ID NO: 39. A recombinant vector can comprise the isolated nucleic acid. An expression vector can comprise the isolated nucleic acid operably linked to regulatory elements. The regulatory elements can be functional in a human cell. The expression vector can be a plasmid. The expression vector can be pGX0001.

The present invention is directed to a composition comprising: a first nucleic acid sequence comprising one or more nucleotide sequences encoding an amino acid sequence selected from the group consisting of SEQ ID NO: 40, an amino acid sequence that is 95% identical over the entire length of the amino acid sequence of SEQ ID NO: 40, a fragment of SEQ ID NO: 40 comprising at least 30 amino acids, and an amino acid sequence that is 95% identical to a fragment of SEQ ID NO: 40 comprising at least 30 amino acids; and a second nucleic acid sequence that encodes a protein selected from the group consisting of one or more of: H1, H2, H3, H4, H5, H6, H7, H8, H9, H10, H11, H12, H13, H14, H15, H16, N1, N2, N3, N4, N5, N6, N7, N8 and N9. The first nucleic acid sequence can be selected from the group consisting of one or more of SEQ ID NO: 39, a nucleic acid sequence that is 95% identical over the entire length of the nucleic acid sequence of SEQ ID NO: 39, a fragment of SEQ ID NO: 39 comprising at least 90 nucleotides, and a nucleic acid sequence that is 95% identical to a fragment of SEQ ID NO: 39 comprising at least 90 nucleotides. The first nucleic acid sequence can be operably linked to regulatory elements that are functional in a human cell. The composition can comprise a plasmid that comprises the first nucleic acid sequence operably linked to regulatory elements that are functional in a human cell. The second nucleic acid sequence can be selected from the group consisting of one or more of: SEQ ID NO: 1; a nucleic acid sequence that is 95% identical over the entire length of the nucleic acid sequence of SEQ ID NO: 1; a fragment of SEQ ID NO: 1 comprising at least 90 nucleotides; a nucleic acid sequence that is 95% identical to a fragment of SEQ ID NO: 1 comprising at least 90 nucleotides; SEQ ID NO: 3; a nucleic acid sequence that is 95% identical over the entire length of the nucleic acid sequence of SEQ ID NO: 3; a fragment of SEQ ID NO: 3 comprising at least 90 nucleotides; a nucleic acid sequence that is 95% identical to a fragment of SEQ ID NO: 3 comprising at least 90 nucleotides; SEQ ID NO: 6; a nucleic acid sequence that is 95% identical over the entire length of the nucleic acid sequence of SEQ ID NO: 6; a fragment of SEQ ID NO: 6 comprising at least 90 nucleotides; a nucleic acid sequence that is 95% identical to a fragment of SEQ ID NO: 6 comprising at least 90 nucleotides; SEQ ID NO: 8; a nucleic acid sequence that is 95% identical over the entire length of the nucleic acid sequence of SEQ ID NO: 8; a fragment of SEQ ID NO: 8 comprising at least 90 nucleotides; and a nucleic acid sequence that is 95% identical to a fragment of SEQ ID NO: 8 comprising at least 90 nucleotides. The composition can further comprise a peptide encoded by the nucleic acid sequence of SEQ ID NO: 39. The composition can further comprise a peptide comprising an amino acid sequence of SEQ ID NO: 40.

The present invention is directed to a vaccine that can comprise said isolated nucleic acids, said recombinant vectors, said expression vector, or said compositions. The vaccine can further comprise a peptide encoded by the nucleic acid sequence of SEQ ID NO: 39. The vaccine can further comprise a peptide comprising an amino acid sequence of SEQ ID NO: 40.

The present invention is directed to a vaccine comprising a nucleic acid sequence encoding an amino acid sequence of SEQ ID NO: 40. The vaccine can further comprise a peptide encoded by the nucleic acid sequence of SEQ ID NO: 39. The vaccine can further comprise a peptide comprising an amino acid sequence of SEQ ID NO: 40.

The present invention is directed to a vaccine comprising a nucleic acid sequence of SEQ ID NO: 39. The vaccine can further comprise a peptide encoded by the nucleic acid sequence of SEQ ID NO: 39. The vaccine can further comprise a peptide comprising an amino acid sequence of SEQ ID NO: 40.

The present invention is directed to a vaccine against an influenza virus comprising a nucleic acid sequence encoding an amino acid sequence of SEQ ID NO: 40. The nucleic acid sequence can comprise a nucleic acid sequence of SEQ ID NO: 39. The influenza virus can be H7N9 influenza virus. The vaccine can further comprise a peptide encoded by the nucleic acid sequence of SEQ ID NO: 39. The vaccine can further comprise a peptide comprising an amino acid sequence of SEQ ID NO: 40.

The present invention is directed to a method of inducing an immune response comprising the step of: administering to an individual a nucleic acid molecule comprising said isolated nucleic acids. The method can further comprise administering to said individual a therapeutically effective amount of a peptide encoded by the nucleic acid sequence of SEQ ID NO: 39. The method can further comprise administering to said individual a therapeutically effective amount of a peptide comprising an amino acid sequence of SEQ ID NO: 40. The nucleic acid molecule can be a plasmid. The plasmid can be pGX0001. The nucleic acid molecule can be administered to said individual using electroporation The present invention is directed to a method of inducing an immune response comprising the step of: administering to an individual said compositions. The method can further comprise administering to said individual a therapeutically effective amount of a peptide encoded by the nucleic acid sequence of SEQ ID NO: 39. The method can further comprise administering to said individual a therapeutically effective amount of a peptide comprising an amino acid sequence of SEQ ID NO: 40. The nucleic acid molecule can be a plasmid. The plasmid can be pGX0001. The nucleic acid molecule can be administered to said individual using electroporation The present invention is directed to a method of protecting an individual against infection by an avian origin human influenza strain comprising the step of: administering to said individual a prophylactically effective amount of a nucleic acid molecule comprising said isolated nucleic acids; wherein the nucleic acid molecule is expressed in cells of said individual and an immune response against said protein is induced that is a protective immune response against avian origin human influenza. The method can further comprise administering to said individual a therapeutically effective amount of a peptide encoded by the nucleic acid sequence of SEQ ID NO: 39. The method can further comprise administering to said individual a therapeutically effective amount of a peptide comprising an amino acid sequence of SEQ ID NO: 40. The nucleic acid molecule can be a plasmid. The plasmid can be pGX0001. The nucleic acid molecule can be administered to said individual using electroporation The present invention is directed to a method of protecting an individual against infection by an avian origin human influenza strain comprising the step of: administering to said individual a prophylactically effective amount of said compositions; wherein the first nucleic acid sequence is expressed in cells of said individual and an immune response against said first protein is induced that is a protective immune response against avian origin human influenza, the one or more second nucleic acid sequences are expressed in cells of said individual and immune responses against said one or more second proteins are induced. The method can further comprise administering to said individual a therapeutically effective amount of a peptide encoded by the nucleic acid sequence of SEQ ID NO: 39. The method can further comprise administering to said individual a therapeutically effective amount of a peptide comprising an amino acid sequence of SEQ ID NO: 40. The nucleic acid molecule can be a plasmid. The plasmid can be pGX0001. The nucleic acid molecule can be administered to said individual using electroporation The present invention is directed to a method of treating an individual who has been infected by an avian origin human influenza strain comprising the step of: administering to said individual a therapeutically effective amount of said isolated nucleic acids. The method can further comprise administering to said individual a therapeutically effective amount of a peptide encoded by the nucleic acid sequence of SEQ ID NO: 39. The method can further comprise administering to said individual a therapeutically effective amount of a peptide comprising an amino acid sequence of SEQ ID NO: 40. The nucleic acid molecule can be a plasmid. The plasmid can be pGX0001. The nucleic acid molecule can be administered to said individual using electroporation The present invention is directed to a method of treating an individual who has been infected by an avian origin human influenza H7N9 strain comprising the step of: administering to said individual a therapeutically effective amount of said compositions; wherein the first nucleic acid sequence is expressed in cells of said individual and an immune response against said first protein is induced that is a therapeutic immune response against avian origin human influenza, the one or more second nucleic acid sequences are expressed in cells of said individual and immune responses against said one or more second proteins are induced. The method can further comprise administering to said individual a therapeutically effective amount of a peptide encoded by the nucleic acid sequence of SEQ ID NO: 39. The method can further comprise administering to said individual a therapeutically effective amount of a peptide comprising an amino acid sequence of SEQ ID NO: 40. The nucleic acid molecule can be a plasmid. The plasmid can be pGX0001. The nucleic acid molecule can be administered to said individual using electroporation.

In some aspects of the invention, methods are provided for treating an individual who has been infected by influenza. The methods comprise the step of: administering to said individual a therapeutically effective amount of such nucleic acid molecules and/or composition. In some embodiment, the immune response is broadly cross reactive against multiple strains of influenza.

Based upon the sequence of pVAX1 available from Invitrogen, the following mutations were found in the sequence of pVAX1 that was used as the backbone for pGX2009:
C>G 241 in CMV promoter
C>T 1942 backbone, downstream of the bovine growth hormone polyadenylation signal (bGHpolyA)
A>- 2876 backbone, downstream of the Kanamycin gene
C>T 3277 in pUC origin of replication (Ori) high copy number mutation (see Nucleic Acid Research 1985)
G>C 3753 in very end of pUC Ori upstream of RNASeH site
Base pairs 2, 3 and 4 are changed from ACT to CTG in backbone, upstream of CMV promoter.

FIG. 2 shows two maps of the plasmid pGX2009, which is also referred to as pH1HA09. The nucleic acid sequence of the plasmid pGX2009 (SEQ ID NO:5) includes the coding sequence for the consensus H1 protein construct (amino acid SEQ ID NO:4 encoded by SEQ ID NO:3) which includes the IgE leader (amino acid SEQ ID NO:17) linked to the N terminal of the consensus H1 amino acid sequence (amino acid SEQ ID NO:2 encoded by SEQ ID NO:1) which is linked at its C terminal to the HA Tag (SEQ ID NO:18). The consensus H1 protein (amino acid SEQ ID NO:4 encoded by SEQ ID NO:3) is labeled SwiHum Con HA and H1HA09.

Figure 3:
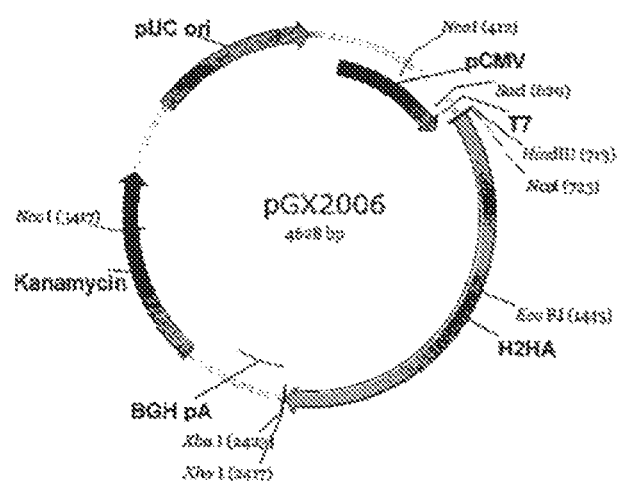

FIG. 3 shows a maps of the plasmid pGX2006. The nucleic acid sequence of the plasmid pGX2006 (SEQ ID NO:8) includes the coding sequence for consensus H2 protein (amino acid SEQ ID NO:7 encoded by SEQ ID NO:6) which is labeled H2HA.

Figure 4:
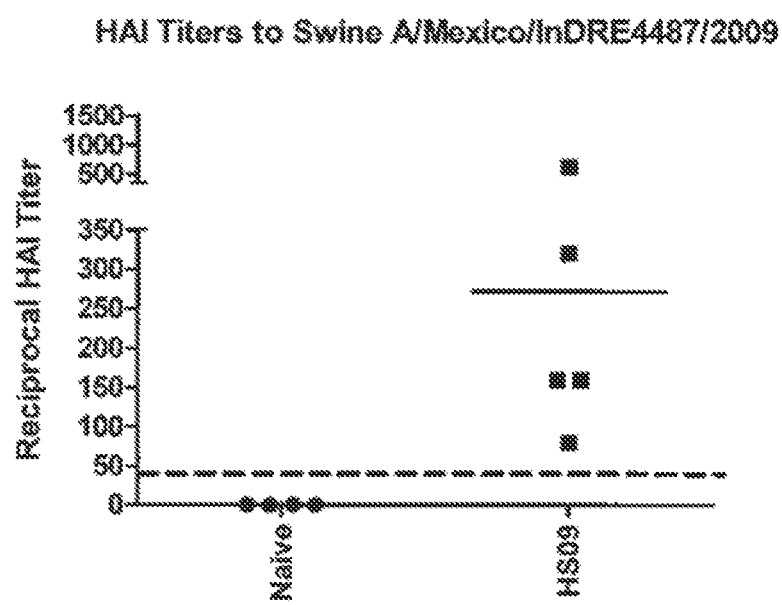

FIG. 4 shows data from hemagglutination inhibition assays performed with sera from immunized ferrets.

Figure 5:
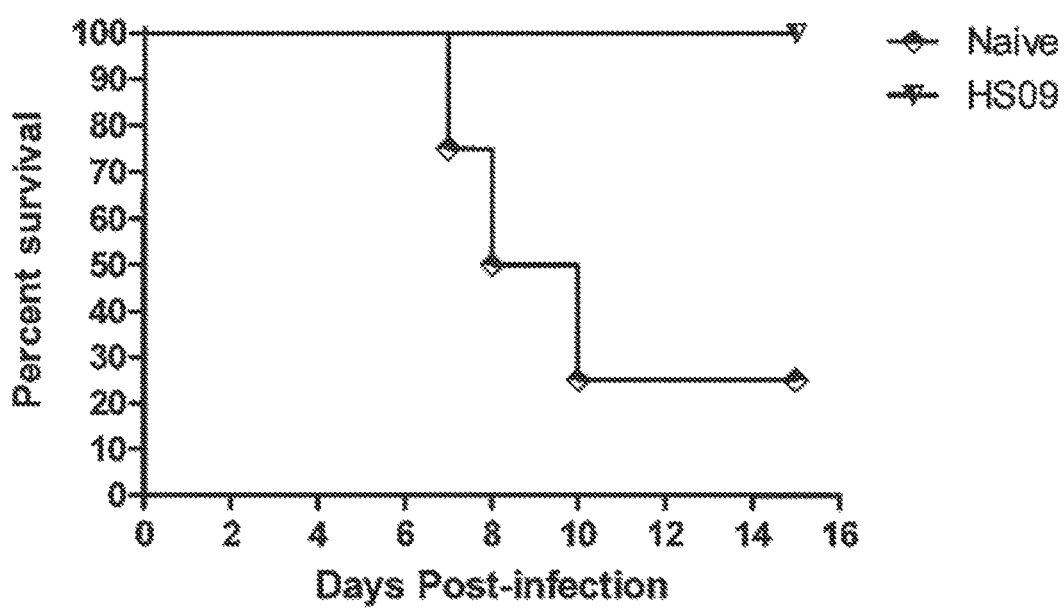

FIG. 5 shows results of a challenge of immunized and unimmunized ferrets with a novel H1N1 strain.

FIG. 6 displays an influenza H1 hemagglutinin (H1HA) genetic tree of the genes of strains over the last 20 years, showing the genetic relationship between the various H1HA influenza strains.

FIGS. 7A-G displays a number of graphs of inhibition titers generated from hemagglutination inhibition assays performed with sera from immunized mice (naïve, H1U (SEQ ID NO: 35), HS09 (SEQ ID NO:1), ConBris (or H1Bris; SEQ ID NO:19), ConTT (or H1-TT; SEQ ID NO:21), Combo (all 4 H1U, HS09, ConBris, and ConTT)) against various seasonal viruses.

FIGS. 8A-C displays a number of graphs of inhibition titers generated from hemagglutination inhibition assays performed with sera from immunized mice (naïve, H1U (SEQ ID NO: 35), HS09 (SEQ ID NO:1), ConBris (or H1Bris; SEQ ID NO:19), ConTT (or H1-TT; SEQ ID NO:21), Combo (all 4 H1U, HS09, ConBris, and ConTT)) against various pandemic viruses.

Figure 9A:
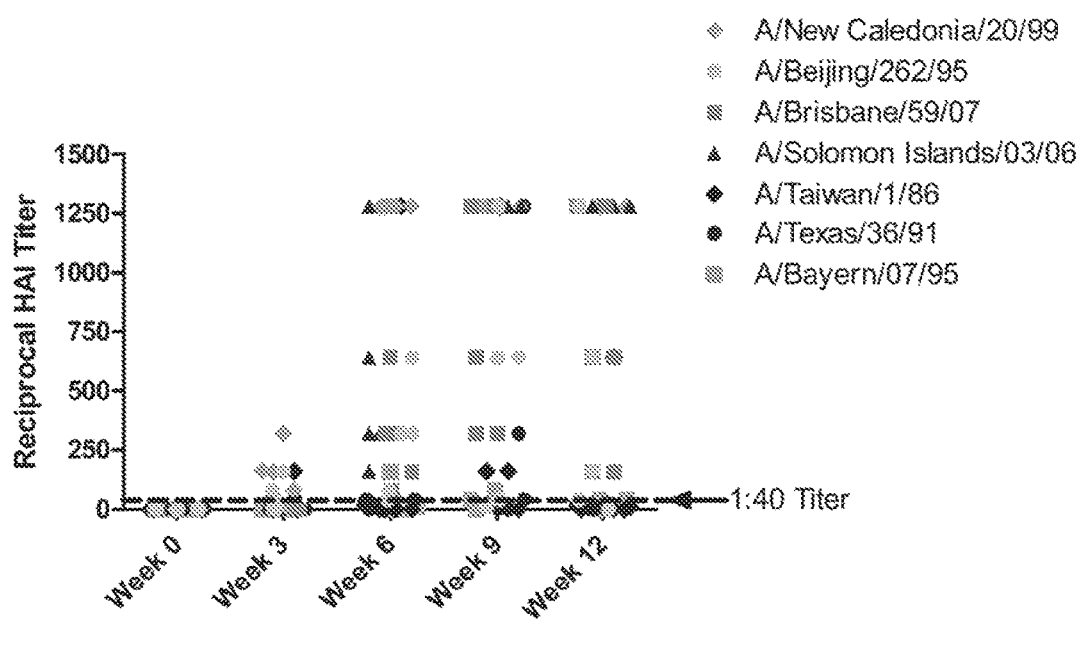
Figure 9B:
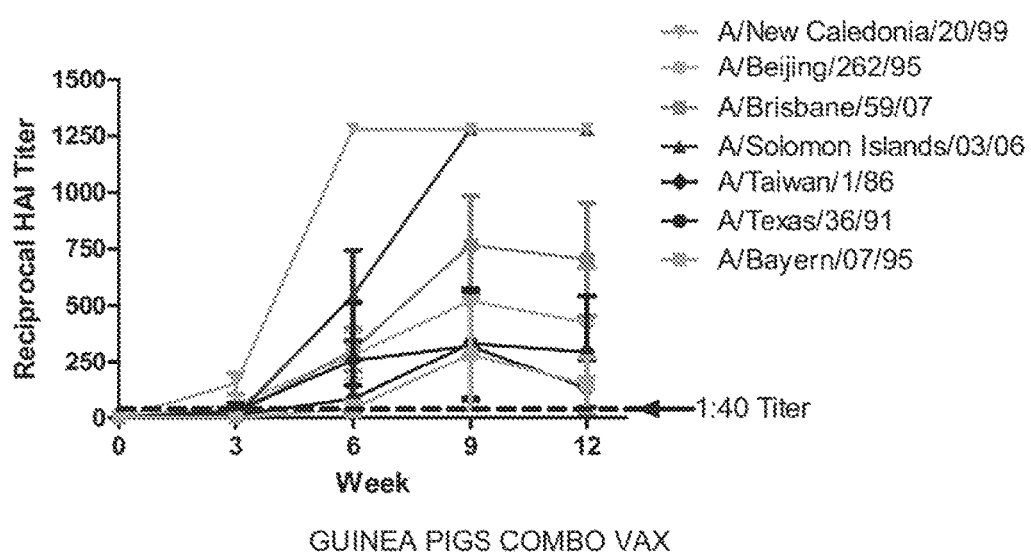

FIGS. 9A-B displays a number of graphs of inhibition titers generated from hemagglutination inhibition assays performed with sera from immunized guinea pigs (Combo (all 4 H1U, HS09, ConBris, and ConTT)) against various seasonal viruses; 9A showing the data points; and 9B showing the mean and standard deviation.

Figure 10A:
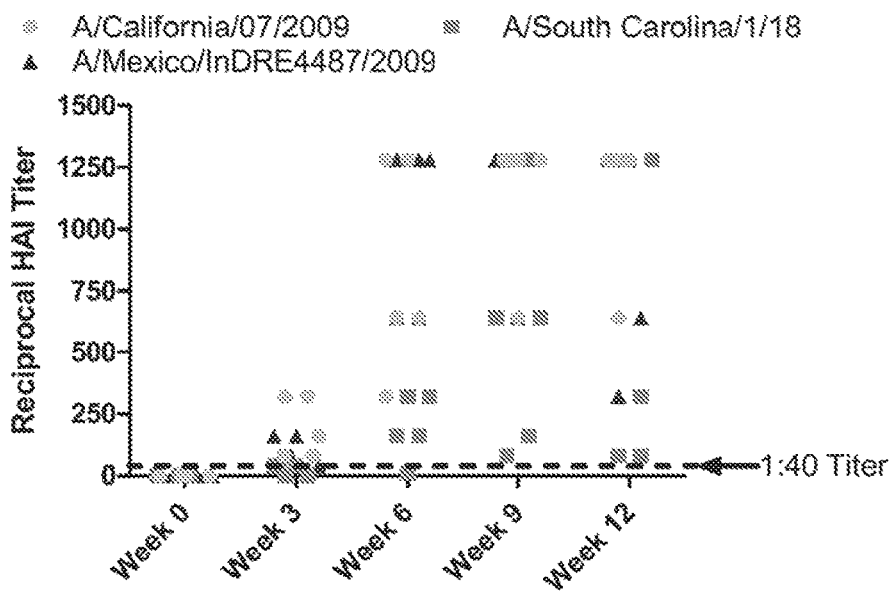
Figure 10B:
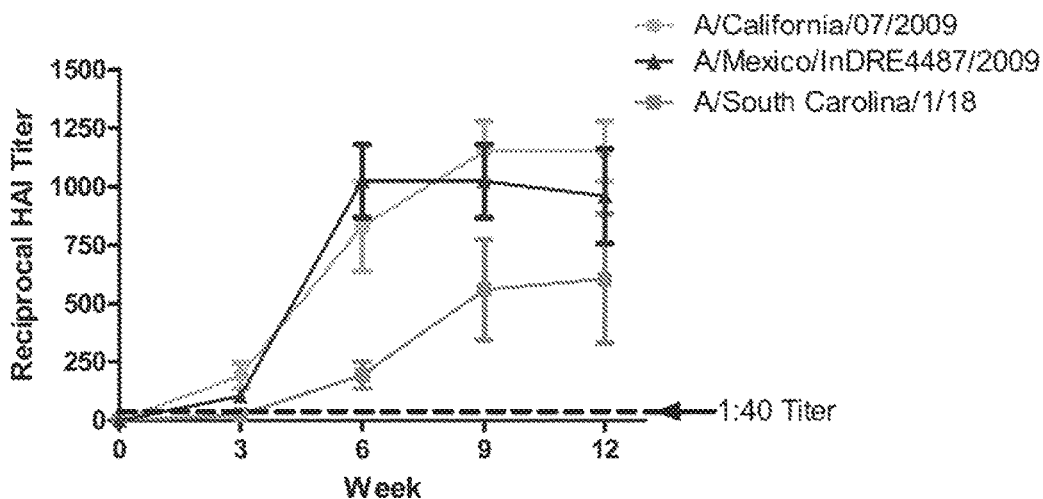

FIGS. 10A-B displays a number of graphs of inhibition titers generated from hemagglutination inhibition assays performed with sera from immunized guinea pigs (Combo (all 4 H1U, HS09, ConBris, and ConTT)) against various pandemic viruses; 10A showing the data points; and 10B showing the mean and standard deviation.

FIGS. 11A-C shows titer graphs generated from hemagglutination inhibition assays performed with sera from ferrets (immunized with combination of HS09 and H1U)

against either 11A) A/Mexico/InDRE4108/2009 pandemic strain; and 11B) A/Mexico/InDRE4487/2009 pandemic strain; and a graph showing percent of ferrets survival when challenged with 2009 H1 Mexico strain of influenza.

FIG. 12 displays an influenza B hemagluttinin (BHA) genetic tree of the genes from strains of the last 20 years, showing the genetic relationship between the various BHA strains.

FIG. 13A-F displays a number of graphs of inhibition titers generated from hemagglutination inhibition assays performed with sera from immunized mice (naïve, BHA-1 (SEQ ID NO: 13), BHA-2 (SEQ ID NO:25), Combo (both BHA-1 and BHA-2) against various viruses.

Figure 14:
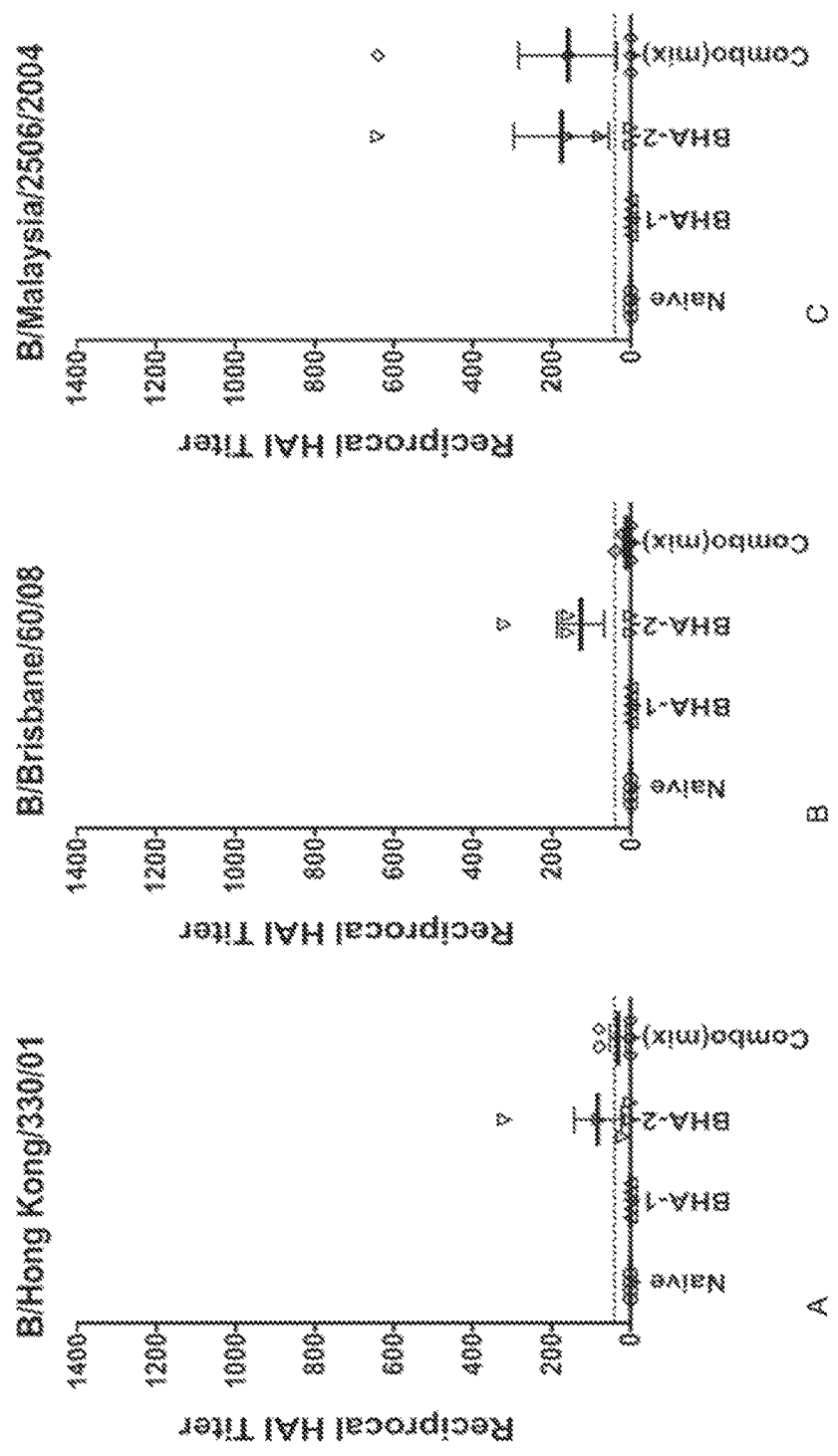
Figure 15:
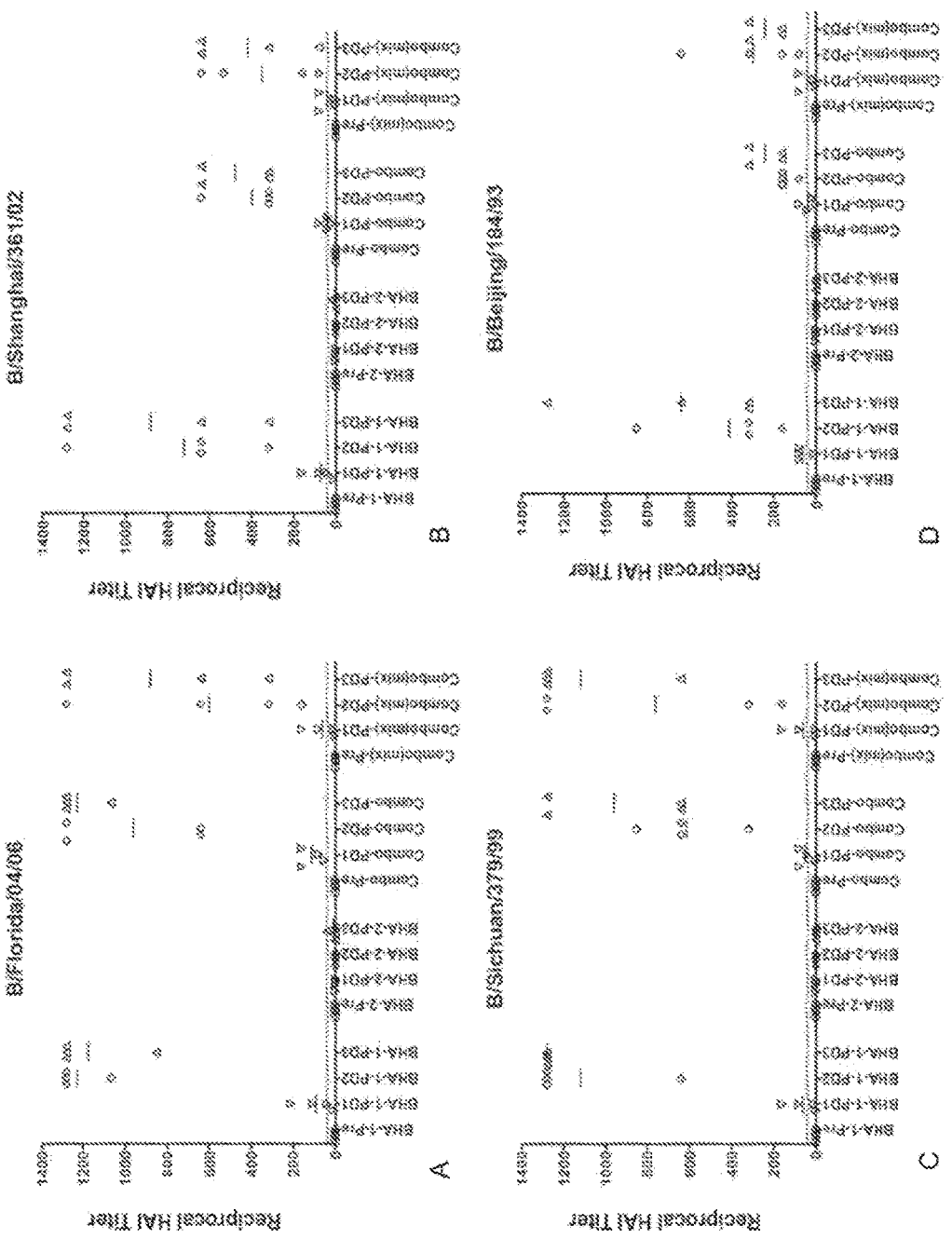

FIG. 14A-C displays a number of graphs of inhibition titers generated from hemagglutination inhibition assays performed with sera from immunized mice (naïve, BHA-1 (SEQ ID NO: 13), BHA-2 (SEQ ID NO:25), Combo (both BHA-1 and BHA-2)) against various viruses.

FIG. 15A-D displays a number of graphs of inhibition titers generated from hemagglutination inhibition assays performed with sera from immunized guinea pigs pre-immunization ("pre"), post-dose 1 ("PD1"), post-dose 2 ("PD2"), or post-dose 3 ("PD3") (BHA-1 (SEQ ID NO: 13), BHA-2 (SEQ ID NO:25), Combo (both BHA-1 and BHA-2) against various viruses.

Figure 16:
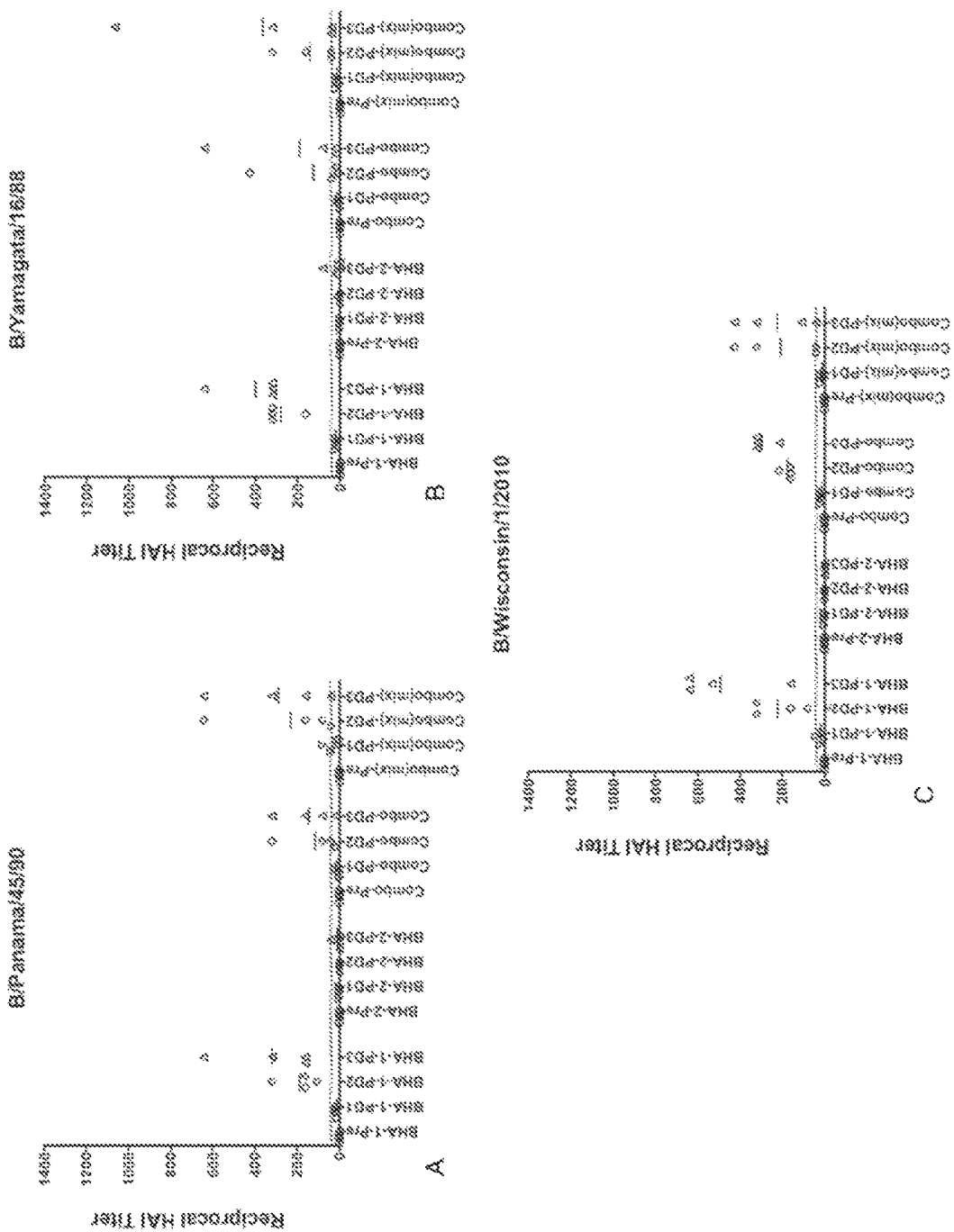

FIG. 16A-C displays a number of graphs of inhibition titers generated from hemagglutination inhibition assays performed with sera from immunized guinea pigs pre-immunization ("pre"), post-dose 1 ("PD1"), post-dose 2 ("PD2"), or post-dose 3 ("PD3") (BHA-1 (SEQ ID NO: 13), BHA-2 (SEQ ID NO:25), Combo (both BHA-1 and BHA-2) against various viruses.

Figure 17:
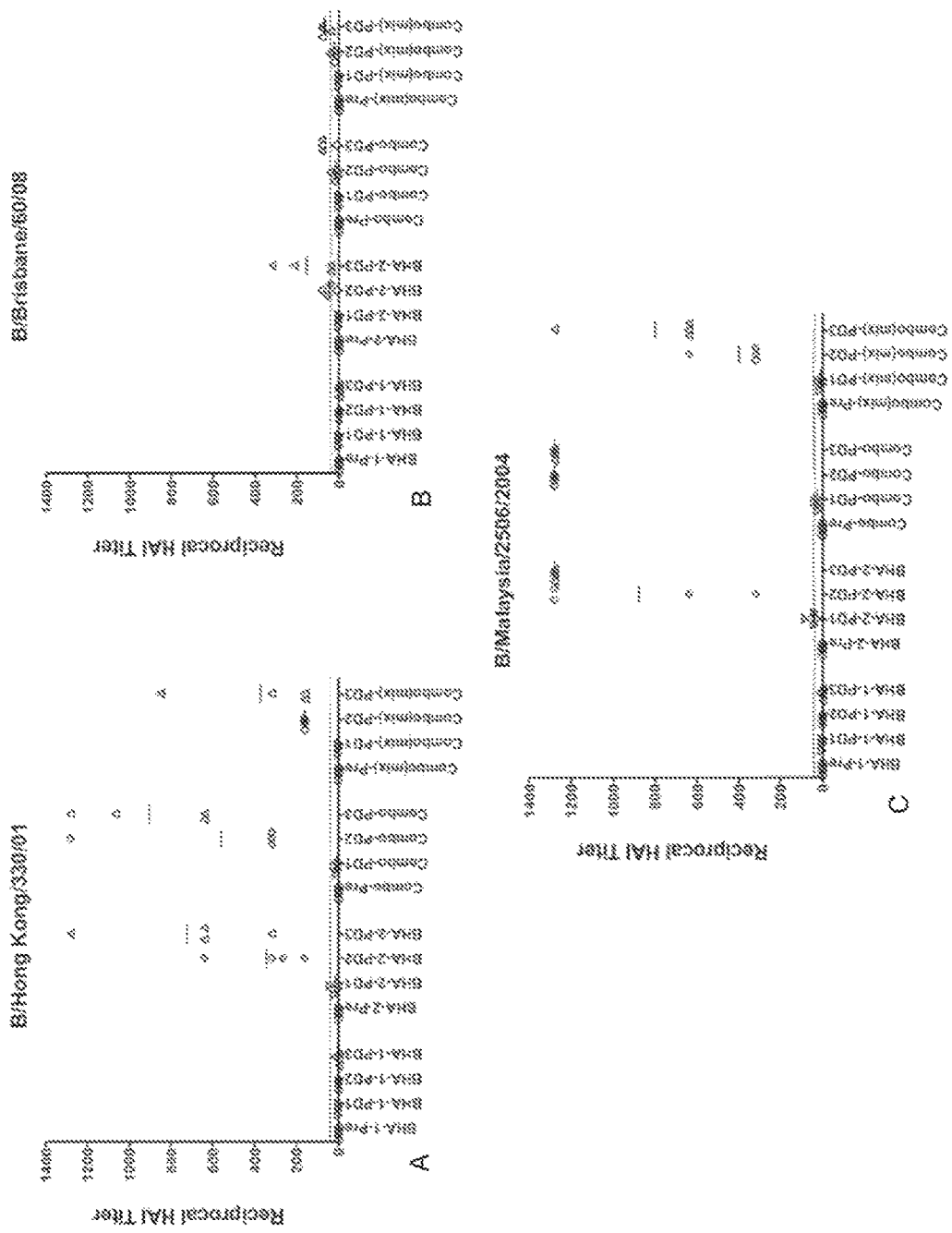

FIG. 17A-C displays a number of graphs of inhibition titers generated from hemagglutination inhibition assays performed with sera from immunized guinea pigs pre-immunization ("pre"), post-dose 1 ("PD1"), post-dose 2 ("PD2"), or post-dose 3 ("PD3") (BHA-1 (SEQ ID NO: 13), BHA-2 (SEQ ID NO:25), Combo (both BHA-1 and BHA-2) against various viruses.

Note: for FIGS. 15A-D; 16A-C; and 17A-C "Combo" samples are guinea pigs that were immunized with combo separately (BHA-1 delivered separately from BHA-2); whereas with combo(mix) BHA-1 and BHA-2 were mixed and delivered simultaneously.

FIG. 18 displays an influenza H3 hemagluttinin (H3HA) genetic tree of the genes from strains of the last 20 years, showing the genetic relationship between the various H3HA strains.

FIG. 19A-E displays a number of graphs of inhibition titers generated from hemagglutination inhibition assays performed with sera from immunized mice (naïve, H3HA-1 (SEQ ID NO: 37), H3HA-2 (SEQ ID NO:23), Combo (both H3HA-1 and H3HA-2) against various viruses.

FIG. 20A-F displays a number of graphs of inhibition titers generated from hemagglutination inhibition assays performed with sera from immunized mice (naïve, H3HA-1 (SEQ ID NO: 37), H3HA-2 (SEQ ID NO:23), Combo (both H3HA-1 and H3HA-2) against various viruses.

Figure 21:
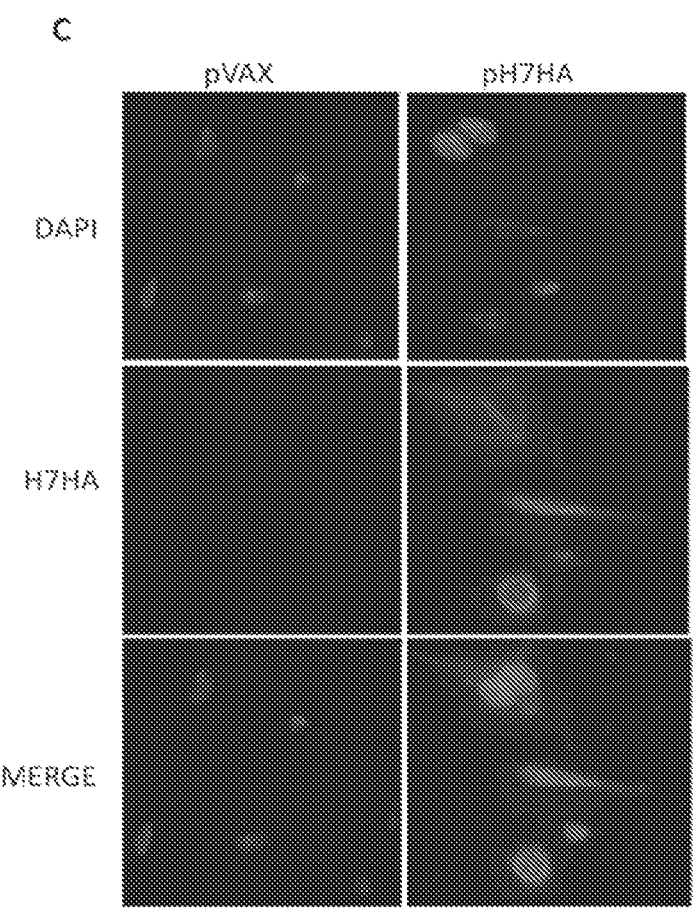

FIGS. 21A-21C show the H7N9 HA DNA vaccine design and its expression. (A) Phylogenetic tree based on neighbor-joining evaluation of H7HA alignment. Asterisks indicate location of consensus sequence. The strains used to generate the consensus HA are indicated. (B) The plasmid map of the H7HA plasmid. (C) Immunofluorescence assay of pH7HA. The transfected RD cells expressing H7HA protein showed typical red fluorescence. An anti-H7N9 HA mouse monoclonal antibody served as the source of primary antibody.

FIGS. 22A-22E show robust HA-specific IgG antibody titers and hemagglutination-inhibition titers in the sera of the immunized mice. (A) IgG antibodies against H7N9 A/Shanghai/1/2013 influenza HA protein. (B) IgG antibodies against H7N9 A/Anhui/1/2013 influenza HA protein. (C) IgG antibodies against H7N9 A/Hangzhou/1/2013 influenza HA protein. (D) HA-specific IgG endpoint titers. (E) Hemagglutination-inhibition titers against A/Anhui/1/2013. Each BALB/c mouse was immunized intramuscularly followed by electroporation with 25 μg of pH7HA DNA twice, three weeks apart. Mice (n=10) were bled before and two weeks after second immunization. IgG antibody titers and hemagglutination-inhibition titers were measured by endpoint enzyme-linked immunosorbent assay (ELISA) and hemagglutination-inhibition assay, respectively. Error bars represent 1 standard deviation from the mean.

Figure 23:
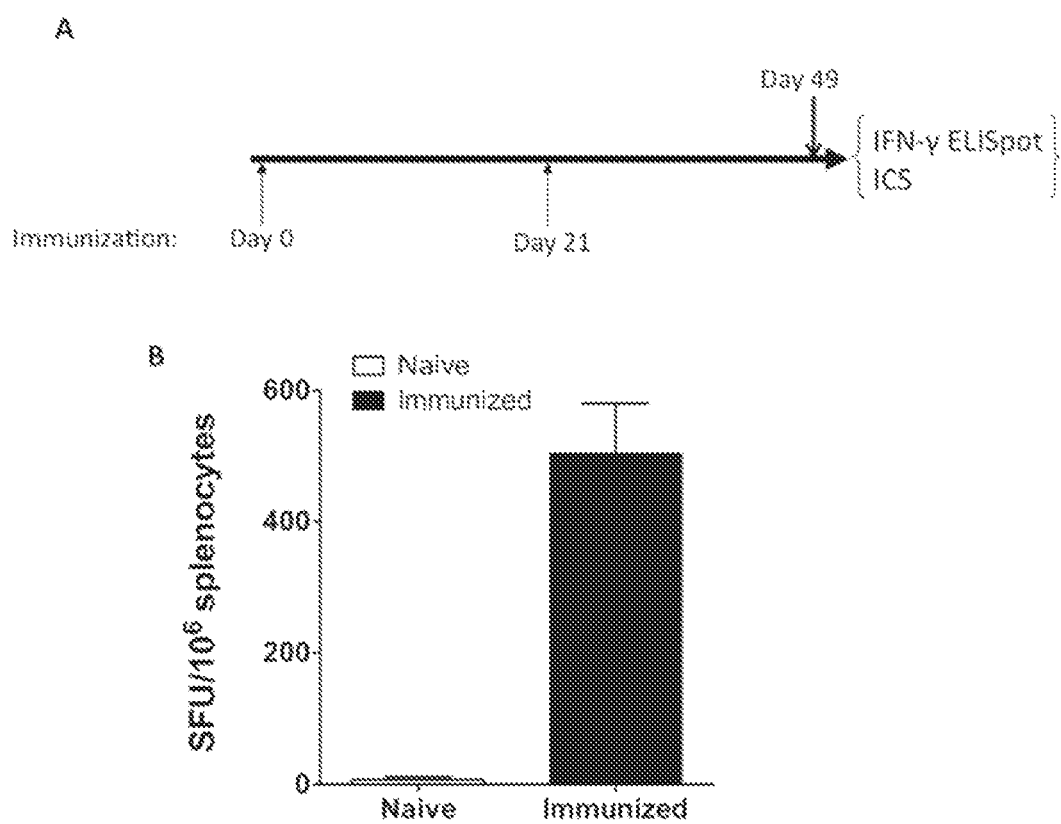

FIGS. 23A-23B show HA-specific cellular immune response induced in the immunized mice. (A) Immunization schedule. (B) Total IFN-γ responses induced by pH7HA. Frequencies of HA-specific IFN-γ-secreting cells per million splenocytes after two DNA immunizations with pH7HA were determined by IFN-γ ELISpot assay. The splenocytes were isolated from each mouse (n=5), stimulated in vitro with four overlapping HA peptide pools for 24 h and IFN-γ secreting cells were determined by ELISpot assay. Naïve mice were included as a negative control. The values are the means±standard error of the means.

FIGS. 24A-24C show cytokine frequencies and phenotypic profiles of specific CD4 T cells after pH7HA immunization. Cytokine recall responses to H7 HA were measured 4 weeks after last immunization by ICS and flow cytometry. CD4 T cells were identified by CD3 expression and further gated as CD44+. (A) The percentage of total CD44+CD4 T cells expressing IFN-γ in response to H7 HA stimulation. (B) Average percentage of HA-specific CD44+ CD4 double-positive-producing cells. (C) Multiparameter flow cytometry was used to determine the percentages of multifunctional CD4 T cell cytokine profile of H7HA. The bar chart shows the percentage of specific CD44+CD4 T cells displayed as triple, double, or single positive CD4 T cells. Pie charts show the relative proportion of each cytokine subpopulation to H7 HA stimulation. Background staining from cells stimulated with medium alone has been subtracted. Data represent the mean±SEM of five mice per group with *$P<0.001$, $P<0.01$, *$P<0.05$ using Student's t-test.

FIGS. 25A-25D show cytokine frequencies and phenotypic profiles of specific CD8 T cells after pH7HA immunization. Cytokine recall responses to H7 HA were measured 4 weeks after last immunization by ICS and flow cytometry. CD8 T cells were identified by CD3 expression and further gated as CD44+. (A) The percentage of total CD44+CD8 T cells expressing IFN-γ in response to H7 HA stimulation. (B) Average percentage of HA-specific CD44+ CD8 double-positive-producing cells. (C) Multiparameter flow cytometry was used to determine the percentages of multifunctional CD8 T cell cytokine profile of H7HA. The bar chart shows the percentage of specific CD44+CD8 T cells displayed as triple, double, or single positive CD8 T cells. Pie charts show the relative proportion of each cytokine subpopulation to H7 HA stimulation. (D) Antigen-specific cytolytic degranulation T cells were measured by degranulation marker expression, CD107a and IFN-γ. Background staining from cells stimulated with medium alone has been subtracted. Data represent the mean±SEM of five mice per group with *$P<0.001$, $P<0.01$, *$P<0.05$ using Student's t-test.

Figure 26:
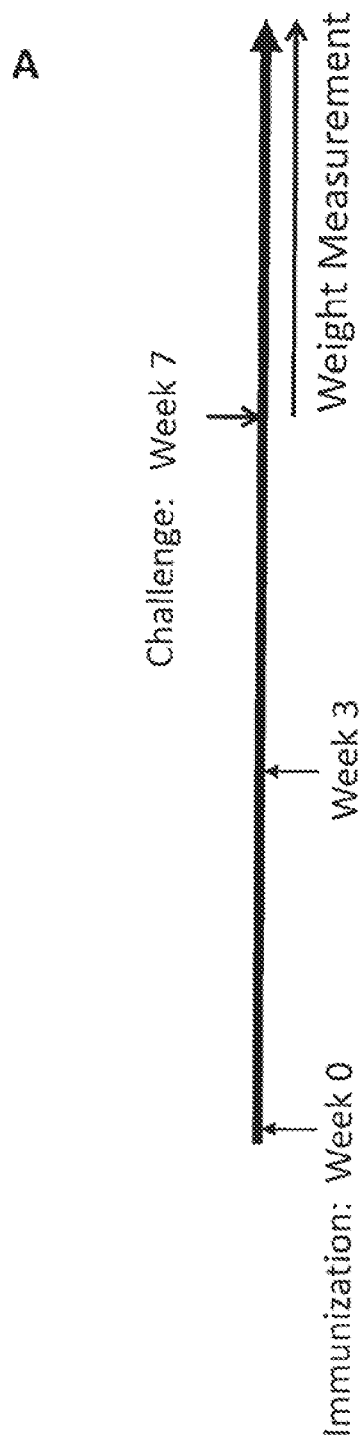
Figure 26:
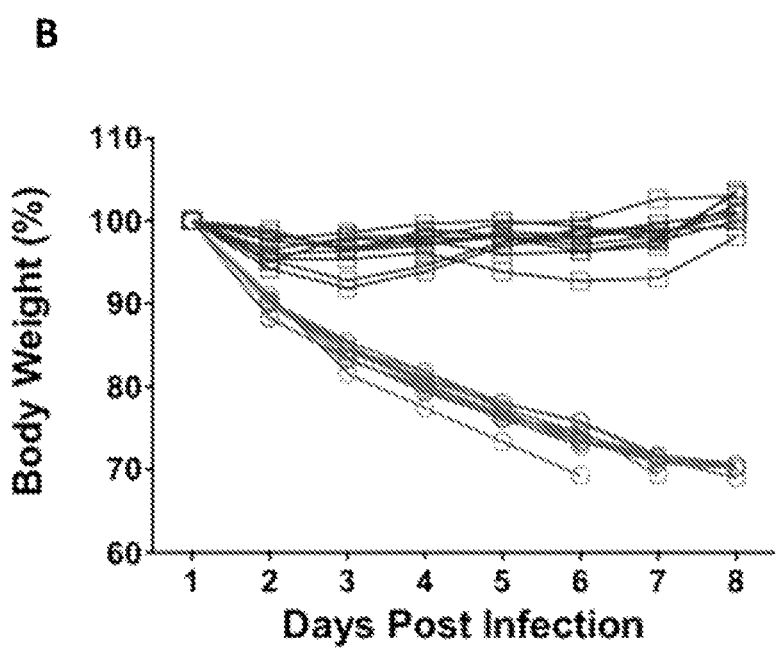
Figure 26:
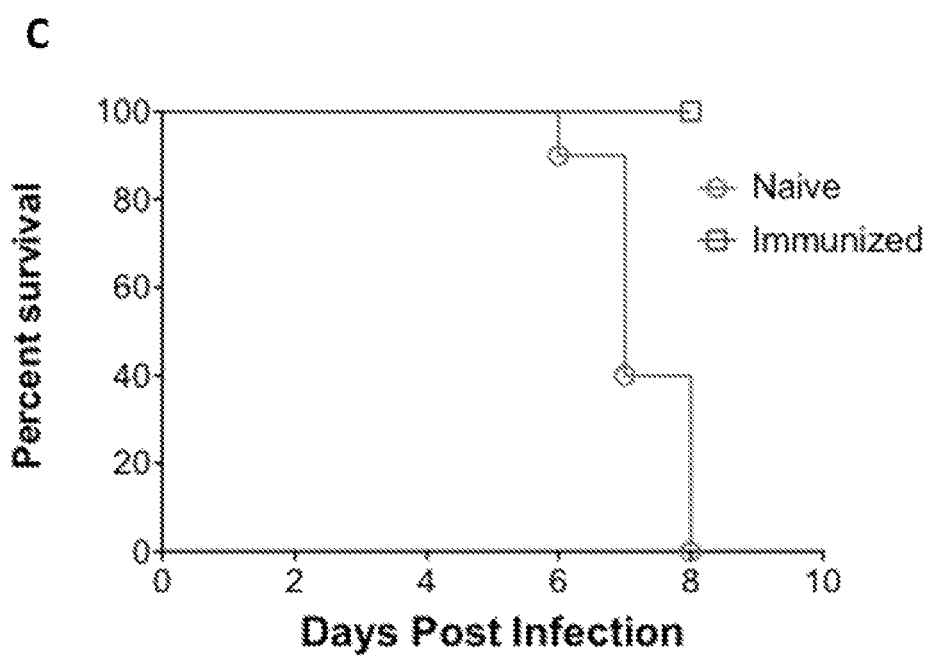

FIGS. 26A-26C show protection from H7N9 A/Anhui/12013 virus challenge in the immunized mice. (A) Experimental schedule of challenge study. The mice (n=10) were immunized with 25 µg of pH7HA twice, three weeks apart. Four weeks after the second immunization, the mice were challenged intranasally with a lethal dose of A/Anhui/1/13 H7N9 virus and monitored daily for weight loss and mortality. (B) Weight loss of each individual surviving mice in both naïve and immunized groups. The data are plotted as percentage of the weight on day 1. (C) Kaplan-Meier survival curve showing the percent survival following challenge. All surviving animals were monitored for a total of 28 days.

DETAILED DESCRIPTION

The present invention is directed to vaccines comprising consensus amino acid sequences of influenza H7N9 HA (referred to as "consensus H7N9 HA"; (SEQ ID NO: 40)). In some aspects, nucleic acid sequences are provided which encode proteins comprising the H7N9 HA consensus amino acid sequence of SEQ ID NO: 40.

Current vaccination platforms require significant development and production timelines to address pandemics. The synthetic H7N9 HA DNA vaccine is capable of eliciting robust cellular immune responses, broadly cross-reactive antibody responses and generating complete protection from lethal challenge with just a few week development and vaccination regime. The synthetic DNA vaccine platform eliminates many of the hurdles that limit the rapid development and deployment of a vaccine against an emerging pandemic. For example, the lack of a requirement for any recombination or in vivo production, as with other technologies, quickens the production time line as well as eliminates a major potential source of errors in seed development, thus increasing safety by limiting potential mutations being induced during the immunogen development process.

The disclosed enhanced DNA approach provides as influenza vaccine platform that 1) can be rapidly and straightforwardly utilized to design an effective vaccine against multiple known and new strains, 2) includes a delivery mechanism that can quickly induce cellular and humoral immune responses against new antigens in humans, 3) is rapid from design to scale up and mass production, with a relevant clinical track record and 4) is very stable for distribution purposes. Using this approach, millions of doses can be produced at scale within a few months of identification of the pathogen. In addition the stability of DNA and the lack of requirement of any viral amplification step ensure fidelity in the process.

While not being bound by scientific theory, a vaccine that can be used to elicit an immune response (humeral, cellular, or both) broadly against multiple H7N9 HA influenza subtypes can comprise one or more of the following: 1) a nucleic acid sequence that encodes a protein comprising the consensus H7N9 HA amino acid sequence; and 2) a protein comprising the consensus H7N9 HA amino acid sequence Immunization methods can be performed and vaccines can be prepared which use and/or combine two or more of the following components: 1) a nucleic acid sequence that encodes a protein comprising the consensus H7N9 HA amino acid sequence; and 2) a protein comprising the consensus H7N9 HA amino acid sequence.

The consensus H7N9 HA nucleic acid and/or amino acid sequence can be combined in a vaccine cocktail further comprising consensus amino acid sequences of influenza A H1 and H2 (referred to herein as "consensus H1S" or "HS09" (SEQ ID NO:2) and "consensus H2" or "H2HA" (SEQ ID NO:7), respectively), a synthetic hybrid consensus H1 influenza A hemagglutinin amino acid sequence (referred to herein as "consensus U2" or "H1U2" (SEQ ID NO:10)), a consensus amino acid sequence of influenza B hemagglutinin (referred to herein as "consensus BHA" or "BHA-1" (SEQ ID NO:13)), a consensus amino acid sequence H1Bris hemagluttinin "ConBris or "H1Bris" (SEQ ID NO:20), a consensus amino acid sequence H1TT hemagluttinin "ConTT" "H1TT" (SEQ ID NO:22), a consensus amino acid sequence H3 hemagluttinin or "H3HA-2" (SEQ ID NO:24), a consensus amino acid sequence influenza B hemagluttinin or "BHA-2" (SEQ ID NO:26), a consensus amino acid sequence H3 hemagluttinin or "H3HA-3" (SEQ ID NO:28), a consensus amino acid sequence H3 hemagluttinin or "H3HA-4" (SEQ ID NO:30), a consensus amino acid sequence influenza B hemagluttinin or "BHA-3" (SEQ ID NO:32), a consensus amino acid sequence influenza B hemagluttinin or "BHA-4" (SEQ ID NO:34), a synthetic hybrid consensus H1 influenza A hemagglutinin "consensus U" or "H1U" (SEQ ID NO:36), and a consensus amino acid sequence H3 hemagluttinin or "H3HA-1" (SEQ ID NO:38) are provided, which can provide protection of mammals against influenza. In addition, proteins are provided which comprise the consensus H1 amino acid sequence, the consensus H2 amino acid sequence, the consensus U2 amino acid sequence and/or the consensus BHA amino acid sequence. In some aspects, nucleic acid sequences are provided which encode proteins comprising the HS09 amino acid sequence (for example SEQ ID NO:1 or SEQ ID NO:3), the H2HA amino acid sequence (for example SEQ ID NO:6), the H1U2 amino acid sequence (for example SEQ ID NO:9 or SEQ ID NO:11), the BHA-1 amino acid sequence (for example SEQ ID NO:13) or (SEQ ID NO:15)), the H1Bris amino acid sequence (for example SEQ ID NO:19), the H1TT amino acid sequence (for example SEQ ID NO:21), the H3HA-2 amino acid sequence (for example SEQ ID NO:23), the BHA-2 amino acid sequence (for example SEQ ID NO:25), the H3HA-3 amino acid sequence (for example SEQ ID NO:27), the H3HA-4 amino acid sequence (for example SEQ ID NO:29), the BHA-3 amino acid sequence (for example SEQ ID NO:31), the BHA-4 amino acid sequence (for example SEQ ID NO:33), the H1U amino acid sequence (for example SEQ ID NO:35), and the H3HA-1 amino acid sequence (for example SEQ ID NO:37).

While not being bound by scientific theory, a combination H7N9 HA vaccine that can be used to elicit an immune response (humeral, cellular, or both) broadly against multiple influenza subtypes can comprise one or more of the following: 1) a nucleic acid sequence that encodes a protein comprising the consensus H7N9 HA amino acid sequence; 2) a protein comprising the consensus H7N9 HA amino acid sequence; 3) a nucleic acid sequence that encodes a protein comprising the consensus H1HA amino acid sequence; 4) a protein comprising the consensus H1HA amino acid sequence; 5) a nucleic acid sequence that encodes a protein comprising the consensus H2 amino acid sequence; 6) a protein comprising the consensus H2HA amino acid sequence; 7) a nucleic acid sequence that encodes a protein comprising the consensus H1U and/or H1U2 amino acid sequence; 8) a protein comprising the consensus H1U and/or H1U2 amino acid sequence; 9) a nucleic acid sequence that encodes a protein comprising the consensus BHA amino acid sequence; and 10) a protein comprising the consensus BHA amino acid sequence.

Immunization methods can be performed and vaccines can be prepared which use and/or combine two or more of the following components: 1) a nucleic acid sequence that encodes a protein comprising the consensus H7N9 HA amino acid sequence; 2) a protein comprising the consensus H7N9 HA amino acid sequence; 3) a nucleic acid sequence that encodes a protein comprising the consensus H1 amino acid sequence; 4) a protein comprising the consensus H1 amino acid sequence; 5) a nucleic acid sequence that encodes a protein comprising the consensus H2 amino acid sequence, 6) a protein comprising the consensus H2 amino acid sequence; 7) a nucleic acid sequence that encodes a protein comprising the consensus U2 amino acid sequence, 8) a protein comprising the consensus U2 amino acid sequence, 9) a nucleic acid sequence that encodes a protein comprising the consensus BHA amino acid sequence, and 10) a protein comprising the consensus BHA amino acid sequence. For more broad based treatments against influenza, immunization methods can be performed and vaccines can be prepared which use and/or combine one or more other influenza proteins such as influenza H7N9, influenza A H1-H16, influenza A N1-N9, influenza B hemagglutinin, influenza B neuraminidase and/or genes encoding these proteins together with one or more of the following components: 1) a nucleic acid sequence that encodes a protein comprising the consensus H7N9 amino acid sequence; 2) a protein comprising the consensus H7N9 amino acid sequence; 3) a nucleic acid sequence that encodes a protein comprising the consensus H1 amino acid sequence; 4) a protein comprising the consensus H1 amino acid sequence; 5) a nucleic acid sequence that encodes a protein comprising the consensus H2 amino acid sequence, 6) a protein comprising the consensus H2 amino acid sequence; 7) a nucleic acid sequence that encodes a protein comprising the consensus U2 amino acid sequence, 8) a protein comprising the consensus U2 amino acid sequence, 9) a nucleic acid sequence that encodes a protein comprising the consensus BHA amino acid sequence, and 10) a protein comprising the consensus BHA amino acid sequence.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein means any molecule added to the DNA plasmid vaccines described herein to enhance the immunogenicity of the antigens encoded by the DNA plasmids and the encoding nucleic acid sequences described hereinafter.

b. Antibody

"Antibody" as used herein means an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody can be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

d. Complement

"Complement" or "complementary" as used herein means a nucleic acid can mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein means a polypeptide sequence based on analysis of an alignment of multiple subtypes of a particular influenza antigen. Nucleic acid sequences that encode a consensus polypeptide sequence can be prepared. Vaccines comprising proteins that comprise consensus sequences and/or nucleic acid molecules that encode such proteins can be used to induce broad immunity against multiple subtypes or serotypes of a particular influenza antigen. Consensus influenza antigens can include influenza H7N9 HA consensus amino acid sequences, influenza A consensus hemagglutinin amino acid sequences, including for example consensus H1, consensus H2, or influenza B consensus hemagglutinin amino acid sequences.

f. Constant Current

"Constant current" as used herein means a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

g. Current Feedback or Feedback

"Current feedback" or "feedback" can be used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback can be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop can be instantaneous as it is an analog closed-loop feedback.

h. Decentralized Current

"Decentralized current" as used herein means the pattern of electrical currents delivered from the various needle electrode arrays of the electroporation devices described herein, wherein the patterns minimize, or preferably eliminate, the occurrence of electroporation related heat stress on any area of tissue being electroporated.

i. Electroporation

"Electroporation," "electro-permeabilization," or "electro-kinetic enhancement" ("EP") as used interchangeably herein means the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

j. Feedback Mechanism

"Feedback mechanism" as used herein means a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism can be performed by an analog closed loop circuit.

k. Fragment

"Fragment" as used herein with respect to nucleic acid sequences means a nucleic acid sequence or a portion thereof, that encodes a polypeptide capable of eliciting an immune response in a mammal that cross reacts with a full length wild type strain influenza antigen, including, e.g., an influenza H7N9 HA antigen, an influenza A H1 hemagglutinin, an influenza A H2 hemagglutinin or an influenza B hemagglutinin. The fragments can be DNA fragments selected from at least one of the various nucleotide sequences that encode the consensus amino acid sequences and constructs comprising such sequences, including SEQ ID NOS: 1, 6, 9, 13, 15, 19, 21, 23, 25, 27, 29, 31, 33, 35, 37 and 39; and nucleotide sequences encoding SEQ ID NOs: 2, 7, 10, 14, 20, 22, 24, 26, 28, 30, 32, 34, 36, 38 and 40. DNA fragments can comprise coding sequences for the immunoglobulin leader such as IgE or IgG sequences. The DNA fragments can be 30 or more nucleotides in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, 720 or more, 780 or more, 840 or more, 900 or more, 960 or more, 1020 or more, 1080 or more, 1140 or more, 1200 or more, 1260 or more, 1320 or more, 1380 or more, 1440 or more, 1500 or more, 1560 or more, 1620 or more, 1680 or more, 1740 or more, 1800 or more, 1860 or more, 1820 or more, 1880 or more, 1940 or more, 2000 or more, 2600 or more, 2700 or more, 2800 or more, 2900 or more, 2910 or more, 2920 or more, 2930 or more, 2931 or more, 2932 or more, 2933 or more, 2934 or more, 2935 or more, 2936 or more, 2937 or more, or 2938 or more in length. DNA fragments can be fewer than 10 nucleotides, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 720, fewer than 780, fewer than 840, fewer than 900, fewer than 960, fewer than 1020, fewer than 1080, fewer than 1140, fewer than 1200, fewer than 1260, fewer than 1320, fewer than 1380, fewer than 1440, fewer than 1500, fewer than 1560, fewer than 1620, fewer than 1680, or fewer than 1740 nucleotides, fewer than 1800, fewer than 1860, fewer than 1820, fewer than 1880, fewer than 1940, fewer than 2000, fewer than 2600, fewer than 2700, fewer than 2800, fewer than 2900, fewer than 2910, fewer than 2920, fewer than 2930, fewer than 2931, fewer than 2932, fewer than 2933, fewer than 2934, fewer than 2935, fewer than 2936, fewer than 2937, or fewer than 2938.

"Fragment" with respect to polypeptide sequences means a polypeptide capable of eliciting an immune response in a mammal that cross reacts with a full length wild type strain influenza antigen, including, e.g., an influenza A H1 hemagglutinin, an influenza A H2 hemagglutinin or an influenza B hemagglutinin. The fragment can be polypeptide fragment selected from at least one of the various polypeptide sequences of the present invention, including SEQ ID NOs: 2, 7, 10, 14, 20, 22, 24, 26, 28, 30, 32, 34, 36, 38 and 40. Polypeptide fragments can be analyzed to contact at least one antigenic epitope as provided by a publicly available database such as the Los Alamos National Laboratory's HA Sequence Database. Polypeptides HA fragments can further comprise amino acid sequences for the immunoglobulin leader such as IgE or IgG. The polypeptide fragments can be 30 or more amino acids in length, 45 or more, 60 or more, 75 or more, 90 or more, 120 or more, 150 or more, 180 or more, 210 or more, 240 or more, 270 or more, 300 or more, 360 or more, 420 or more, 480 or more, 540 or more, 600 or more, 660 or more, or 710 amino acids or more in length. Polypeptide fragments can be fewer than 10 amino acids, fewer than 20, fewer than 30, fewer than 40, fewer than 50, fewer than 60, fewer than 75, fewer than 90, fewer than 120, fewer than 150, fewer than 180, fewer than 210, fewer than 240, fewer than 270, fewer than 300, fewer than 360, fewer than 420, fewer than 480, fewer than 540, fewer than 600, fewer than 660, fewer than 700, fewer than 701, fewer than 702, fewer than 703, fewer than 704, fewer than 705, fewer than 706, fewer than 707, fewer than 708, fewer than 709, or fewer than 710 amino acids in length.

l. Genetic Construct

As used herein, the term "genetic construct" refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

m. Identical

"Identical" or "identity" as used herein in the context of two or more nucleic acids or polypeptide sequences, means that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

n. Impedance

"Impedance" can be used when discussing the feedback mechanism and can be converted to a current value according to Ohm's law, thus enabling comparisons with the preset current.

o. Immune Response

"Immune response" as used herein means the activation of a host's immune system, e.g., that of a mammal, in response to the introduction of antigen such as an influenza hemagglutinin consensus antigen. The immune response can be in the form of a cellular or humoral response, or both.

p. Nucleic Acid

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof. A single strand provides a probe that can hybridize to a target sequence under stringent hybridization conditions. Thus, a nucleic acid also encompasses a probe that hybridizes under stringent hybridization conditions.

Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

q. Operably Linked

"Operably linked" as used herein means that expression of a gene is under the control of a promoter with which it is spatially connected. A promoter can be positioned 5' (upstream) or 3' (downstream) of a gene under its control. The distance between the promoter and a gene can be approximately the same as the distance between that promoter and the gene it controls in the gene from which the promoter is derived. As is known in the art, variation in this distance can be accommodated without loss of promoter function.

r. Promoter

"Promoter" as used herein means a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

s. Stringent Hybridization Conditions

"Stringent hybridization conditions" as used herein means conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

t. Substantially Complementary

"Substantially complementary" as used herein means that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, 1440, 1530, 1620, 1710, 1800, 1890, 1980, 2070 or more nucleotides or amino acids, or that the two sequences hybridize under stringent hybridization conditions.

u. Substantially Identical

"Substantially identical" as used herein means that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, 630, 720, 810, 900, 990, 1080, 1170, 1260, 1350, 1440, 1530, 1620, 1710, 1800, 1890, 1980, 2070 or more nucleotides or amino acids, or over the entire length of the nucleic acid sequence or amino acid sequence, if the first sequence is substantially complementary to the complement of the second sequence.

v. Subtype or Serotype

"Subtype" or "serotype": as used herein, interchangeably, and in reference to influenza virus, means genetic variants of an influenza virus such that one subtype is recognized by an immune system apart from a different subtype.

w. Variant

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

x. Vector

"Vector" as used herein means a nucleic acid sequence containing an origin of replication. A vector can be a vector, bacteriophage, bacterial artificial chromosome or yeast artificial chromosome. A vector can be a DNA or RNA vector. A vector can be a self-replicating extrachromosomal vector, and preferably, is a DNA plasmid.

2. H7N9 HA Influenza Antigen

Provided herein are H7N9 antigens capable of eliciting an immune response in a mammal against one or more H7N9 influenza strains. The H7N9 antigen can be an hemagglutinin antigen (HA). The antigen can be capable of eliciting an immune response in a mammal against one or more H7N9 influenza strains, including against or more pandemic strains, such as the Chinese avian influenza A (H7N9). The antigen can comprise epitopes that make them particularly effective as immunogens against which, anti-H7N9 influenza immune responses can be induced.

The H7N9 antigen can comprise the full length translation product HA of H7N9, a variant thereof, a fragment thereof or a combination thereof. The influenza hemagglutinin H7N9 antigen can be a consensus sequence derived from multiple strains of influenza A serotype H7N9. The H7N9 antigen can contain at least one antigenic epitope that can be effective against particular influenza immunogens against which an immune response can be induced. The H7N9 antigen can provide an entire repertoire of immunogenic sites and epitopes present in an intact influenza H7N9 virus. The H7N9 antigen can be a consensus hemagglutinin antigen sequence that can be derived from hemagglutinin antigen sequences from a plurality of influenza A virus strains of one serotype H7N9. The antigen can be a hybrid consensus H7N9 hemagglutinin antigen sequence that can be derived from combining two different consensus H7N9 hemagglutinin antigen sequences or portions thereof. Each of two different consensus H7N9 hemagglutinin antigen sequences can be derived from a different set of a plurality of influenza A H7N9 virus strains of one serotype. The antigen can be a consensus H7N9 hemagglutinin antigen sequence that can be derived from H7N9 hemagglutinin antigen sequences from a plurality of influenza A H7N9 virus strains.

The consensus H7N9 hemagglutinin antigen may be encoded by an isolated nucleic acid. The isolated nucleic acid can be a nucleic acid sequence encoding an amino acid sequence selected from the group consisting of SEQ ID NO: 40, an amino acid sequence that is 95% identical over the entire length of the amino acid sequence of SEQ ID NO: 40, a fragment of SEQ ID NO: 40 comprising at least 30 amino acids, and an amino acid sequence that is 95% identical to a fragment of SEQ ID NO: 40 comprising at least 30 amino acids. The isolated nucleic acid can be a nucleic acid sequence encoding an amino acid sequence of SEQ ID NO: 40. The isolated nucleic acid can be a nucleic acid sequence of SEQ ID NO: 39.

The consensus H7N9 hemagglutinin antigen can be a protein comprising SEQ ID NO: 40 (the consensus HA amino acid sequence of Chinese avian influenza A (H7N9)) wherein amino acids 1-560 correspond to the HA consensus amino acid sequence.

The consensus H7N9 hemagglutinin antigen can further comprise one or more additional amino acid sequence elements. The consensus H7N9 hemagglutinin antigen can further comprise on its N-terminal an IgE or IgG leader amino acid sequence. The IgE leader amino acid sequence can be SEQ ID NO: 17. The consensus H7N9 hemagglutinin antigen can further comprise an immunogenic tag which is a unique immunogenic epitope that can be detected by readily available antibodies. An example of such an immunogenic tag is the 9 amino acid influenza HA Tag which can be linked on the consensus H7N9 hemagglutinin antigen terminus. The HA Tag amino acid sequence can be SEQ ID NO:18. In some embodiments, consensus H7N9 hemagglutinin antigen can further comprise on its N-terminal an IgE or IgG leader amino acid sequence and on its C terminal an HA tag.

The consensus H7N9 hemagglutinin antigen can be a consensus H7N9 hemagglutinin HA protein that consists of consensus influenza amino acid sequences or fragments and variants thereof. The consensus H7N9 hemagglutinin antigen can be a consensus hemagglutinin protein that comprises non-influenza protein sequences and influenza protein sequences or fragments and variants thereof.

Examples of a consensus H7N9 hemagglutinin antigen HA protein include those that can consist of the consensus H7N9 hemagglutinin antigen amino acid sequence (SEQ ID NO:40) or those that further comprise additional elements such as an IgE leader sequence, or an HA Tag or both an IgE leader sequence and an HA Tag. An example of the consensus H7N9 hemagglutinin antigen HA protein can include both an IgE leader sequence and an HA Tag, which comprises the consensus H7N9 hemagglutinin antigen HA amino acid coding sequence (SEQ ID NO:2) linked to the IgE leader amino acid sequence (SEQ ID NO: 17) at its N terminal and linked to the HA Tag (SEQ ID NO:18) at its C terminal.

The consensus H7N9 hemagglutinin protein can be encoded by a consensus H7N9 hemagglutinin nucleic acid, a variant thereof or a fragment thereof. Unlike the consensus H7N9 hemagglutinin protein which can be a consensus sequence derived from a plurality of different H7N9 hemagglutinin sequences from different strains and variants, the consensus H7N9 hemagglutinin nucleic acid refers to a nucleic acid sequence that encodes a consensus protein sequence and the coding sequences used can differ from those used to encode the particular amino acid sequences in the plurality of different H7N9 hemagglutinin sequences from which the consensus H7N9 hemagglutinin protein sequence is derived. The consensus nucleic acid sequence can be codon optimized and/or RNA optimized. The consensus H7N9 hemagglutinin nucleic acid sequence can comprise a Kozak's sequence in the 5' untranslated region. The consensus H7N9 hemagglutinin nucleic acid sequence can comprise nucleic acid sequences that encode a leader sequence. The coding sequence of an N terminal leader sequence is 5' of the H7N9 hemagglutinin coding sequence. The N-terminal leader can facilitate secretion. The N-terminal leader can be an IgE leader or an IgG leader. The consensus H7N9 hemagglutinin nucleic acid sequence can comprise nucleic acid sequences that encode an immunogenic tag. The immunogenic tag can be on the C terminus of the protein and the sequence encoding it is 3' of the HA coding sequence. The immunogenic tag provides a unique epitope for which there are readily available antibodies so that such antibodies can be used in assays to detect and confirm expression of the protein. The immunogenic tag can be an H Tag at the C-terminus of the protein.

Consensus H7N9 hemagglutinin nucleic acid can have a polynucleotide sequence that encodes a protein that comprises the amino acid sequence of SEQ ID NO: 40. The consensus H7N9 hemagglutinin nucleic acid can comprise the nucleic sequence of SEQ ID NO: 39. The consensus H7N9 hemagglutinin nucleic acid can further comprise a polynucleotide sequence encoding the IgE leader amino acid sequence, or a polynucleotide sequence encoding an HA Tag amino acid sequence, or both. SEQ ID NO: 17 is an IgE leader polypeptide sequence. SEQ ID NO: 18 is an HA Tag polypeptide sequence. Examples of H7N9 hemagglutinin consensus nucleic acids that further comprise polynucleotide sequences encoding an IgE leader sequence and an HA Tag include nucleic acid molecules that encode proteins that comprise amino acid sequence of SEQ ID NO: 40.

The synthetic H7N9 HA nucleic acid is capable of eliciting robust cellular immune responses, broadly cross-reactive antibody responses and generating complete protection from lethal challenge with just a few week development and vaccination regime due to the consensus sequence across many different strains of H7N9. For example, the disclosed enhanced DNA approach provides as influenza vaccine platform that 1) can be rapidly and straightforwardly utilized to design an effective vaccine against multiple known and new strains, 2) includes a delivery mechanism that can quickly induce cellular and humoral immune responses against new antigens in humans, 3) is rapid from design to scale up and mass production, with a relevant clinical track record and 4) is very stable for distribution purposes. Using this approach, millions of doses can be produced at scale within a few months of identification of the pathogen. In addition the stability of DNA and the lack of requirement of any viral amplification step ensure fidelity in the process.

3. Combinational Influenza Antigens

Provided herein are antigens capable of eliciting an immune response in a mammal against one or more influenza serotypes in combination with the H7N9 antigen as discussed above. The antigen that can be combined with the H7N9 antigen can be capable of eliciting an immune response in a mammal against one or more influenza serotypes, including against one or more pandemic strains, such as 2009 H1N1 swine or H7N9 avian originated influenza. The antigen can be capable of eliciting an immune response in a mammal against one or more influenza serotype, including against one or more strains of swine or avian derived human influenza. The antigen can comprise epitopes that make them particularly effective as immunogens against which anti-influenza immune responses can be induced.

The antigen can comprise the full length translation product HA0, subunit HA1, subunit HA2, a variant thereof, a fragment thereof or a combination thereof. The influenza hemagglutinin antigen can be a consensus sequence derived from multiple strains of influenza A serotype H1, a consensus sequence derived from multiple strains of influenza A serotype H2, a hybrid sequence containing portions of two different consensus sequences derived from different sets of multiple strains of influenza A serotype H1 or a consensus sequence derived from multiple strains of influenza B. The influenza hemagglutinin antigen can be from influenza B. The antigen can contain at least one antigenic epitope that can be effective against particular influenza immunogens against which an immune response can be induced. The antigen can provide an entire repertoire of immunogenic sites and epitopes present in an intact influenza virus. The antigen can be a consensus hemagglutinin antigen sequence that can be derived from hemagglutinin antigen sequences from a plurality of influenza A virus strains of one serotype such as a plurality of influenza A virus strains of serotype H1 or of serotype H2. The antigen can be a hybrid consensus hemagglutinin antigen sequence that can be derived from combining two different consensus hemagglutinin antigen sequences or portions thereof. Each of two different consensus hemagglutinin antigen sequences can be derived from a different set of a plurality of influenza A virus strains of one serotype such as a plurality of influenza A virus strains of serotype H1. The antigen can be a consensus hemagglutinin antigen sequence that can be derived from hemagglutinin antigen sequences from a plurality of influenza B virus strains.

The consensus hemagglutinin antigen can be a protein comprising SEQ ID NO: 2 (the consensus H1 amino acid sequence) wherein amino acids 1-343 correspond to the HA1 subunit of the precursor HA0 consensus H1 amino acid sequence and amino acids 344-566 correspond to the HA2 subunit of the HA0 consensus H1 amino acid sequence. The consensus hemagglutinin antigen can also be a consensus hemagglutinin protein derived from hemagglutinin sequences from H1HA strains, such as a protein comprising SEQ ID NO: 20 (H1Bris) or SEQ ID NO:22 (H1TT). The consensus hemagglutinin antigen can be a protein comprising SEQ ID NO: 7 (H2HA). The consensus hemagglutinin antigen can be a consensus hemagglutinin protein derived from hemagglutinin sequences from H3HA strains, such as a protein comprising SEQ ID NO:24 (H3HA-2), SEQ ID NO:28 (H3HA-3), SEQ ID NO:30 (H3HA-4), or SEQ ID NO: 38 (H3HA-1). The consensus hemagglutinin antigen can be a synthetic hybrid consensus H1 sequences comprising portions of two different consensus H1 sequences which are each derived from a different set of sequences from the other. An example of a consensus HA antigen that is a synthetic hybrid consensus H1 protein is a protein comprising SEQ ID NO: 10 (H1U2) or SEQ ID NO:36 (H1U). The consensus hemagglutinin antigen can be a consensus hemagglutinin protein derived from hemagglutinin sequences from influenza B strains, such as a protein comprising SEQ ID NO: 14 (BHA-1), SEQ ID NO: 26 (BHA-2), SEQ ID NO: 32 (BHA-3), or SEQ ID NO: 34 (BHA-4).

The consensus hemagglutinin antigen can further comprise one or more additional amino acid sequence elements. The consensus hemagglutinin antigen can further comprise on its N-terminal an IgE or IgG leader amino acid sequence. The IgE leader amino acid sequence can be SEQ ID NO: 17. The consensus hemagglutinin antigen can further comprise an immunogenic tag which is a unique immunogenic epitope that can be detected by readily available antibodies. An example of such an immunogenic tag is the 9 amino acid influenza HA Tag which can be linked on the consensus hemagglutinin C terminus. The HA Tag amino acid sequence can be SEQ ID NO:18. In some embodiments, consensus hemagglutinin antigen can further comprise on its N-terminal an IgE or IgG leader amino acid sequence and on its C terminal an HA tag.

The consensus hemagglutinin antigen can be a consensus hemagglutinin protein that consists of consensus influenza amino acid sequences or fragments and variants thereof. The consensus hemagglutinin antigen can be a consensus hemagglutinin protein that comprises non-influenza protein sequences and influenza protein sequences or fragments and variants thereof.

Examples of a consensus H1 protein include those that can consist of the consensus H1 amino acid sequence (SEQ ID NO:2) or those that further comprise additional elements such as an IgE leader sequence, or an HA Tag or both an IgE leader sequence and an HA Tag. An example of the consensus H1 protein that includes both an IgE leader sequence and an HA Tag is SEQ ID NO: 4, which comprises the consensus H1 amino acid coding sequence (SEQ ID NO:2) linked to the IgE leader amino acid sequence (SEQ ID NO: 17) at its N terminal and linked to the HA Tag (SEQ ID NO:18) at its C terminal.

Examples of consensus H2 proteins include those that can consist of the consensus H2 amino acid sequence (SEQ ID NO:7) or those that further comprise an IgE leader sequence, or an HA Tag, or both an IgE leader sequence and an HA Tag.

Examples of hybrid consensus H1 proteins include those that can consist of the consensus U2 amino acid sequence (SEQ ID NO:10) or those that further comprise an IgE leader sequence, or an HA Tag, or both an IgE leader sequence and an HA Tag. An example of the consensus U2 protein is SEQ ID NO:12, which comprises the consensus U2 amino acid sequence (SEQ ID NO:10) linked to the IgE leader amino acid sequence (SEQ ID NO: 17) at its N terminal and linked to the HA Tag (SEQ ID NO:18) at its C terminal.

Examples of hybrid consensus influenza B hemagglutinin proteins include those that can consist of the consensus BHA amino acid sequence (SEQ ID NO:14) or it can comprise an IgE leader sequence, or an HA Tag, or both an IgE leader sequence and an HA Tag. An example of the consensus BHA protein is SEQ ID NO:16 which comprises the consensus BHA amino acid sequence (SEQ ID NO:14) linked to the IgE leader amino acid sequence (SEQ ID NO: 17) at its N terminal and linked to the HA Tag (SEQ ID NO:18) at its C terminal.

The consensus hemagglutinin protein can be encoded by a consensus hemagglutinin nucleic acid, a variant thereof or a fragment thereof. Unlike the consensus hemagglutinin protein which can be a consensus sequence derived from a plurality of different hemagglutinin sequences from different strains and variants, the consensus hemagglutinin nucleic acid refers to a nucleic acid sequence that encodes a consensus protein sequence and the coding sequences used can differ from those used to encode the particular amino acid sequences in the plurality of different hemagglutinin sequences from which the consensus hemagglutinin protein sequence is derived. The consensus nucleic acid sequence can be codon optimized and/or RNA optimized. The consensus hemagglutinin nucleic acid sequence can comprise a Kozak's sequence in the 5' untranslated region. The consensus hemagglutinin nucleic acid sequence can comprise nucleic acid sequences that encode a leader sequence. The coding sequence of an N terminal leader sequence is 5' of the hemagglutinin coding sequence. The N-terminal leader can facilitate secretion. The N-terminal leader can be an IgE leader or an IgG leader. The consensus hemagglutinin nucleic acid sequence can comprise nucleic acid sequences that encode an immunogenic tag. The immunogenic tag can be on the C terminus of the protein and the sequence encoding it is 3' of the HA coding sequence. The immunogenic tag provides a unique epitope for which there are readily available antibodies so that such antibodies can be used in assays to detect and confirm expression of the protein. The immunogenic tag can be an H Tag at the C-terminus of the protein.

Consensus hemagglutinin nucleic acid can have a polynucleotide sequence that encodes a protein that comprises the amino acid sequence of SEQ ID NO: 2, SEQ ID NO:7, SEQ ID NO:10, SEQ ID NO:14, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38. A consensus hemagglutinin nucleic acid that encodes SEQ ID NO: 2, SEQ ID NO:7, SEQ ID NO:10, SEQ ID NO:14, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38 can be SEQ ID NO:1, SEQ ID NO:6, SEQ ID NO:9, SEQ ID NO:13, SEQ ID NO:21, SEQ ID NO:23, SEQ ID NO:25, SEQ ID NO:27, SEQ ID NO:29, SEQ ID NO:31, SEQ ID NO:33, SEQ ID NO:35, or SEQ ID NO:37 respectively. The consensus hemagglutinin nucleic acid can further comprise a polynucleotide sequence encoding the IgE leader amino acid sequence, or a polynucleotide sequence encoding an HA Tag amino acid sequence, or both. SEQ ID NO: 17 is an IgE leader polypeptide sequence. SEQ ID NO: 18 is an HA Tag polypeptide sequence. Examples of hemagglutinin consensus nucleic acids that further comprise polynucleotide sequences encoding an IgE leader sequence and an HA Tag include nucleic acid molecules that encode proteins that comprise the amino acid sequence of SEQ ID NO:4, SEQ ID NO:12 or SEQ ID NO:16. A consensus hemagglutinin nucleic acid that encodes SEQ ID NO:4, SEQ ID NO:12 or SEQ ID NO:16 can be SEQ ID NO:3, SEQ ID NO:11 or SEQ ID NO:15, respectively.

4. Genetic Constructs and Plasmids

Provided herein are genetic constructs that can comprise a nucleic acid sequence that encodes the hemagglutinin H7N9 antigen and hemagglutinin from other influenza serotypes as described above. The genetic construct can be present in the cell as a functioning extrachromosomal molecule comprising the nucleic acid encoding the hemagglutinin antigen. The genetic construct comprising the nucleic acid encoding the hemagglutinin antigen can be linear minichromosome including centromere, telomers or plasmids or cosmids.

The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

The genetic constructs can comprise regulatory elements for gene expression of the hemagglutinin nucleic acid. The regulatory elements can be a promoter, an enhancer an initiation codon, a stop codon, or a polyadenylation signal.

Compositions can comprise nucleic acid sequences of one or more of: SEQ ID NO:1, SEQ ID NO:6, SEQ ID NO:9, SEQ ID NO:13, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, or SEQ ID NO: 39. Compositions can comprise a first nucleic acid sequence which encodes the hemagglutinin consensus antigen selected from the group consisting of one or more of: influenza A consensus hemagglutinin H7N9, influenza A consensus hemagglutinin H1 antigen, influenza A consensus hemagglutinin H2 antigen, influenza A consensus hemagglutinin H1U and/or H1U2 antigen, and influenza B consensus hemagglutinin protein BHA, which can include SEQ ID NO:1, SEQ ID NO:6, SEQ ID NO:9, SEQ ID NO:13, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO: 39 or nucleic acid sequences that encode one or more of: SEQ ID NO:2, SEQ ID NO:7, SEQ ID NO:10, SEQ ID NO:14, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, or SEQ ID NO: 40; and can further comprise one or more additional nucleic acid sequence(s) that encodes one or more protein(s) selected from the group consisting of: influenza A hemagglutinin proteins H1, H2, H3, H4, H5, H6, H7, H8, H9, H10, H11, H12, H13, H14, H15, H16, H7N9, influenza A neuraminidase N1, N2, N3, N4, N5, N6, N7, N8, N9, influenza B hemagglutinin (BHA) and influenza B neuraminidase (BNA), including one or more of the consensus sequences provided herein. The first and additional nucleic acid sequences can be present on the same nucleic acid molecule or different nucleic acid molecules. The first and additional nucleic acid sequences can be under the control of regulatory elements that function in a human cell. The additional coding sequence can encode one or more H1, H2, H3, H4, H5, H6, H7, H8, H9, H10, H11, H12, H13, H14, H15, H16, H7N9, N1, N2, N3, N4, N5, N6, N7, N8, N9, BHA and BNA from one or more strains of influenza, or be a consensus derived from a plurality of strains having the serotype, or be a hybrid which includes sequences from two or more consensus sequences.

The nucleic acid sequences can make up a genetic construct that can be a vector. The vector can be capable of expressing a consensus hemagglutinin antigen in the cell of a mammal in a quantity effective to elicit an immune response in the mammal. The vector can be recombinant. The vector can comprise heterologous nucleic acid encoding the consensus hemagglutinin antigen. The vector can be a plasmid. The vector can be useful for transfecting cells with nucleic acid encoding a consensus hemagglutinin antigen, which the transformed host cell is cultured and maintained under conditions wherein expression of the consensus hemagglutinin antigen takes place.

The vector can comprise heterologous nucleic acid encoding a consensus hemagglutinin antigen and can further comprise an initiation codon, which can be upstream of the consensus hemagglutinin coding sequence, and a stop codon, which can be downstream of the consensus hemagglutinin coding sequence. The initiation and termination codon can be in frame with the consensus hemagglutinin coding sequence. The vector can also comprise a promoter that is operably linked to the consensus hemagglutinin coding sequence. The promoter operably linked to the consensus hemagglutinin coding sequence can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter can also be a promoter from a human gene such as human actin, human myosin, human hemoglobin, human muscle creatine, or human metalothionein. The promoter can also be a tissue specific promoter, such as a muscle or skin specific promoter, natural or synthetic. Examples of such promoters are described in US patent application publication no. US20040175727, the contents of which are incorporated herein in its entirety.

The vector can also comprise a polyadenylation signal, which can be downstream of the HA coding sequence. The polyadenylation signal can be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal can be a polyadenylation signal from a pCEP4 vector (Invitrogen, San Diego, Calif.).

The vector can also comprise an enhancer upstream of the consensus hemagglutinin coding. The enhancer can be necessary for DNA expression. The enhancer can be human actin, human myosin, human hemoglobin, human muscle creatine or a viral enhancer such as one from CMV, HA, RSV or EBV. Polynucleotide function enhances are described in U.S. Pat. Nos. 5,593,972, 5,962,428, and WO94/016737, the contents of each are fully incorporated by reference.

Figure 1:
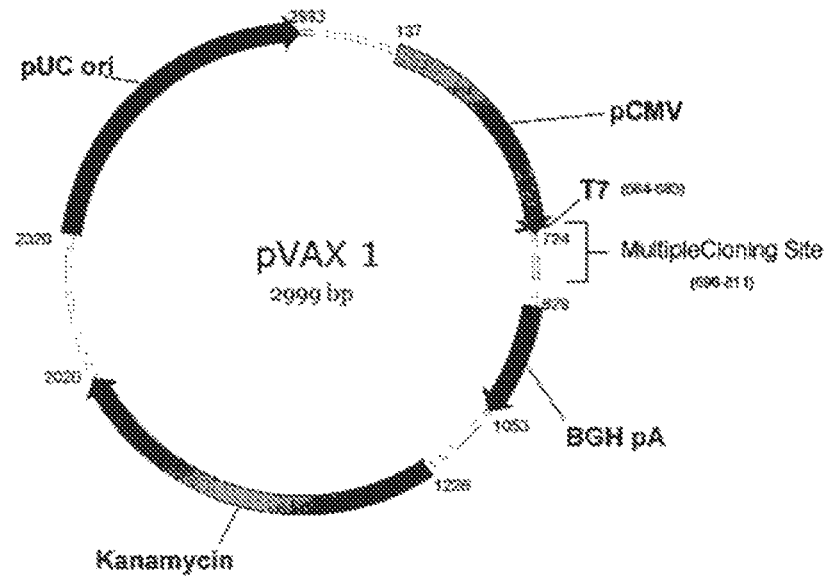
FIG. 1 is a map of the 2999 basepair backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

The vector can also comprise a mammalian origin of replication in order to maintain the vector extrachromosomally and produce multiple copies of the vector in a cell. The vector can be pVAX1 (FIG. 1), pCEP4 or pREP4 from Invitrogen (San Diego, Calif.), which can comprise the Epstein Barr virus origin of replication and nuclear antigen EBNA-1 coding region, which can produce high copy episomal replication without integration. The vector can be pVAX1 with changes such as those described in the paragraph referring to FIG. 1 in the Brief Description of the Figures section above. The backbone of the vector can be pAV0242. The vector can be a replication defective adenovirus type 5 (Ad5) vector.

The vector can also comprise a regulatory sequence, which can be well suited for gene expression in a mammalian or human cell into which the vector is administered. The consensus hemagglutinin coding sequence can comprise a codon, which can allow more efficient transcription of the coding sequence in the host cell.

The vector can be pSE420 (Invitrogen, San Diego, Calif.), which can be used for protein production in *Escherichia coli* (*E. coli*). The vector can also be pYES2 (Invitrogen, San Diego, Calif.), which can be used for protein production in *Saccharomyces cerevisiae* strains of yeast. The vector can also be of the MAXBAC™ complete baculovirus expression system (Invitrogen, San Diego, Calif.), which can be used for protein production in insect cells. The vector can also be pcDNA I or pcDNA3 (Invitrogen, San Diego, Calif.), which can be used for protein production in mammalian cells such as Chinese hamster ovary (CHO) cells. The vector can be expression vectors or systems to produce protein by routine techniques and readily available starting materials including Sambrook et al., Molecular Cloning: A Laboratory Manual, Second Ed., Cold Spring Harbor (1989), which is incorporated fully by reference.

The vector can be pGX2009 or pGX2006, which can be used for expressing the consensus hemagglutinin antigen. The vector pGX2009 (4739 bp, FIG. 2; SEQ ID NO: 5) is a modified pVAX1 plasmid with a nucleic acid sequence that encodes a consensus H1 protein (amino acid SEQ ID NO:4 encoded by SEQ ID NO:3) that comprises an IgE leader sequence (amino acid SEQ ID NO:12 encoded by SEQ ID NO:11) linked to a consensus H1 amino acid sequence (amino acid SEQ ID NO:2 encoded by SEQ ID NO:1). The vector pGX2006 (4628 bp; FIG. 3, SEQ ID NO:8) is a pVAX1 plasmid with a nucleic acid sequence that encodes a consensus H2 protein (amino acid SEQ ID NO:7 encoded by SEQ ID NO:6). Alternatively, in a similar DNA plasmid backbone pVAX1 as pGX2006 (or pVAX (Invitrogen), a nucleic acid insert can replace the H2HA sequence with any one of the following: SEQ ID NO:1, SEQ ID NO:6, SEQ ID NO:9, SEQ ID NO:13, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, or nucleic acid sequences that encode one or more of: SEQ ID NO:2, SEQ ID NO:7, SEQ ID NO:10, SEQ ID NO:14, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38; or any fragments and variants described herein.

The genetic constructs and components disclosed herein which include consensus hemagglutinin coding sequences can be used to express other influenza proteins such as influenza A H1, H2, H3, H4, H5, H6, H7, H8, H9, H10, H11, H12, H13, H14, H15, H16, H7N9, N1, N2, N3, N4, N5, N6, N7, N8, N9, influenza B hemagglutinin or neuraminidase protein whereby coding sequences for influenza A proteins H1, H2, H3, H4, H5, H6, H7, H8, H9, H10, H11, H12, H13, H14, H15, H16, H7N9, N1, N2, N3, N4, N5, N6, N7, N8, N9, influenza B hemagglutinin or neuraminidase protein are included in place of consensus hemagglutinin coding sequences.

5. Pharmaceutical Compositions

Provided herein are pharmaceutical compositions according to the present invention which comprise about 1 nanogram to about 10 mg of DNA. In some embodiments, pharmaceutical compositions according to the present invention comprise from between: 1) at least 10, 15, 20, 25, 30, 35, 40, 45, 50, 55, 60, 65, 70, 75, 80, 85, 90, 95 or 100 nanograms, or at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995 or 1000 micrograms, or at least 1.5, 2, 2.5, 3, 3.5, 4, 4.5, 5, 5.5, 6, 6.5, 7, 7.5, 8, 8.5, 9, 9.5 or 10 mg or more; and 2) up to and including 15, 20, 25, 30, 35, 40, 45, 50, 55, 60, 65, 70, 75, 80, 85, 90, 95 or 100 nanograms, or up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895. 900, 905, 910, 915, 920, 925, 930, 935, 940, 945, 950, 955, 960, 965, 970, 975, 980, 985, 990, 995, or 1000 micrograms, or up to and including 1.5, 2, 2.5, 3, 3.5, 4, 4.5, 5, 5.5, 6, 6.5, 7, 7.5, 8, 8.5, 9, 9.5 or 10 mg. In some embodiments, pharmaceutical compositions according to the present invention comprise about 5 nanogram to about 10 mg of DNA. In some embodiments, pharmaceutical compositions according to the present invention comprise about 25 nanogram to about 5 mg of DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

a. Vaccines

Preferably the pharmaceutical composition is a vaccine, and more preferably a DNA vaccine.

Provided herein is a vaccine capable of generating in a mammal an immune response against one or more influenza serotypes. The vaccine can comprise the genetic construct as discussed above. The vaccine can comprise a plurality of the vectors each directed to one or more Influenza A serotypes such as H7N9 or H1-H16 Influenza B hemagglutinin or combinations thereof. The vaccine can comprise one or more nucleic acid sequences that encode one or more consensus hemagglutinin antigens. When the vaccine comprises more than one consensus hemagglutinin nucleic acid sequences, all such sequences can be present on a single nucleic acid molecule or each such sequences can be present on a different nucleic acid molecule. Alternatively, vaccines that comprise more than one consensus hemagglutinin nucleic acid sequences can comprise nucleic acid molecules with a single consensus hemagglutinin nucleic acid sequences and nucleic acid molecules with more than one consensus hemagglutinin nucleic acid sequences. In addition, vaccines comprising one or more consensus hemagglutinin nucleic acid sequences can further comprise coding sequences for one or more proteins selected from the group consisting of H7N9, H1, H2, H3, H4, H5, H6, H7, H8, H9, H10, H11, H12, H13, H14, H15, H16, N1, N2, N3, N4, N5, N6, N7, N8, N9 and influenza B neuraminidase.

In some embodiments, vaccines can comprise proteins. Some vaccines can comprise one or more consensus hemagglutinin antigens such as H7N9, H1, H2, U2 and BHA. The vaccines can comprise one or more other proteins selected from the group consisting of H7N9, H1, H2, H3, H4, H5, H6, H7, H8, H9, H10, H11, H12, H13, H14, H15, H16, N1, N2, N3, N4, N5, N6, N7, N8, N9 and influenza B neuraminidase. The vaccines can comprise one or more consensus hemagglutinin antigens in combination with one or more other proteins selected from the group consisting of H7N9, H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase.

The vaccine can be a DNA vaccine. The DNA vaccine can comprise a plurality of the same or different plasmids comprising one or more of consensus hemagglutinin nucleic acid sequences. The DNA vaccine can comprise one or more nucleic acid sequences that encode one or more consensus hemagglutinin antigens. When the DNA vaccine comprises more than one consensus hemagglutinin nucleic acid sequences, all such sequences can be present on a single plasmid, or each such sequences can be present on a different plasmids, or some plasmids can comprise a single consensus hemagglutinin nucleic acid sequences while other plasmids have more than one consensus hemagglutinin nucleic acid sequences. In addition, DNA vaccines can further comprise one or more consensus coding sequences for one or more proteins selected from the group consisting of influenza A H7N9, H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase. Such additional coding sequences can be on the same or different plasmids from each other and from the plasmids comprising one or more of consensus hemagglutinin nucleic acid sequences.

In some embodiments, vaccines can comprise nucleic acid sequences that encode influenza antigens in combination with influenza antigens. In some embodiments, the nucleic acid sequences encode one or more consensus hemagglutinin antigens such as H7N9, H1 (including H1U and H1U2), H2, H3, and BHA. In some embodiments, the nucleic acid sequences encode one or more one or more other proteins selected from the group consisting of, influenza A H7N9, H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase. In some embodiments, the vaccines comprise one or more consensus hemagglutinin antigens such as H7N9, H1 (including H1U and H1U2), H2, H3, and BHA. In some embodiments, the vaccines comprise one or more one or more other proteins selected from the group consisting of influenza A H7N9, H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase.

In some embodiments, vaccines comprise a combination of four or more consensus hemagglutinin nucleic acid sequences including those encoding one or more of H7N9, H1 (including H1U and H1U2), H2, and BHA. In some embodiments, vaccines comprise a combination of four or more hemagglutinin nucleic acid sequences including those encoding consensus H7N9, H1U and/or H1U2, consensus BHA and an H3 hemagglutinin. In some embodiments, vaccines comprise a combination of four or more hemagglutinin nucleic acid sequences including those encoding consensus H7N9, BHA, an H1 hemagglutinin and an H3 hemagglutinin. In some embodiments, vaccines comprise one or more nucleic acid sequences that encode one or more influenza antigens disclosed in U.S. Ser. No. 12/375,518, which is incorporated herein by reference and/or U.S. Ser. No. 12/269,824, which is incorporated herein by reference. In some embodiments, vaccines comprise a nucleic acid sequence that encodes an H7N9 hemagglutinin (SEQ ID NO: 39). In some embodiments, vaccines comprise a nucleic acid sequence that encodes an H1 hemagglutinin from U.S. Ser. No. 12/375,518 (SEQ ID NO:36 therein) and/or U.S. Ser. No. 12/269,824 (SEQ ID NO:9 therein). In some embodiments, vaccines comprise a nucleic acid sequence that encodes an H3 hemagglutinin from U.S. Ser. No. 12/269,824 (SEQ ID NO:11 therein).

In some embodiments, vaccines comprise a combination of four or more consensus hemagglutinin proteins including one or more of H7N9, H1, H2, U2 and BHA. In some embodiments, vaccines comprise a combination of four or more hemagglutinin proteins including consensus H7N9, U2, consensus BHA and an H3 hemagglutinin. In some embodiments, vaccines comprise a combination of four or more hemagglutinin proteins including consensus H7N9, BHA, an H1 hemagglutinin and an H3 hemagglutinin. In some embodiments, vaccines comprise one or more antigens from U.S. Ser. No. 12/375,518 and/or U.S. Ser. No. 12/269,824. In some embodiments, vaccines comprise H7N9 hemagglutinin (SEQ ID NO: 40). In some embodiments, vaccines comprise an H1 hemagglutinin disclosed in U.S. Ser. No. 12/375,518 (SEQ ID NO:37 therein) and/or U.S. Ser. No. 12/269,824 (SEQ ID NO:10 therein). In some embodiments, vaccines comprise an H3 hemagglutinin disclosed in U.S. Ser. No. 12/269,824 (SEQ ID NO:12 therein).

In some embodiments, vaccines comprise a combination of 1) the consensus hemagglutinin H7N9 protein (SEQ ID NO: 40) and/or a nucleic acid sequences encoding the consensus hemagglutinin H7N9 protein (SEQ ID NO: 39), 2) the consensus hemagglutinin U2 protein and/or a nucleic acid sequences encoding the consensus hemagglutinin U2 protein, 3) the consensus hemagglutinin BHA protein and/or a nucleic acid sequences encoding the consensus hemagglutinin BHA protein, and 4) a hemagglutinin H3 protein disclosed in U.S. Ser. No. 12/269,824 (SEQ ID NO:12 therein) and/or a nucleic acid sequences encoding hemagglutinin H3 protein disclosed in U.S. Ser. No. 12/269,824 (SEQ ID NO:11 therein).

In some embodiments, vaccines comprise a combination of 1) the consensus hemagglutinin H7N9 protein (SEQ ID NO: 40) and/or a nucleic acid sequences encoding the consensus hemagglutinin H7N9 protein (SEQ ID NO: 39), 2) the consensus hemagglutinin BHA protein and/or a nucleic acid sequences encoding the consensus hemagglutinin BHA protein, 3) a hemagglutinin H1 protein disclosed in U.S. Ser. No. 12/269,824 (SEQ ID NO:10 therein) or U.S. Ser. No. 12/375,518 (SEQ ID NO:37 therein) and/or a nucleic acid sequences encoding hemagglutinin H1 protein disclosed in U.S. Ser. No. 12/269,824 (SEQ ID NO:9 therein) or U.S. Ser. No. 12/375,518 (SEQ ID NO:36 therein), and 4) a hemagglutinin H3 protein disclosed in U.S. Ser. No. 12/269,824 (SEQ ID NO:12 therein) and/or a nucleic acid sequences encoding hemagglutinin H3 protein disclosed in U.S. Ser. No. 12/269,824 (SEQ ID NO:11 therein).

Preferably, combinations of antigens provided herein can be formulated to a vaccine that causes seroconversion in vaccinated mammals that provide cross-reactivity against a broad range of seasonal strains of influenza and also pandemic strains of influenza. The seroconversion and broad cross-reactivity can be determined by measuring inhibiting titers against different hemagglutinin strains of influenza. Preferred combinations include at least one antigen from the following groups: 1) consensus H7N9 hemagglutinin; 2) consensus H1 hemagglutinin; 3) consensus H2 hemagglutinin; 4) consensus H3 hemagglutinin; and 5) influenza B hemagglutinin; and more preferred combinations include at least one antigen from the following groups: 1) consensus H7N9 hemagglutinin; 2) consensus H1 hemagglutinin; 3) consensus H3 hemagglutinin; and 4) influenza B hemagglutinin.

In some embodiments the vaccines can have a combination as such:

a) one or more of a first influenza nucleic acid sequence H7N9 hemagglutinin capable of generating broadly cross reactive immune response in mammals against multiple strains of influenza virus, which is/are selected from the following:

a nucleic acid sequence selected from the group consisting of: SEQ ID NO: 39, a nucleic acid sequence that is 95% identical over the entire length of the nucleic acid sequence of SEQ ID NO: 39; a fragment of SEQ ID NO: 39; a nucleic acid sequence that is 95% identical to a fragment of SEQ ID NO: 39; nucleic acid sequences encoding SEQ ID NO:40, a nucleic acid sequence that is 95% identical over the entire length of the nucleic acid sequence encoding SEQ ID NO: 40; a fragment of nucleic acid sequences encoding SEQ ID NO: 40; and a nucleic acid sequence that is 95% identical to a fragment of nucleic acid sequences encoding SEQ ID NO: 40.

b) one or more of a first influenza nucleic acid sequence H1 hemagglutinin capable of generating broadly cross reactive immune response in mammals against multiple strains of influenza virus, which is/are selected from the following: a nucleic acid sequence selected from the group consisting of: SEQ ID NO:1, a nucleic acid sequence that is 95% identical over the entire length of the nucleic acid sequence of SEQ ID NO:1; a fragment of SEQ ID NO:1; a nucleic acid sequence that is 95% identical to a fragment of SEQ ID NO:1; SEQ ID NO:9, a nucleic acid sequence that is 95% identical over the entire length of the nucleic acid sequence of SEQ ID NO:9; a fragment of SEQ ID NO:9; a nucleic acid sequence that is 95% identical to a fragment of SEQ ID NO:9; SEQ ID NO:19; a nucleic acid sequence that is 95% identical over the entire length of the nucleic acid sequence of SEQ ID NO:19; a fragment of SEQ ID NO:19; a nucleic acid sequence that is 95% identical to a fragment of SEQ ID NO:19; SEQ ID NO:21; a nucleic acid sequence that is 95% identical over the entire length of the nucleic acid sequence of SEQ ID NO:21; a fragment of SEQ ID NO:21; a nucleic acid sequence that is 95% identical to a fragment of SEQ ID NO:21; SEQ ID NO:35; a nucleic acid sequence that is 95% identical over the entire length of the nucleic acid sequence of SEQ ID NO:35; a fragment of SEQ ID NO:35; a nucleic acid sequence that is 95% identical to a fragment of SEQ ID NO:35; nucleic acid sequences encoding SEQ ID NO:2, a nucleic acid sequence that is 95% identical over the entire length of the nucleic acid sequence encoding SEQ ID NO:2; a fragment of nucleic acid sequences encoding SEQ ID NO:2; a nucleic acid sequence that is 95% identical over the entire length of the nucleic acid sequence of a fragment of nucleic acid sequences encoding SEQ ID NO:2; nucleic acid sequences encoding SEQ ID NO:10, a nucleic acid sequence that is 95% identical over the entire length of the nucleic acid sequence encoding SEQ ID NO:10; a fragment of nucleic acid sequences encoding SEQ ID NO:10; a nucleic acid sequence that is 95% identical to a fragment of nucleic acid sequences encoding SEQ ID NO:10; nucleic acid sequences encoding SEQ ID NO:20; a nucleic acid sequence that is 95% identical over the entire length of the nucleic acid sequence encoding SEQ ID NO:20; a fragment of nucleic acid sequences encoding SEQ ID NO:20; a nucleic acid sequence that is 95% identical to a fragment of nucleic acid sequences encoding SEQ ID NO:20; nucleic acid sequences encoding SEQ ID NO:22; a nucleic acid sequence that is 95% identical over the entire length of the nucleic acid sequence encoding SEQ ID NO:22; a fragment of nucleic acid sequences encoding SEQ ID NO:22; a nucleic acid sequence that is 95% identical to a fragment of nucleic acid sequences encoding SEQ ID NO:22; nucleic acid sequences encoding SEQ ID NO:36; a nucleic acid sequence that is 95% identical over the entire length of the nucleic acid sequence encoding SEQ ID NO:36; a fragment of nucleic acid sequences encoding SEQ ID NO:36; and a nucleic acid sequence that is 95% identical to a fragment of nucleic acid sequences encoding SEQ ID NO:36.

c) one or more of a first influenza nucleic acid sequence H3 hemagglutinin capable of generating broadly cross reactive immune response in mammals against multiple strains of influenza virus, which is/are selected from the following: a nucleic acid sequence selected from the group consisting of: SEQ ID NO:23, a nucleic acid sequence that is 95% identical over the entire length of the nucleic acid sequence of SEQ ID NO:23; a fragment of SEQ ID NO:23; a nucleic acid sequence that is 95% identical to a fragment of SEQ ID NO:23; SEQ ID NO:27, a nucleic acid sequence that is 95% identical over the entire length of the nucleic acid sequence of SEQ ID NO:27; a fragment of SEQ ID NO:27; a nucleic acid sequence that is 95% identical to a fragment of SEQ ID NO:27; SEQ ID NO:29; a nucleic acid sequence that is 95% identical over the entire length of the nucleic acid sequence of SEQ ID NO:29; a fragment of SEQ ID NO:29; a nucleic acid sequence that is 95% identical to a fragment of SEQ ID NO:29; SEQ ID NO:37; a nucleic acid sequence that is 95% identical over the entire length of the nucleic acid sequence of SEQ ID NO:37; a fragment of SEQ ID NO:37; a nucleic acid sequence that is 95% identical to a fragment of SEQ ID NO:37; nucleic acid sequences encoding SEQ ID NO:24, a nucleic acid sequence that is 95% identical over the entire length of the nucleic acid sequence encoding SEQ ID NO:24; a fragment of nucleic acid sequences encoding SEQ ID NO:24; a nucleic acid sequence that is 95% identical to a fragment of nucleic acid sequences encoding SEQ ID NO:24; nucleic acid sequences encoding SEQ ID NO:28; a nucleic acid sequence that is 95% identical over the entire length of the nucleic acid sequence encoding SEQ ID NO: 28; a fragment of nucleic acid sequences encoding SEQ ID NO: 28; a nucleic acid sequence that is 95% identical to a fragment of nucleic acid sequences encoding SEQ ID NO: 28; nucleic acid sequences encoding SEQ ID NO:30; a nucleic acid sequence that is 95% identical over the entire length of the nucleic acid sequence encoding SEQ ID NO: 30; a fragment of nucleic acid sequences encoding SEQ ID NO: 30; a nucleic acid sequence that is 95% identical to a fragment of nucleic acid sequences encoding SEQ ID NO: 30; nucleic acid sequences encoding SEQ ID NO:38; a nucleic acid sequence that is 95% identical over the entire length of the nucleic acid sequence encoding SEQ ID NO: 38; a fragment of nucleic acid sequences encoding SEQ ID NO: 38; and a nucleic acid sequence that is 95% identical to a fragment of nucleic acid sequences encoding SEQ ID NO: 38.

d) one or more of a first influenza nucleic acid sequence influenza B hemagglutinin capable of generating broadly cross reactive immune response in mammals against multiple strains of influenza virus, which is/are selected from the following:
a nucleic acid sequence selected from the group consisting of: SEQ ID NO:13, a nucleic acid sequence that is 95% identical over the entire length of the nucleic acid sequence of SEQ ID NO: 13; a fragment of SEQ ID NO: 13; a nucleic acid sequence that is 95% identical to a fragment of SEQ ID NO: 13; SEQ ID NO:25, a nucleic acid sequence that is 95% identical over the entire length of the nucleic acid sequence of SEQ ID NO: 25; a fragment of SEQ ID NO: 25; a nucleic acid sequence that is 95% identical to a fragment of SEQ ID NO: 25; SEQ ID NO:31; a nucleic acid sequence that is 95% identical over the entire length of the nucleic acid sequence of SEQ ID NO: 31; a fragment of SEQ ID NO: 31; a nucleic acid sequence that is 95% identical to a fragment of SEQ ID NO: 31; SEQ ID NO:33; a nucleic acid sequence that is 95% identical over the entire length of the nucleic acid sequence of SEQ ID NO: 33; a fragment of SEQ ID NO: 33; a nucleic acid sequence that is 95% identical to a fragment of SEQ ID NO: 33; nucleic acid sequences encoding SEQ ID NO:14, a nucleic acid sequence that is 95% identical over the entire length of the nucleic acid sequence encoding SEQ ID NO: 14; a fragment of nucleic acid sequences encoding SEQ ID NO: 14; a nucleic acid sequence that is 95% identical to a fragment of nucleic acid sequences encoding SEQ ID NO: 14; nucleic acid sequences encoding SEQ ID NO:26; a nucleic acid sequence that is 95% identical over the entire length of the nucleic acid sequence encoding SEQ ID NO: 26; a fragment of nucleic acid sequences encoding SEQ ID NO: 26; a nucleic acid sequence that is 95% identical to a fragment of nucleic acid sequences encoding SEQ ID NO: 26; nucleic acid sequences encoding SEQ ID NO:32; a nucleic acid sequence that is 95% identical over the entire length of the nucleic acid sequence encoding SEQ ID NO: 32; a fragment of nucleic acid sequences encoding SEQ ID NO: 32; a nucleic acid sequence that is 95% identical to a fragment of nucleic acid sequences encoding SEQ ID NO: 32; nucleic acid sequences encoding SEQ ID NO:34; a nucleic acid sequence that is 95% identical over the entire length of the nucleic acid sequence encoding SEQ ID NO: 34; a fragment of nucleic acid sequences encoding SEQ ID NO: 34; and a nucleic acid sequence that is 95% identical to a fragment of nucleic acid sequences encoding SEQ ID NO: 34.

In some embodiments, in addition to a), b), c), and d), above, the combination can also include one or more of a an influenza nucleic acid sequence H2 hemagglutinin capable of generating broadly cross reactive immune response in mammals against multiple strains of influenza virus, which is/are selected from the following: SEQ ID NO:6, a nucleic acid sequence that is 95% identical over the entire length of the nucleic acid sequence of SEQ ID NO: 6; a fragment of SEQ ID NO: 6; a nucleic acid sequence that is 95% identical to a fragment of SEQ ID NO: 6; nucleic acid sequences encoding SEQ ID NO:7; a nucleic acid sequence that is 95% identical over the entire length of the nucleic acid sequence encoding SEQ ID NO: 7; a fragment of nucleic acid sequences encoding SEQ ID NO: 7; and a nucleic acid sequence that is 95% identical to a fragment of nucleic acid sequences encoding SEQ ID NO: 7.

DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome. The vaccine can be an RNA of the hemagglutinin antigen. The RNA vaccine can be introduced into the cell.

The vaccine can be a recombinant vaccine comprising the genetic construct or antigen described above. The vaccine can also comprise one or more consensus hemagglutinin antigen in the form of one or more protein subunits, one or more killed influenza particles comprising one or more consensus hemagglutinin antigens, or one or more attenuated influenza particles comprising one or more consensus hemagglutinin antigens. The attenuated vaccine can be attenuated live vaccines, killed vaccines and vaccines that use recombinant vectors to deliver foreign genes that encode one or more consensus hemagglutinin antigens, and well as subunit and glycoprotein vaccines. Examples of attenuated live vaccines, those using recombinant vectors to deliver foreign antigens, subunit vaccines and glycoprotein vaccines are described in U.S. Pat. Nos. 4,510,245; 4,797,368; 4,722, 848; 4,790,987; 4,920,209; 5,017,487; 5,077,044; 5,110, 587; 5,112,749; 5,174,993; 5,223,424; 5,225,336; 5,240, 703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

The vaccine can comprise vectors and/or proteins directed to Influenza A serotypes from particular regions in the world, for example, Asia. The vaccine can also be directed against Influenza A serotypes of swine or avian origin that now infect humans. The vaccine can comprise vectors and/or proteins directed to Influenza B from particular regions in the world. The vaccine can also be directed against Influenza B that infect humans. The vaccine can comprise one or more vectors and/or one or more proteins directed to one or more strains of Influenza A and/or B.

The vaccine provided can be used to induce immune responses including therapeutic or prophylactic immune responses. Antibodies and/or killer T cells can be generated which are directed to the consensus hemagglutinin antigen, and also broadly across multiple subtypes of influenza viruses. Such antibodies and cells can be isolated.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are delivered as proteins in combination with the plasmid above in the vaccine. The adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof.

Other genes which can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The vaccine can further comprise a genetic vaccine facilitator agent as described in U.S. Ser. No. 021,579 filed Apr. 1, 1994, which is fully incorporated by reference.

6. Methods of Delivery

Provided herein is a method for delivering the pharmaceutical formulations, preferably vaccines, for providing genetic constructs and proteins of the hemagglutinin antigen which comprise epitopes that make them particular effective immunogens against which an immune response to influenza viral infections can be induced. The method of delivering the vaccine, or vaccination, can be provided to induce a therapeutic and/or prophylactic immune response. The vaccination process can generate in the mammal an immune response against a plurality of influenza subtypes, including a H1N1 serotype, such as the 2009 swine originated H1N1 or avian H7N9, or other seasonal and/or pandemic varieties. The vaccine can be delivered to an individual to modulate the activity of the mammal's immune system and enhance the immune response. The delivery of the vaccine can be the transfection of the HA antigen as a nucleic acid molecule that is expressed in the cell and delivered to the surface of the cell upon which the immune system recognized and induces a cellular, humoral, or cellular and humoral response. The delivery of the vaccine can be used to induce or elicit and immune response in mammals against a plurality of influenza viruses by administering to the mammals the vaccine as discussed herein.

Upon delivery of the vaccine to the mammal, and thereupon the vector into the cells of the mammal, the transfected cells will express and secrete the corresponding influenza protein, including at least one of the consensus antigens, and preferably H7N9, H1, H2, U2, and BHA. These secreted proteins, or synthetic antigens, will be recognized as foreign by the immune system, which will mount an immune response that can include: antibodies made against the antigens, and T-cell response specifically against the antigen. In some examples, a mammal vaccinated with the vaccines discussed herein will have a primed immune system and when challenged with an influenza viral strain, the primed immune system will allow for rapid clearing of subsequent influenza viruses, whether through the humoral, cellular, or both. The vaccine can be delivered to an individual to modulate the activity of the individual's immune system thereby enhancing the immune response.

The vaccine can be delivered in the form of a DNA vaccine and methods of delivering a DNA vaccines are described in U.S. Pat. Nos. 4,945,050 and 5,036,006, which are both incorporated fully by reference.

The vaccine can be administered to a mammal to elicit an immune response in a mammal. The mammal can be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

a. Combination with Other Antigens and Adjuvants

The pharmaceutical compositions, preferably vaccines, described herein can be administered in combination with one or more other influenza proteins or genes encoding influenza A H7N9, H1, H2, H3, H4, H5, H6, H7, H8, H9, H10, H11, H12, H13, H14, H15, H16, N1, N2, N3, N4, N5, N6, N7, N8, N9, influenza B hemagglutinin and neuraminidase. The vaccine can be administered in combination with proteins or genes encoding adjuvants, which can include: α-interferon (IFN-α), β-interferon (IFN-β), γ-interferon, IL-12, IL-15, IL-21, IL-23, IL-28, IL-33, CTACK, TECK, platelet derived growth factor (PDGF), TNFα, TNFβ, GM-CSF, epidermal growth factor (EGF), IL-1, IL-2, IL-4, IL-5, IL-6, IL-10, IL-18, MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, or TAP2, or functional fragments thereof.

b. Routes of Administration

The vaccine can be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition can be administered as a suitably acceptable formulation in accordance with normal veterinary practice. The veterinarian can readily determine the dosing regimen and route of administration that is most appropriate for a particular animal. The vaccine can be administered by traditional syringes, needleless injection devices, "microprojectile bombardment gone guns", or other physical methods such as electroporation ("EP"), "hydrodynamic method", or ultrasound.

The vector of the vaccine can be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The HA antigen can be delivered via DNA injection and along with in vivo electroporation.

c. Electroporation

Administration of the vaccine via electroporation of the plasmids of the vaccine can be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device can comprise an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (VGX Pharmaceuticals, Blue Bell, Pa.) or Elgen electroporator (Genetronics, San Diego, Calif.) to facilitate transfection of cells by the plasmid.

The electroporation component can function as one element of the electroporation devices, and the other elements are separate elements (or components) in communication with the electroporation component. The electroporation component can function as more than one element of the electroporation devices, which can be in communication with still other elements of the electroporation devices separate from the electroporation component. The elements of the electroporation devices existing as parts of one electromechanical or mechanical device can not limited as the elements can function as one device or as separate elements in communication with one another. The electroporation component can be capable of delivering the pulse of energy that produces the constant current in the desired tissue, and includes a feedback mechanism. The electrode assembly can include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

A plurality of electrodes can deliver the pulse of energy in a decentralized pattern. The plurality of electrodes can deliver the pulse of energy in the decentralized pattern through the control of the electrodes under a programmed sequence, and the programmed sequence is input by a user to the electroporation component. The programmed sequence can comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism can be performed by either hardware or software. The feedback mechanism can be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode can measure the impedance in the desired tissue and communicates the impedance to the feedback mechanism, and the feedback mechanism responds to the impedance and adjusts the pulse of energy to maintain the constant current at a value similar to the preset current. The feedback mechanism can maintain the constant current continuously and instantaneously during the delivery of the pulse of energy.

Examples of electroporation devices and electroporation methods that can facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that can be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems can comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which can be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 can be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes. The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

d. Method of Preparing Vaccine

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on Can 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1 pGX2009 (pH1HA09)—Plasmid Encoding 2009 H1N1 Influenza (Swine Flu) Hemagglutinin Antigen The backbone of pGX2009 (H1HA09) is the modified expression vector pVAX1 (Invitrogen, Carlsbad, Calif.) under the control of the cytomegalovirus immediate-early (CMV) promoter. The original pVAX1 was purchased from Invitrogen (Catalog number V260-20) and maintained at −20° C. As noted above, sequence analysis revealed differences between the sequence of pVAX1 used as the backbone of pGX2009 and the pVAX1 sequence available from Invitrogen. The differences are set forth above.

Plasmid pGX2009, also referred to as pH1HA09, comprises a nucleic acid sequence that encodes a consensus 2009 H1N1 influenza (swine flu) hemagglutinin molecule. The 79 primary sequences used to generate the consensus sequence were selected from The Influenza Sequence Database.

The accession numbers for nucleotide sequences encoding the amino acid sequence for the various influenza A hemagglutinin H1 proteins as well as the amino acid sequences encoded by the nucleotide sequences are in the GenBank database corresponding to the following accession numbers. The accession numbers not in parentheses disclose nucleotide sequences and additional list amino acid sequences encoded by them. The accession numbers in parentheses are for entries of the corresponding amino acid sequence in GenBank's protein database.
The accession numbers are as follows: GQ323579.1 (ACS72657.1), GQ323564.1 (ACS72654.1), GQ323551.1 (ACS72652.1), GQ323530.1 (ACS72651.1), GQ323520.1 (ACS72650.1), GQ323495.1 (ACS72648.1), GQ323489.1 (ACS72647.1), GQ323486.1 (ACS72646.1), GQ323483.1 (ACS72645.1), GQ323455.1 (ACS72641.1), GQ323451.1 (ACS72640.1), GQ323443.1 (ACS72638.1), GQ293077.1 (ACS68822.1), GQ288372.1 (ACS54301.1), GQ287625.1 (ACS54262.1), GQ287627.1 (ACS54263.1), GQ287623.1 (ACS54261.1), GQ287621.1 (ACS54260.1), GQ286175.1 (ACS54258.1), GQ283488.1 (ACS50088.1), GQ280797.1 (ACS45035.1), GQ280624.1 (ACS45017.1), GQ280121.1 (ACS45189.1), GQ261277.1 (ACS34968.1), GQ253498.1 (ACS27787.1), GQ323470.1 (ACS72643.1), GQ253492.1 (ACS27780.1), FJ981613.1 (ACQ55359.1), FJ971076.1 (ACP52565.1), FJ969540.1 (ACP44189.1), FJ969511.1 (ACP44150.1), FJ969509.1 (ACP44147.1), GQ255900.1 (ACS27774.1), GQ255901.1 (ACS27775.1), FJ966974.1 (ACP41953.1), GQ261275.1 (ACS34967.1), FJ966960.1 (ACP41935.1), FJ966952.1 (ACP41926.1), FJ966082.1 (ACP41105.1), GQ255897.1 (ACS27770.1), CY041645.1 (ACS27249.1), CY041637.1 (ACS27239.1), CY041629 (ACS27229.1), GQ323446.1 (ACS72639.1), CY041597.1 (ACS27189.1), CY041581.1 (ACS14726.1), CY040653.1 (ACS14666.1), CY041573.1 (ACS14716.1), CY041565.1 (ACS14706.1), CY041541.1 (ACS14676.1), GQ258462.1 (ACS34667.1), CY041557.1 (ACS14696.1), CY041549.1 (ACS14686.1), GQ283484.1 (ACS50084.1), GQ283493.1 (ACS50095.1), GQ303340.1 (ACS71656.1), GQ287619.1 (ACS54259.1), GQ267839.1 (ACS36632.1), GQ268003.1 (ACS36645.1), CY041621.1 (ACS27219.1), CY041613.1 (ACS27209.1), CY041605.1 (ACS27199.1), FJ966959.1 (ACP41934.1), FJ966982.1 (ACP41963.1), CY039527.2 (ACQ45338.1), FJ981612.1 (ACQ55358.1), FJ981615.1 (ACQ55361.1), FJ982430.1 (ACQ59195.1), FJ998208.1 (ACQ73386.1), GQ259909.1 (ACS34705.1), GQ261272.1 (ACS34966.1), GQ287621.1 (ACS54260.1), GQ290059.1 (ACS66821.1), GQ323464.1 (ACS72642.1), GQ323473.1 (ACS72644.1), GQ323509.1 (ACS72649.1), GQ323560.1 (ACS72653.1), GQ323574.1 (ACS72655.1), and GQ323576.1 (ACS72656.1). The amino acid sequences were downloaded from the NCBI Sequence Database, and an alignment and consensus sequence generated using Clustal X. A highly efficient leader sequence, the IgE leader, was fused in frame upstream of the start codon to facilitate the expression. In order to have a higher level of expression, the codon usage of this fusion gene was adapted to the codon bias of *Homo sapiens* genes. In addition, RNA optimization was also performed: regions of very high (>80%) or very low (<30%) GC content and the cis-acting sequence motifs such as internal TATA boxes, chi-sites and ribosomal entry sites were avoided. The entire sequence was synthetically produced at Geneart (Regensburg, Germany). The synthetic engineered H1HA09 gene was 1818 bp in length (SEQ ID NO:1) and was cloned into pVAX1 at BamHI and XhoI sites by Geneart (FIG. 2).

Example 2

HS09 Influenza (pGX2009) Immunized Ferrets

Experiments were carried out using ferrets, a preferred model for influenza. The ferrets were immunized using plasmid pGX2009 (SEQ ID NO:5, including insert HS09 (SEQ ID NO:1)).

Animals: 4 groups×5 animals/group, plus one control group with 4 animals=24 ferrets total (male)

Duration: 18 weeks (including challenge)

Dose: 0.2 mg plasmid

Protocol Summary: Ferrets were allocated randomly into DNA vaccine groups. Animals were immunized at Study Day 0, Day 28, and Day 56. Animals were anesthetized with ketamine/midazolam cocktail, isoflurane or equivalent according to approved anesthesia protocols and vaccinated IM with influenza DNA vaccine combinations. Groups 1 and 2 were immediately electroporated using CELLECTRA® adaptive constant current electroporation (EP) device at 0.5 Amp, 52 millisecond pulses, 0.2 sec between pulses, 4 sec firing delay, 3 total pulses. Control animals were naïve controls (no plasmid, no EP). Ferrets were allowed to recover from anesthesia in their cages and were closely monitored for 24 hours to ensure full recovery.

Food and water was available ad libitum for the length of the study. On Day 84, animals were challenged by intranasal infection with 1 ml of MX10 (A/Mexico/InDRE4487/2009; 5×105 PFU/ml). Animals were monitored daily for clinical signs (weight, temperature, etc.), using an established and approved scoring sheet. On 1, 3, 6, 9 and 15 dpi nasal washes and rectal swabs were collected. Lungs were collected at day 15. Samples were stored in RNAlater for virus load by real-time PCR, medium for infectious virus (TCDI50) and formalin for histology when appropriated.

HAI Titers

The ferrets were bled and sera samples immediately stored on dry-ice before being shipped to BIOQUAL, Rockville, Md. for processing. Sera was treated with receptor-destroying enzyme by diluting 1 part serum with 3 parts enzyme and were incubated overnight at 37° C. water bath. The enzyme was inactivated by 30-min incubation at 56° C., followed by the addition of 6 parts phosphate-buffered saline for a final dilution of 1/10. HAI assays were performed in V-bottomed 96-well microtiter plates, using 4 hemagglutination units of virus and 1% red blood cells. Virus (H1N1/Mexico/InDRE4487/2009 strain) used for the HAI assays are obtained from the influenza branch of the CDC. FIG. 4 shows a Hemagglutination Inhibition assay performed with sera from immunized ferrets (3 immunizations). A titer of >1:40 is considered "protective". A dotted line indicates the 1:40 mark. All animals were above the 1:40 mark after 3 immunizations.

Challenge Studies

FIG. 5 shows results of a challenge of immunized and unimmunized ferrets with a novel H1N1 strain MX10 (A/Mexico/InDRE4487/2009). All immunized ferrets survived, while 75% of the naive ferrets died within the 15 day period.

Example 3

H1 Hemagglutin Combination Studies

Experiments were carried out using various animals (mouse, guinea pigs and ferrets). The animals were immunized using plasmid constructs with backbone pVAX1, with each construct having a different insert:
In FIGS. 7A-G, 8A-C, 9A-B, 10A-B, 11A-C: naive (pVAX1 only); H1U1 (pVAX1 with SEQ ID NO:35 insert); HS09 (SEQ ID NO:5); ConBris (or H1Bris) (pVAX1 with SEQ ID NO:19 insert); ConTT (or H1TT) (pVAX1 with SEQ ID NO:21 insert);
In FIGS. 13A-F, 14A-C, 15A-D, 16A-C, 17A-C: naive (pVAX1 only); BHA-1 (pVAX1 with SEQ ID NO:13 insert); BHA-2 (pVAX1 with SEQ ID NO:25 insert); BHA-3 (pVAX1 with SEQ ID NO:31 insert); BHA-4 (pVAX1 with SEQ ID NO:33 insert).
In FIGS. 19A-E, 20A-F: naive (pVAX1 only); H3HA-1 (pVAX1 with SEQ ID NO:37 insert); H3HA-2 (pVAX1 with SEQ ID NO:23 insert); H3HA-3 (pVAX1 with SEQ ID NO:27 insert); H3HA-4 (pVAX1 with SEQ ID NO:29 insert).

Dose: 0.2 mg Plasmid

Protocol Summary: animals were allocated randomly into DNA vaccine groups. Animals were immunized at Study Day 0, Day 28, and Day 56. Animals were anesthetized with ketamine/midazolam cocktail, isoflurane or equivalent according to approved anesthesia protocols and vaccinated IM with influenza DNA vaccine combinations. Groups 1 and 2 were immediately electroporated using CELLECTRA adaptive constant current electroporation (EP) device (Inovio Pharmaceuticals, Blue Bell, Pa.) at 0.5 Amp, 52 millisecond pulses, 0.2 sec between pulses, 4 sec firing delay, 3 total pulses. Control animals were naïve controls (no plasmid, no EP). The animals were allowed to recover from anesthesia in their cages and were closely monitored for 24 hours to ensure full recovery.

HAI Assays

Animals were bled and sera samples immediately stored on dry-ice before being shipped to BIOQUAL, Rockville, Md. for processing. Sera was treated with receptor-destroying enzyme by diluting 1 part serum with 3 parts enzyme and were incubated overnight at 37° C. water bath. The enzyme was inactivated by 30-min incubation at 56° C., followed by the addition of 6 parts phosphate-buffered saline for a final dilution of 1/10. HAI assays were performed in V-bottomed 96-well microtiter plates, using 4 hemagglutination units of virus and 1% red blood cells. Virus (H1N1/Mexico/2009 strain) used for the HAI assays are obtained from the influenza branch of the CDC.

H1 Studies:

The experiments showed that mice vaccinated with the combo (all four H1 antigens) showed protective titers against 9 out of 10 strains (FIG. 7A-7F, and FIG. 8A-C). This shows robust cross-reactivity across strains. Similarly the experiments showed that guinea pigs with the combo showed protective titers against all 10 strains (see FIGS. 9A-B and 10A-B).

Figure 13:
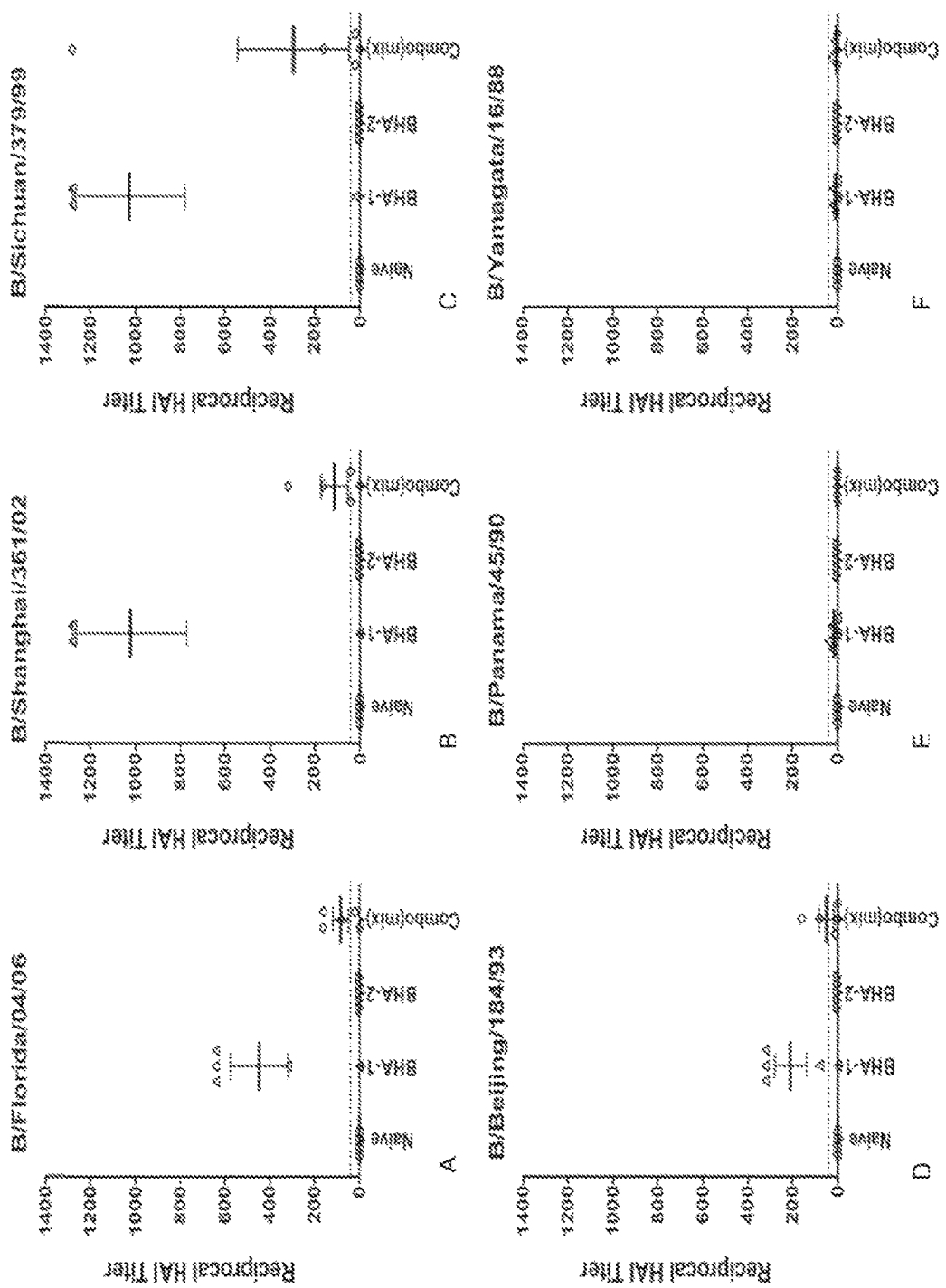

Flu B Studies:

The experiments showed that mice vaccinated with the combo (both BHA-1 and BHA-2 antigens) showed protective titers against 4 out of 9 strains (FIG. 13A-13C, and FIG. 14C); while 2 strains showed borderline 1:40 (FIG. 13D and FIG. 14A). The individual antigens showed protective titers against 4 of 9 strains (BHA-1) and 3 out of 9 strains (BHA-2). Similarly the experiments showed that guinea pigs with the combo showed protective titers against all 10 strains (see FIGS. 9A-B and 10A-B).

The experiments showed that guinea pigs vaccinated with the combo (both BHA-1 and BHA-2 antigens) showed protective titers against all 10 of 10 strains (looking at post-dose 3 "PD3"). Whereas, on the other hand, immunization with single antigens did not provide such cross-protection, with BHA-1 providing only protective titers against 7 of 10 strains (FIG. 15A-D and FIG. 16A-C).

Figure 19:
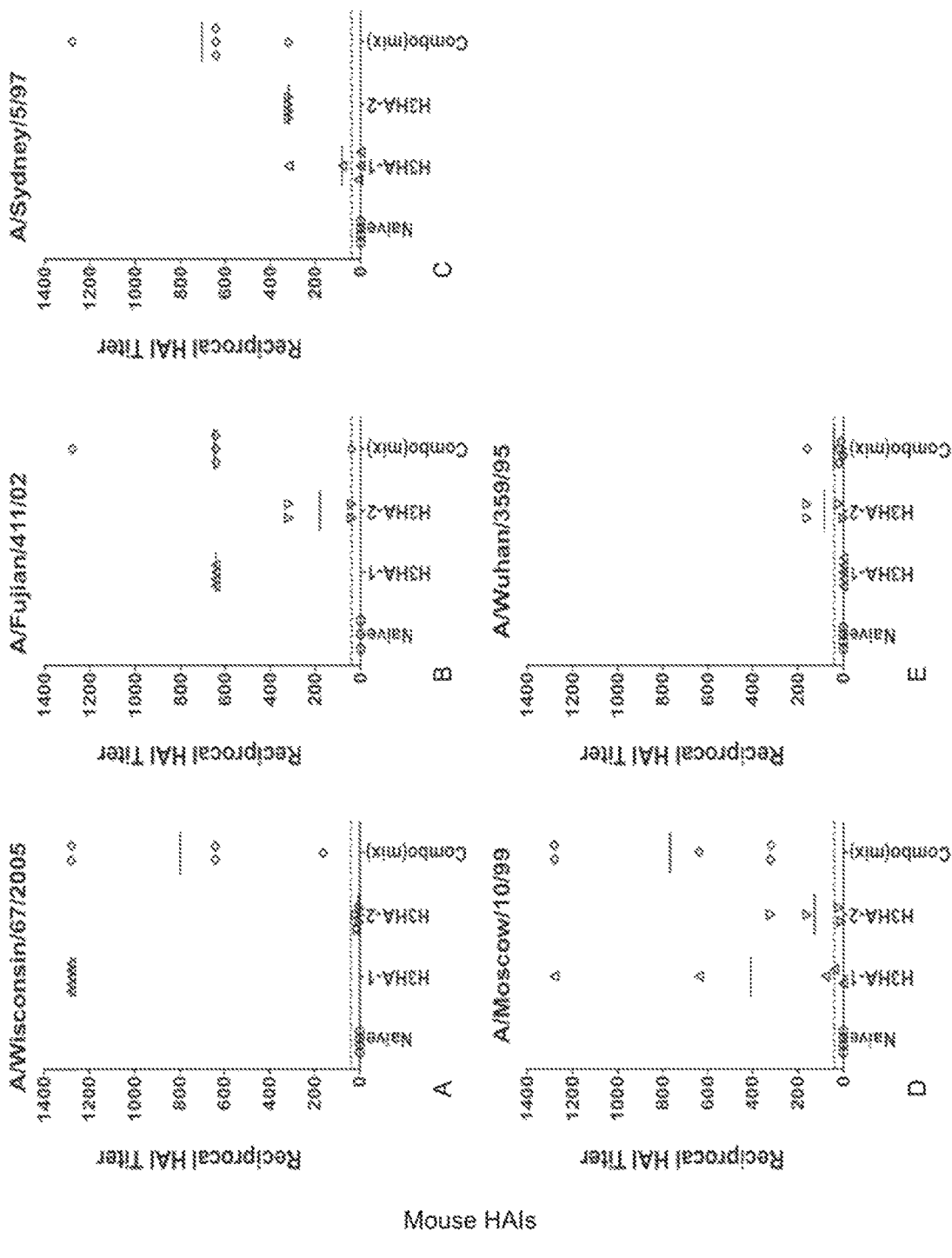
Figure 20:
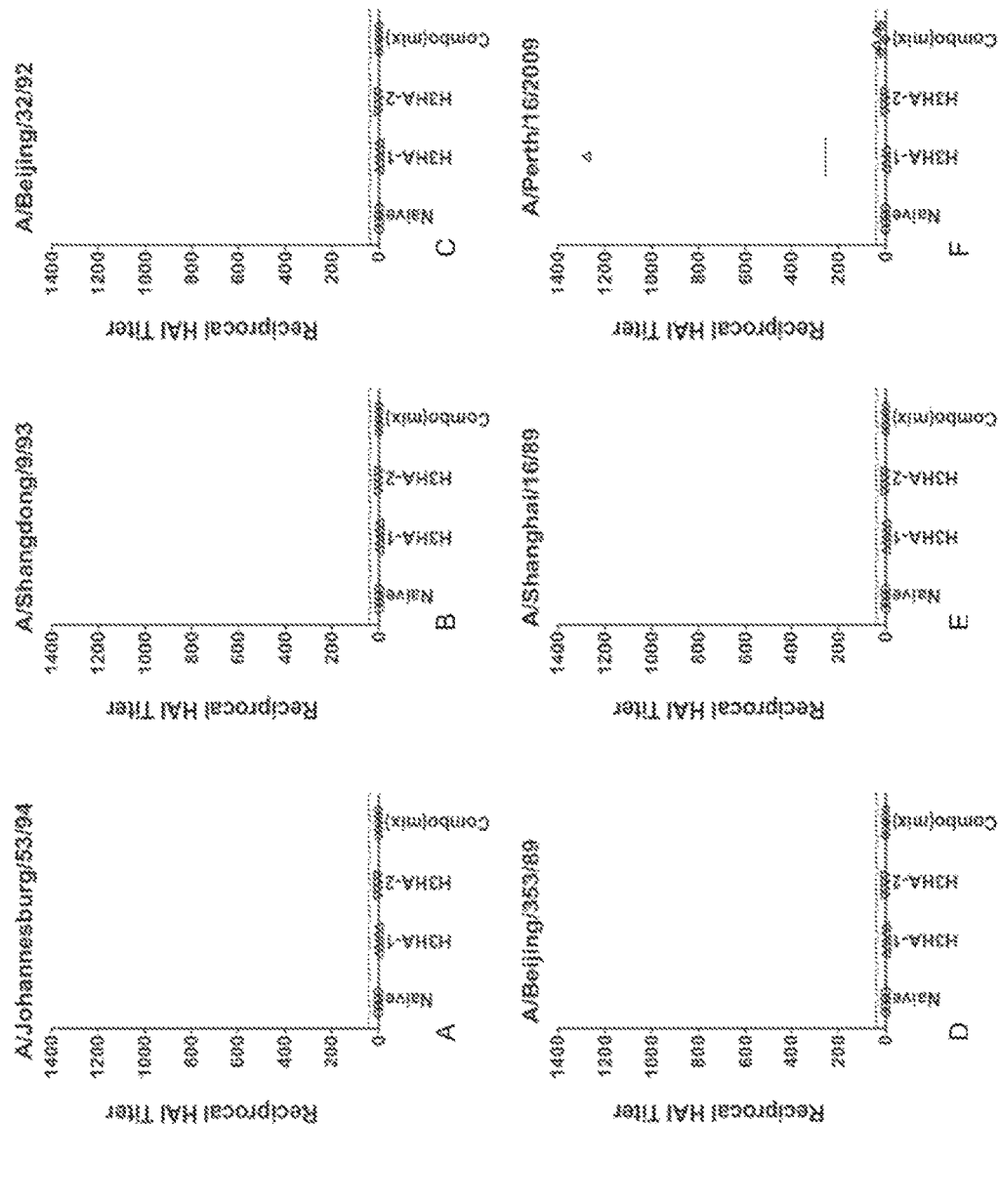

H3 Studies:

The experiments showed that mice vaccinated with the combo (both H3HA-1 and H3HA-2 antigens) showed protective titers against 4 of 11 strains (FIG. 19A-D), and near protective titers against 2 strains (FIG. 19E and FIG. 20F). Whereas, on the other hand, the single antigens display cross-protection against 4 of 11 strains in the case of H3HA-1 (FIG. 19A-D) but no HAI titer exhibited in any of the remaining strains. The combo H3 mix showed slightly broader cross-protection than one H3 antigen alone.

Challenge Studies

Food and water was available ad libitum for the length of the study. On Day 84, ferrets were challenged by intranasal infection with 1 ml of MX10 (A/Mexico/2009; 5×105 PFU/ml). Animals were monitored daily for clinical signs (weight, temperature, etc.), using an established and approved scoring sheet. On 1, 3, 6, 9 and 15 dpi nasal washes and rectal swabs were collected. Lungs were collected at day 15. Samples were stored in RNAlater for virus load by real-time PCR, medium for infectious virus (TCDI50) and formalin for histology when appropriated.

H1HA Vaccinated—Challenge

The ferrets vaccinated with HS09 and H1U showed immunoprotection as all five ferrets survive 14 days post-infection; whereas only one out of five naive survived. See FIGS. 11A-C.

Example 4

Influenza H7N9 Hemagglutinin DNA Vaccine Design

To design a H7N9 hemagglutinin DNA vaccine, the hemagglutinin (HA) sequences of the first four identified H7N9 human isolates were retrieved from The Global Initiative on Sharing All Influenza Data (GISAID). All HA sequences were aligned using MegAlign (DNASTAR, Madison, Wis.) and a consensus HA sequence (H7HA) was developed, codon/RNA optimized and subsequently synthesized by GenScript. The H7N9 HA consensus sequence (SEQ ID NO: 40) was generated from the first four H7N9 HA sequences.

After generating the consensus HA sequence, codon and RNA optimizations were performed, as previously described (Yan et al., (2007) Mol Ther 15: 411). In just a few days, the synthetic H7HA gene (SEQ ID NO: 39), which is 1683 bp in length, was synthesized, sequence verified, and subcloned into the expression vector pGX0001 at BamHI and NotI sites and named pH7HA (FIG. 21B). The expression vector pGX0001 is under the control of the cytomegalovirus immediate-early promoter.

Example 5

Phylogenetic Analysis of H7N9 HA Protein Sequences

Twenty-four primary HA protein sequences of human H7N9 virus isolates were retrieved from GISAID. The alignment applied in the phylogenetic study was performed using Clustal X (version 2.0) and a phylogenetic tree was constructed based on Neighbor-joining evaluation of the alignment. Phylogenetic analysis indicated that the sequence identity between any two H7 HA proteins of these human isolates could be as low as 95.9%, while the identities between the consensus HA and primary HA proteins were 97.5% and above. The consensus approach to antigen development for influenza was not dependent upon any one viral isolate that can not represent the totality of the pandemic in real time. The relevant placement of the consensus H7 HA sequence is indicated in FIG. 21A.

Example 6

Expression of pH7HA DNA Vaccine

To determine the expression of the H7HA construct, an indirect immunofluorescent assay was carried out using an anti-H7N9 HA mouse monoclonal antibody. Briefly, human rhabdomyosarcoma (RD) cells were plated on two-well chamber slides (BD Biosciences), at a density to obtain 60-70% confluency the next day in complete DMEM medium with 10% FBS (GIBCO) and allowed to adhere overnight. The cells were transfected with pH7HA and the control plasmid pGX0001 (1 μg/well) using TurboFectin™8.0 Transfection Reagent (OriGene) according to the manufacturer's instructions. Forty-eight hours later, the cells were washed gently three times with 1×PBS and fixed on slides using ice cold methanol for 10 min. The cells were incubated with anti-H7N9 HA mouse monoclonal antibody (Sino Biological Inc., Cat#11082-MM04) at a 1:400 dilution for 2 hrs at room temperature. The slides were then incubated with the Alexa 555-conjugated anti-mouse secondary antibody (Cell Signaling Technology) for 60 min in the dark, and analyzed by fluorescent microscopy (Leica DM4000B, Leica Microsystems Inc., USA) using the SPOT Advanced software program (SPOT™ Diagnostic Instruments, Inc.).

High membrane expression was observed by fluorescent microscopy in the pH7HA-transfected cells (FIG. 21C), supporting the idea that the expressed HA protein was a surface protein and the protein exhibited a relatively native conformation. As a control, expression was not detected in pGX0001 (null vector)-transfected cells.

Example 7

Induction of Cross-Reactive Antibodies by H7HA DNA Immunogen

Immunization of Mice:

Upon confirming expression of the pH7HA construct, the ability of this immunogen to drive cross-reactive antibody responses was investigated. Female 8-week-old BALB/c mice were purchased from Jackson Laboratory. Their care was in accordance with the guidelines of the National Institutes of Health and the University of Pennsylvania Institutional Animal Care and Use Committee (IACUC). Mice were immunized twice, three weeks apart, with pH7HA and the serum samples collected at pre-vaccination and at two weeks post the second immunization were utilized for the ELISA assay. Mice were immunized with 25 μg of pH7HA by intramuscular injection (IM) into the quadriceps muscle followed by in vivo electroporation (EP) using the CELLECTRA® adaptive constant current electroporation device (Inovio Pharmaceuticals Inc.). Two 0.1 Amp constant current square-wave pulses were delivered through a triangular 3-electrode array consisting of 26-gauge solid stainless steel electrodes. Each pulse was 52 milliseconds in length with a 1 second delay between pulses. The mice received two immunizations, three weeks apart. Serum samples were collected pre-immunization and two weeks after the second vaccination time point for the ELISA and Hemagglutination Inhibition (HAI) assays. Four weeks after the second immunization, the mice were sacrificed for analysis of cellular immune responses.

H7N9 HA-Specific Antibody Determination:

The measurement of IgG antibodies specific for H7HA was performed by ELISA in both immunized and control mice. The plates were coated with 0.5 mg/ml of H7N9 A/Shanghai/1/2013 influenza HA protein, A/Anhui/1/2013 influenza HA1 protein and A/Hangzhou/1/2013 HA1 protein (Sino Biological Inc.), respectively, and standard ELISA was carried out (Yan et al., (2007) *Mol Ther* 15: 411). Endpoint titers were determined, as previously described (Frey et al., (1998) *J Immunol Methods* 221: 35). The mathematical formula used to calculate the endpoint titer cutoffs is expressed as the standard deviation multiplied by a factor that was based on the number of negative controls (naïve sera) (n=10) and the confidence level (95%). The endpoint titer is reported as the reciprocal of the last dilution that remained above the endpoint cutoff.

As shown in FIGS. 22A, 22B and 22C, high-titer vaccine-induced antibody responses were detected against three different HA proteins in the immunized mice. The average HA-specific antibody endpoint titers against A/Shanghai/1/2013 HA, A/Anhui/1/2013 HA1 and A/Hangzhou/1/2013 HA1 were 222,074 (range 50,000-1,581,111), 368,019 (range 50,000-1,581,111) and 315,542 (range 50,000-1,581,111), respectively (FIG. 22D). These data indicated that vaccination with pH7HA elicited strong and broad antibody responses.

The surface HA protein of the influenza virus contains two structural elements (head and stalk) that differ in their potential utility as vaccine targets. Antibodies targeting areas of the HA globular head region (HA1) can drive HA1 activity and viral neutralization. HA1 titers against A/Anhui/1/2013 were tested. However, high-titer cross-reactive binding antibodies against A/Anhui/1/2013 HA1 and A/Hangzhou/1/2013 HA1 regions were confirmed in all vaccinated mice. High titer binding was also observed against A/Shanghai/2013. Therefore, vaccination with pH7HA DNA vaccine appears to induce broadly reactive antibodies against multiple H7N9 strains.

Example 8

Induction of Protective Antibodies by H7HA DNA Immunogen

In order to test whether the cross-reactive antibodies can be protective, a standard Hemagglutination Inhibition assay (HA1) was used to test the ability of the pH7N9 plasmid to generate functional antibodies with HA1 activity as HA1 antibody is the major correlate of protection for flu vaccines. Sera samples were treated with receptor-destroying enzyme (RDE, 1:3 ratio) at 37° C. overnight for 18-20 hrs followed by complement inactivation at 56° C. for 45 min. Starting with a 1:10 dilution in PBS, twofold serial dilutions of RDE-treated serum were serially diluted down on 96-well V-bottom microtiter plates. Four hemagglutinating dose of A/Anhui/1/13 was added to each well and the serum-virus mixture were incubated at room temperature for 1.5 hrs. Following incubation, 50 μl horse red blood cells (1% cells+0.5% Bovine Serum Albumin Fraction V in 0.85% saline solution) were added to each well and incubated for 1.25 hrs at room temperature. The HA1 antibody titer was scored as the reciprocal of the highest dilution that did not exhibit agglutination of red blood cells. Each assay was performed in duplicate.

Figure 22:
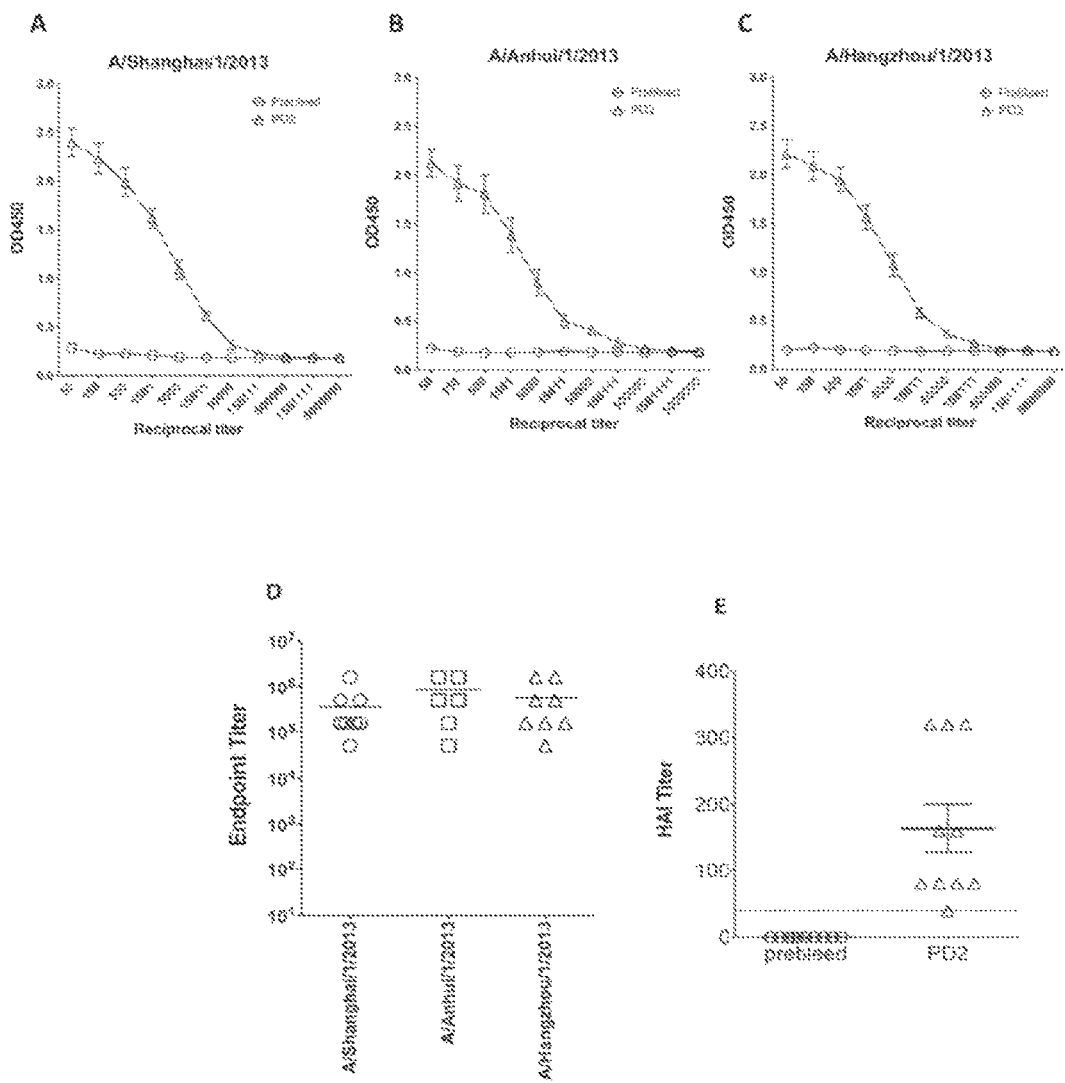

The A/Anhui/1/2013 H7N9 strain was quantified and used to determine a serum HA1 antibody titer induced by the vaccination. As depicted in FIG. 22E, two weeks after two immunizations, pH7HA induced protective HA1 titers ≥(1:40) in every immunized animal (n=10) with a GMT titer of 1:130 in the pH7HA-immunized mice. The strong and long-lasting antibodies measured can allow for the development of HA1 antibody dependent influenza DNA vaccines. Furthermore, a potential human dose could be in the range of just 500 μg to 1 mg per immunization.

Example 9

Induction of Potent Antigen-Specific Effector T Cell Memory Responses

Cell mediated immunity can be involved with virus clearance. The number of IFN-γ secreting cells correlates with the efficacy of live, attenuated influenza vaccine in children. The ability of pH7HA to induce antigen-specific cellular immune responses was explored.

IFN-γELISpot Assay:

Mouse IFN-γ ELISpot assay was performed, as described previously (Yan et al., (2007) *Mol Ther* 15: 411). A set of peptides spanning the entire consensus H7HA protein, each containing 15 amino acid residues overlapping by 8 amino acids, were synthesized from GenScript (Piscataway, N.J.). The entire set of peptides was pooled at a concentration of 2 μg/ml/peptide into 4 pools as antigens for specific stimulation of the IFN-γ release. Concavalin A (Sigma-Aldrich, St. Louis, Mo.), at 5 μg/ml, and complete culture medium were used as positive and negative control, respectively. The average number of spot forming cells (SFC) was adjusted to 1×106 splenocytes.

C57BL/6 mice were immunized twice with pH7HA, sacrificed four weeks post the second immunization (FIG. 23A), and the IFN-γ ELISpot assay was performed. As shown in FIG. 23B, the average response against four pools of H7HA overlapping peptides in the mice immunized with pH7HA was 504±132 SFU/$10^6$ splenocytes, while minimal background spots were observed in naïve mice. Strong IFN-γ responses were induced by vaccination with pH7HA.

Intracellular Cytokine Stain for Flow Cytometry:

The phenotype and cytokine profile production of the memory T cells generated was characterized. Splenocytes were added to a 96-well plate (1×$10^6$/well) and were stimulated with H7 peptide for 5-6 hrs at 37° C./5% $CO_2$ in the presence of Protein Transport Inhibitor Cocktail (Brefeldin A and Monensin) (eBioscience) according to the manufacturers' instructions. The Cell Stimulation Cocktail (plus protein transport inhibitors) (phorbol 12-myristate 13-acetate (PMA), ionomycin, brefeldin A and monensin) (eBioscience) was used as a positive control. R10 media was used as a negative control. In cultures being used to measure degranulation, anti-CD107a (FITC; clone 1D4B; Biolegend) was added at this time to enhance staining. The cells were then fixed and stained. Briefly, the cells were washed in FACS buffer (PBS containing 0.1% sodium azide and 1% FCS) before surface staining with fluorochrome-conjugated antibodies. Cells were washed with FACS buffer fixation and permeabilization using the BD Cytofix/Cytoperm™ (BD, San Diego, Calif., USA) according to the manufacturer's protocol followed by intracellular staining.

The following antibodies were used for surface staining LIVE/DEAD Fixable Violet Dead Cell stain kit (Invitrogen), CD19 (V50; clone 1D3; BD Biosciences) CD4 (V500; clone RM4-5; BD Biosciences), CD8 (PE-TexasRed; clone 53-6.7; Abcam), CD44 (A700; clone IM7; Biolegend). For intracellular staining the following antibodies were used: IFN-γ (APC; clone XMG1.2; Biolegend), TNF-α (PE; clone MP6-XT22; eBioscience), IL-2 (PeCy7; clone JES6-5F14; eBioscience), CD3 (PerCP/Cy5.5; clone 145-2C11; Biolegend). All data were collected using a LSRII flow cytometer (BD Biosciences) and analyzed using FlowJo software (Tree Star, Ashland, Oreg.) and SPICE v5.2. Boolean gating was performed using FlowJo software to examine the polyfunctionality of the T cells from vaccinated animals. For flow cytometry, cells were gated on singlets using FSC-H by FSC-A followed by gating on LIVE-DEAD (dump channel), CD3+ CD4+ CD8− T and CD3+ CD8+ CD4− T cells to examine the CD4+ and CD8+ T-cell populations. Standard and paired student's t-tests were applied to analyze statistical significance of all quantitative data produced in this study. A p<0.05 was considered statistically significant.

The longevity and quality of CD4 and CD8 effector T cell memory induced by the H7HA DNA vaccine was studied. Four weeks after the last vaccination, mice were sacrificed and splenocytes were stimulated in vitro with H7HA pooled peptides and the production of IFN-γ, TNF-α, and IL-2 by $CD4^+$ $CD44^+$ and $CD8^+$ $CD44^+$ T cells was analyzed. The H7HA DNA vaccine elicited significant HA-specific $CD4^+$ T cells producing all three cytokines (FIG. 24A), and a significant number of these cells were double positive (67%) and triple-positive (7%) (FIGS. 24B-C). The triple positive and $TNF\alpha^+IL2^+$ double positive T cell phenotypes normally represent effector memory and central memory T cells, indicating the induction of a memory like CD4 T cell immune response by the HA vaccine. In terms of CD8 T cells, vaccination with pH7HA elicited substantially higher frequencies of HA-specific IFNγ$^+$CD8 T cells, with up to 3.7% of total splenic $CD44^+CD8^+$ T cells (FIG. 25A) producing either IFN-γ$^+$ alone (0.76%), dual IFNγ$^+$/TNFα$^+$ (2.7%) or triple IFNγ$^+$/IL-2$^+$/TNFα$^+$ (0.28%) (FIGS. 25A-C). To further characterize the vaccine-induced T cells, the cytotoxic potential of the induced $CD8^+$ T cells undergoing degranulation was analyzed. Cultures were stained with an antibody to CD107a, which is a marker for degranulation, and CD8 T cells from the vaccinated mice showed a significant increase of antigen-specific (IFNγ$^+$CD107a$^+$: 3.8%) degranulation compared to naïve mice.

Figure 24:
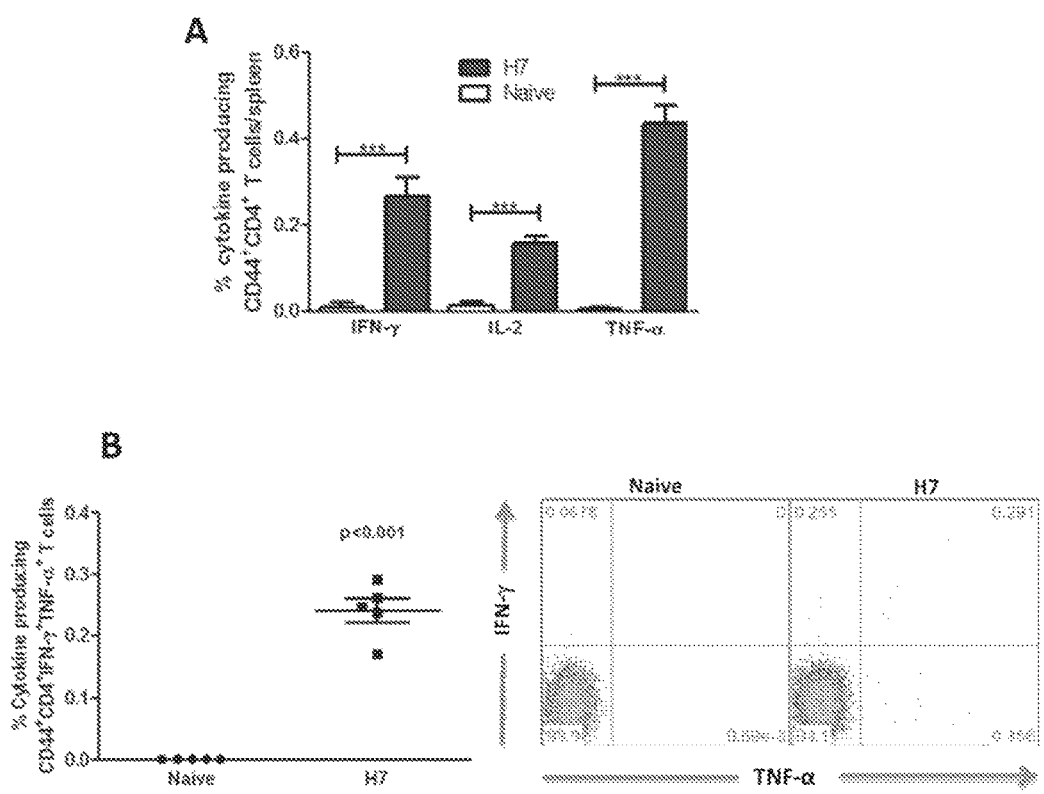
Figure 24:
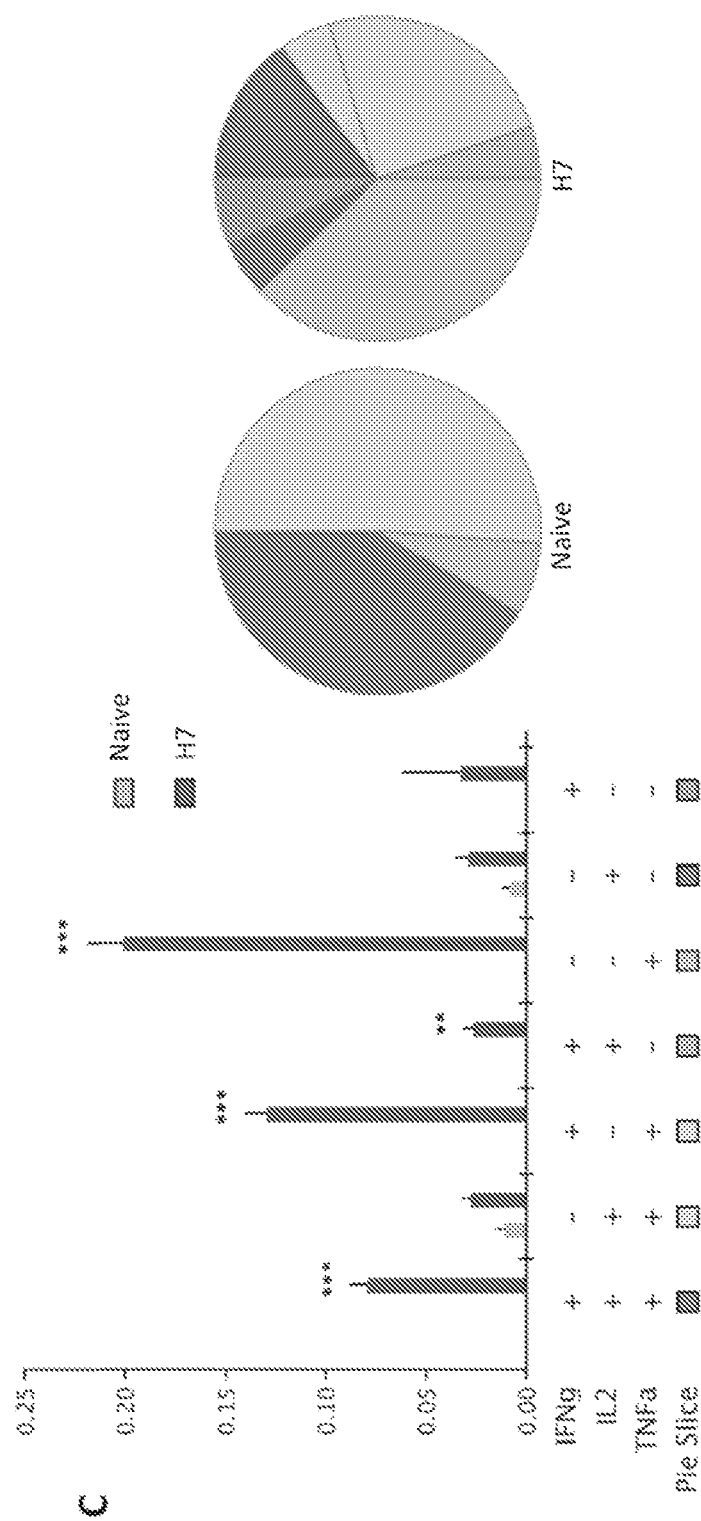
Figure 25:
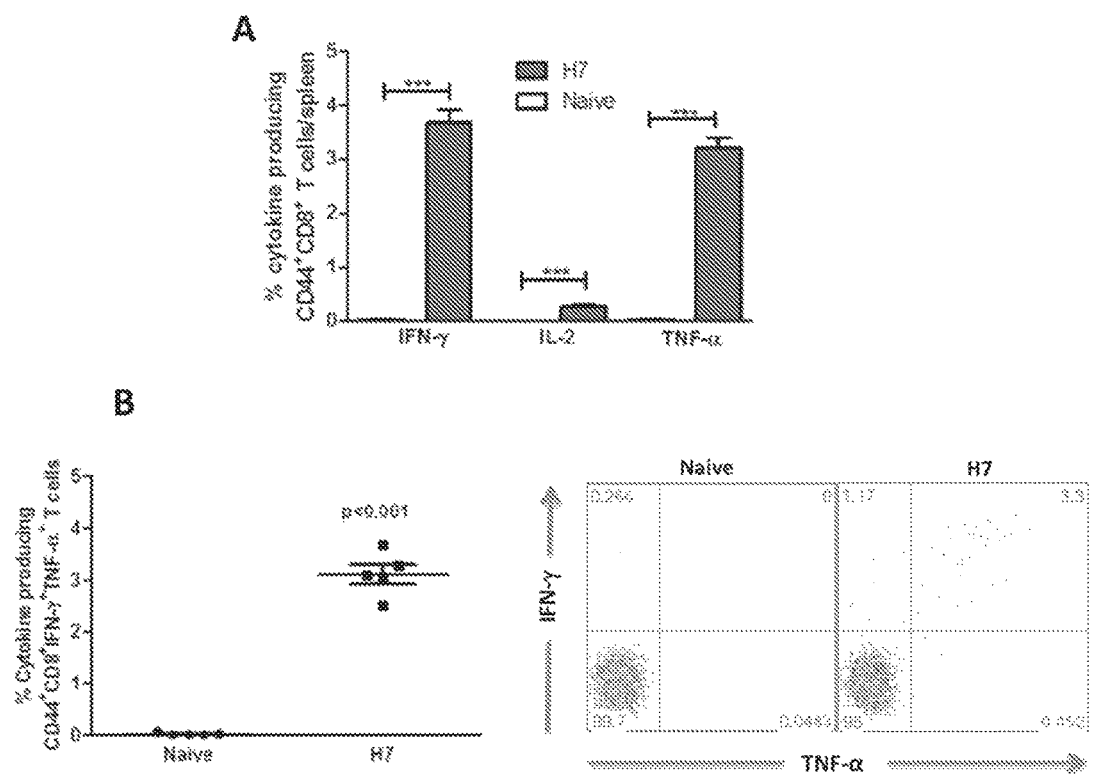
Figure 25:
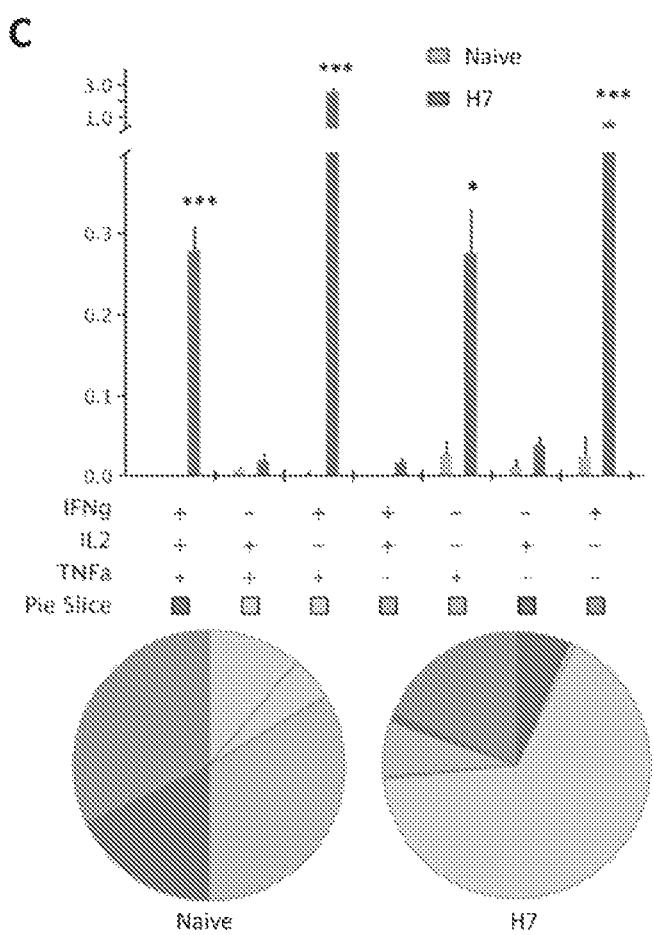
Figure 25:
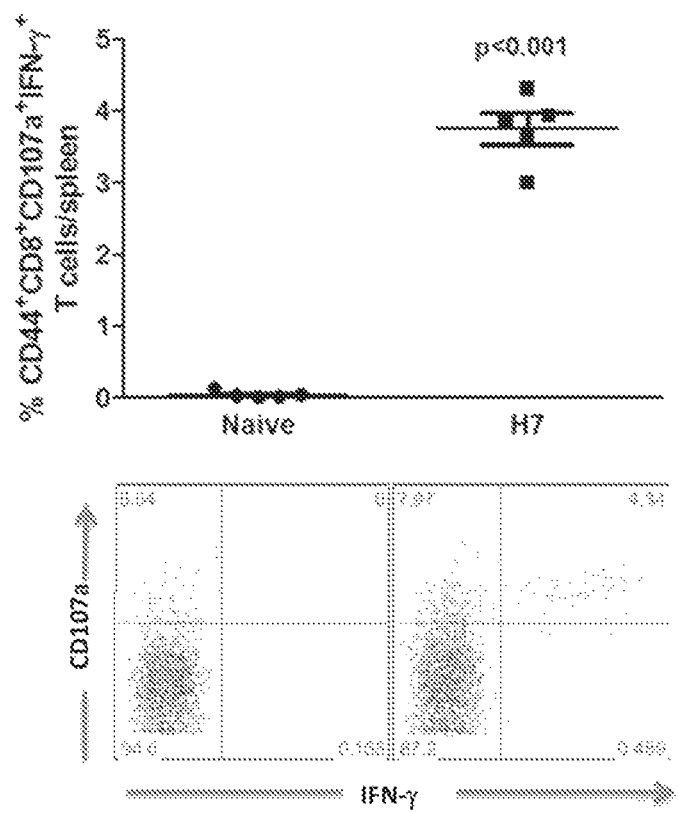

These results are indicative of the vaccine's potent ability to induce cytolytic T cell responses with the potential ability to clear H7N9 influenza infected cells. In addition, the vaccine also induced a high frequency of TNF-α producing HA-specific CD4 (0.4%) and CD8 T cells (3.2%), with a modest but significant increase in IL-2 responses (0.2% and 0.3%, respectively) compared to the naïve group (FIGS. 24A and 25A). Interestingly, the proportional order of effector CD4 and CD8 T cell subpopulations in response to H7 HA stimulation was similar, with IFNγ$^+$/TNFα$^+$ being greater than IFNγ$^+$/IL2$^+$/TNFα$^+$. The high frequencies of effector cells secreting IFNγ (CD8: 3.7%; CD4: 0.3%), IFNγ$^+$/TNFα$^+$ (CD8: 3.1%; CD4: 0.24%), and IFNγ$^+$/IL2$^+$/TNFα$^+$ among the HA-specific CD4 and CD8 T cell populations are indicative of strong vaccine potency induced by pH7HA vaccination (FIGS. 24 and 25). Overall, the frequency hierarchy of effector CD4 and CD8 memory T cells expressing one (1+), any combination of two (2+), or all three cytokine (3+) by flow cytometry were CD4$^+$CD44$^+$: 1+(26%), 2+(67%), 3+(7%) and CD8+CD44+: 1+(50%), 2+(35%), 3+(15%). Taken together, strong effector and memory T cells, as well as protective antibody responses induced by this vaccination approach were observed. The magnitude of the T cell responses are similar to those induced by viral infection rather than weak responses which are generated by traditional DNA immunization.

pH7HA was shown to induce both potent polyfunctional effector CD4 and CD8 T cell memory responses. The percentage of antigen-specific CD8 cells secreting IFNγ+ CD107a+ increased significantly, indicating potential ability of this vaccine to induce cytolytic T cell responses to clear influenza H7N9 infected cells. These data support the idea that the synthetic vaccine could induce both antigen-specific antibody and T cell responses, which would be important for protection during a pandemic.

Example 10

Vaccination with pH7HA Elicits Complete Protection Against H7N9 Virus Challenge

To determine if vaccination with pH7HA could elicit protective immunity to a lethal viral challenge, mice were immunized with pH7HA twice, three weeks apart, then challenged with a lethal dose of the H7N9 virus A/Anhui/1/2013 four weeks post the final immunization, and then monitored for weight loss for 14 days (FIG. 26A). Twenty female BALB/c mice were divided into two groups (n=10): the naïve and immunized group. The mice in the immunized group were immunized with 25 µg of pH7HA twice, three weeks apart. Four weeks after the second immunization, the mice were anesthetized with isoflurane and subsequently challenged by intranasal administration (bolus delivery into the nostrils using a standard micropipette) of 100×LD$_{50}$ of A/Anhui/1/13 influenza virus in 50 µl Dulbecco's Modified Eagle Medium (DMEM) plus 2% Fetal Bovine Serum (FBS). After challenge, the animals were weighed daily for 14 days and monitored for clinical signs of influenza infection using an approved scoring sheet. All surviving animals were monitored for a total of 28 days. All procedures and the scoring method were approved by the Institutional Animal Care Committee at the National Microbiology Laboratory (NML) of the Public Health Agency of Canada (PHAC) according to the guidelines of the Canadian Council on Animal Care. All infectious work was performed in the 'Biosafety Level 4' (BSL4) facility.

According to the protocol established prior to the study, animals falling below the threshold of 70% of their initial body weight were humanely euthanized. As shown in FIGS. 26B and 26C, in naïve group, one mouse lost 30% of its body weight by day 6 post-challenge, five mice exhibited 30% weight loss by day 7 post-challenge, and the rest of four mice lost 30% of their body weight by day 8. In contrast, all vaccinated mice (n=10) survived to day 28 post challenge with no observed pathogenic effects or weight loss at which time the study was ended. These data support that the synthetic DNA vaccine induced immune responses that protect against influenza H7N9 infection.

The rapid development of a synthetic H7N9 HA DNA vaccine efficiently delivered in vivo by EP capable of eliciting not only strong effector T cell memory responses, but also broadly reactive antibody responses. Immunization with the pH7HA DNA vaccine induced protective HA1 titers in all immunized animals and resulted in 100% protection from mortality and morbidity due to influenza H7N9 infection. The H7N9 HA vaccine protected against newly emergent influenza subtypes. The development of a highly potent, synthetic, H7N9 HA DNA vaccine which in combination with an adaptive constant current electroporation delivery platform was capable of eliciting robust cellular immune responses, broadly cross-reactive antibody responses and generating complete protection from lethal challenge with just a few week development and vaccination regime.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, can be made without departing from the spirit and scope thereof.

What is claimed is:

1. An isolated nucleic acid comprising a nucleic acid sequence selected from the group consisting of SEQ ID NO: 39, a nucleic acid sequence that is 95% identical over the entire length of the nucleic acid sequence of SEQ ID NO: 39, a fragment of SEQ ID NO: 39 comprising at least 90 nucleotides, and a nucleic acid sequence that is 95% identical to a fragment of SEQ ID NO: 39 comprising at least 90 nucleotides.

2. The isolated nucleic acid of claim 1, wherein the isolated nucleic acid comprises a nucleic acid sequence selected from the group consisting of a nucleic acid sequence that is 95% identical over the entire length of the nucleic acid sequence of SEQ ID NO: 39 and a nucleic acid sequence that is 95% identical to a fragment of SEQ ID NO: 39 comprising at least 90 nucleotides.

3. A recombinant vector comprising the isolated nucleic acid of claim 1.

4. An expression vector comprising the isolated nucleic acid of claim 1 operably linked to regulatory elements.

5. An expression vector comprising the isolated nucleic acid of claim 1 operably linked to regulatory elements that are functional in a human cell.

6. The expression vector of claim 5, wherein the expression vector is a plasmid.

7. The isolated nucleic acid of claim 1, wherein the isolated nucleic acid consists of the nucleic acid sequence of SEQ ID NO: 39.

8. A recombinant vector comprising the isolated nucleic acid of claim 7.

9. An expression vector comprising the isolated nucleic acid of claim 7 operably linked to regulatory elements.

10. An expression vector comprising the isolated nucleic acid of claim 7 operably linked to regulatory elements that are functional in a human cell.

11. The expression vector of claim 10, wherein the expression vector is a plasmid.

12. A composition comprising:
(a) a first nucleic acid sequence comprising one or more nucleotide sequences selected from the group consisting of SEQ ID NO: 39, a nucleic acid sequence that is 95% identical over the entire length of the nucleic acid sequence of SEQ ID NO: 39, a fragment of SEQ ID NO: 39 comprising at least 90 nucleotides, and a nucleic acid sequence that is 95% identical to a fragment of SEQ ID NO: 39 comprising at least 90 nucleotides; and
(b) a second nucleic acid sequence that encodes a protein selected from the group consisting of one or more of: H1, H2, H3, H4, H5, H6, H7, H8, H9, H10, H11, H12, H13, H14, H15, H16, N1, N2, N3, N4, N5, N6, N7, N8 and N9.

13. The composition of claim 12, wherein the first nucleic acid sequence is operably linked to regulatory elements that are functional in a human cell.

14. The composition of claim 13 comprising a plasmid that comprises the first nucleic acid sequence operably linked to regulatory elements that are functional in a human cell.

15. The composition of claim 12, wherein the second nucleic acid sequence is selected from the group consisting of one or more of:
SEQ ID NO: 1;
a nucleic acid sequence that is 95% identical over the entire length of the nucleic acid sequence of SEQ ID NO: 1;
a fragment of SEQ ID NO: 1 comprising at least 90 nucleotides;
a nucleic acid sequence that is 95% identical to a fragment of SEQ ID NO: 1 comprising at least 90 nucleotides;
SEQ ID NO: 3;
a nucleic acid sequence that is 95% identical over the entire length of the nucleic acid sequence of SEQ ID NO: 3;
a fragment of SEQ ID NO: 3 comprising at least 90 nucleotides;

a nucleic acid sequence that is 95% identical to a fragment of SEQ ID NO: 3 comprising at least 90 nucleotides;

SEQ ID NO: 6;

a nucleic acid sequence that is 95% identical over the entire length of the nucleic acid sequence of SEQ ID NO: 6;

a fragment of SEQ ID NO: 6 comprising at least 90 nucleotides;

a nucleic acid sequence that is 95% identical to a fragment of SEQ ID NO: 6 comprising at least 90 nucleotides;

SEQ ID NO: 8;

a nucleic acid sequence that is 95% identical over the entire length of the nucleic acid sequence of SEQ ID NO: 8;

a fragment of SEQ ID NO: 8 comprising at least 90 nucleotides; and a nucleic acid sequence that is 95% identical to a fragment of SEQ ID NO: 8 comprising at least 90 nucleotides.

16. The composition of claim 12, further comprising a peptide encoded by the nucleic acid sequence of SEQ ID NO: 39.

17. The composition of claim 12, further comprising a peptide comprising the amino acid sequence of SEQ ID NO: 40.

18. A vaccine comprising the isolated nucleic acid of claim 1.

19. The vaccine of claim 18 further comprising a peptide encoded by the nucleic acid sequence of SEQ ID NO: 39.

20. The vaccine of claim 18 further comprising a peptide comprising the amino acid sequence of SEQ ID NO: 40.

21. A vaccine comprising the nucleic acid sequence of SEQ ID NO: 39.

22. A vaccine against an influenza virus comprising a nucleic acid sequence of claim 1.

23. The vaccine of claim 22, wherein the nucleic acid sequence comprises the nucleic acid sequence of SEQ ID NO: 39.

24. The vaccine of claim 22, where the influenza virus is H7N9 influenza virus.

25. The vaccine of claim 21 further comprising a peptide encoded by the nucleic acid sequence of SEQ ID NO: 39.

26. The vaccine of claim 21 further comprising a peptide comprising the amino acid sequence of SEQ ID NO: 40.

* * * * *

SEQUENCE LISTING

```
<160> NUMBER OF SEQ ID NOS: 40

<210> SEQ ID NO 1
<211> LENGTH: 1695
<212> TYPE: DNA
<213> ORGANISM: Artificial Sequence
<220> FEATURE:
<223> OTHER INFORMATION: Influenza H1 DNA sequence

<400> SEQUENCE: 1
atgaaggcta tcctcgtcgt gctgctgtac accttcgcca ccgccaacgc cgataccctg      60
tgcatcggct accacgccaa caacagcacc gacaccgtgg ataccgtgct ggaaaagaac     120
```

-continued gtgaccgtga cccacagcgt gaacctgctg gaagataagc acaacggcaa gctgtgcaag 180
ctgagaggcg tggcccctct gcacctgggc aagtgcaata tcgccggctg gattctgggc 240
aaccccgagt gcgagagcct gtctaccgct agctcctggt cctacatcgt ggagacaagc 300
agcagcgaca acggcacctg ttaccccggc gacttcatcg actacgagga actgcgggag 360
cagctgagca gcgtgtccag cttcgagcgg ttcgagatct tccccaagac cagctcctgg 420
cccaaccacg acagcaacaa gggcgtgacc gccgcctgtc ctcacgctgg cgccaagagc 480
ttctacaaga acctgatctg gctggtcaag aagggcaaca gctaccccaa gctgagcaag 540
agctacatca acgacaaggg caaagaggtc ctcgtcctct ggggcatcca ccaccctagc 600
accagcgccg accagcagag cctgtaccag aacgccgacg cctacgtgtt cgtgggctca 660
tctcggtaca gcaagaagtt caagcccgag atcgccatca gacccaaagt gcgggaccag 720
gaaggccgga tgaactacta ctggaccctg gtggagcccg gcgacaagat caccttcgag 780
gccaccggca atctggtggt gcccagatac gccttcgcca tggaaagaaa cgccggcagc 840
ggcatcatca tcagcgacac ccccgtgcac gactgcaaca ccacctgtca gacccccaag 900
ggcgccatca acaccagcct gcccttccag aacatccacc ccatcaccat cggcaagtgc 960
cctaagtacg tgaagtccac taagctcaga ctggccaccg gcctgagaaa cgtgcccagc 1020
atccagagca gaggcctgtt tggcgccatt gccggcttta tcgagggcgg ctggaccgga 1080
atggtggacg ggtggtacgg ctaccaccac cagaatgagc agggcagcgg ctacgccgcc 1140
gacctgaagt ccacacagaa cgccatcgac gagatcacca acaaagtgaa cagcgtgatc 1200
gagaagatga acacccagtt caccgccgtg ggcaaagagt tcaaccacct ggaaaagcgg 1260
atcgagaacc tgaacaagaa ggtggacgac ggcttcctgg acatctggac ctacaacgcc 1320
gagctgctgg tgctgctgga aaacgagcgg accctggact accacgactc caacgtgaag 1380
aatctgtacg agaaagtgcg gagccagctg aagaacaacg ccaaagagat cggcaacggc 1440
tgcttcgagt tctaccacaa gtgcgacaac acctgtatgg aaagcgtgaa gaacggcacc 1500
tacgactacc ccaagtacag cgaggaagcc aagctgaacc gggaagagat cgacggcgtg 1560
aagctggaaa gcacccggat ctaccagatc ctggccatct actctactgt ggccagctca 1620
ctggtgctgg tggtgtccct gggcgccatc tccttttgga tgtgctccaa cggcagcctg 1680
cagtgccgga tctgc 1695

<210> SEQ ID NO 2
<211> LENGTH: 566
<212> TYPE: PRT
<213> ORGANISM: Artificial Sequence
<220> FEATURE:
<223> OTHER INFORMATION: Influenza Protein H1 Sequence

<400> SEQUENCE: 2

Met Lys Ala Ile Leu Val Val Leu Leu Tyr Thr Phe Ala Thr Ala Asn
1 5 10 15

Ala Asp Thr Leu Cys Ile Gly Tyr His Ala Asn Asn Ser Thr Asp Thr
20 25 30

Val Asp Thr Val Leu Glu Lys Asn Val Thr Val Thr His Ser Val Asn
35 40 45

Leu Leu Glu Asp Lys His Asn Gly Lys Leu Cys Lys Leu Arg Gly Val
50 55 60

Ala Pro Leu His Leu Gly Lys Cys Asn Ile Ala Gly Trp Ile Leu Gly
65 70 75 80

```
Asn Pro Glu Cys Glu Ser Leu Ser Thr Ala Ser Ser Trp Ser Tyr Ile
                 85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
            130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Ala Tyr Val Phe Val Gly Ser Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
```

```
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 3
<211> LENGTH: 1818
<212> TYPE: DNA
<213> ORGANISM: Artificial Sequence
<220> FEATURE:
<223> OTHER INFORMATION: IgE-H1-HAT Antigen DNA Sequence

<400> SEQUENCE: 3
ttaattaagg atccgccacc atggactgga cctggattct gttcctggtg gctgctgcca     60
ctagagtgca cagcatgaag gctatcctcg tcgtgctgct gtacaccttc gccaccgcca    120
acgccgatac cctgtgcatc ggctaccacg ccaacaacag caccgacacc gtggataccg    180
tgctggaaaa gaacgtgacc gtgacccaca gcgtgaacct gctggaagat aagcacaacg    240
gcaagctgtg caagctgaga ggcgtggccc ctctgcacct gggcaagtgc aatatcgccg    300
gctggattct gggcaacccc gagtgcgaga gcctgtctac cgctagctcc tggtcctaca    360
tcgtggagac aagcagcagc gacaacggca cctgttaccc cggcgacttc atcgactacg    420
aggaactgcg ggagcagctg agcagcgtgt ccagcttcga gcggttcgag atcttcccca    480
agaccagctc ctggcccaac cacgacagca acaagggcgt gaccgccgcc tgtcctcacg    540
ctggcgccaa gagcttctac aagaacctga tctggctggt caagaagggc aacagctacc    600
ccaagctgag caagagctac atcaacgaca agggcaaaga ggtcctcgtc ctctggggca    660
tccaccaccc tagcaccagc gccgaccagc agagcctgta ccagaacgcc gacgcctacg    720
tgttcgtggg ctcatctcgg tacagcaaga agttcaagcc cgagatcgcc atcagaccca    780
aagtgcggga ccaggaaggc cggatgaact actactggac cctggtggag cccggcgaca    840
agatcacctt cgaggccacc ggcaatctgg tggtgcccag atacgccttc gccatggaaa    900
gaaacgccgg cagcggcatc atcatcagcg acacccccgt gcacgactgc aacaccacct    960
gtcagacccc caagggcgcc atcaacacca gcctgccctt ccagaacatc caccccatca   1020
ccatcggcaa gtgccctaag tacgtgaagt ccactaagct cagactggcc accggcctga   1080
gaaacgtgcc cagcatccag agcagaggcc tgtttggcgc cattgccggc tttatcgagg   1140
gcggctggac cggaatggtg gacgggtggt acggctacca ccaccagaat gagcagggca   1200
gcggctacgc cgccgacctg aagtccacac agaacgccat cgacgagatc accaacaaag   1260
tgaacagcgt gatcgagaag atgaacaccc agttcaccgc cgtgggcaaa gagttcaacc   1320
acctggaaaa gcggatcgag aacctgaaca agaaggtgga cgacggcttc ctggacatct   1380
ggacctacaa cgccgagctg ctggtgctgc tggaaaacga gcggaccctg gactaccacg   1440
actccaacgt gaagaatctg tacgagaaag tgcggagcca gctgaagaac aacgccaaag   1500
agatcggcaa cggctgcttc gagttctacc acaagtgcga caacacctgt atggaaagcg   1560
tgaagaacgg cacctacgac taccccaagt acagcgagga agccaagctg aaccgggaag   1620
agatcgacgg cgtgaagctg gaaagcaccc ggatctacca gatcctggcc atctactcta   1680
```

```
ctgtggccag ctcactggtg ctggtggtgt ccctgggcgc catctccttt tggatgtgct    1740
ccaacggcag cctgcagtgc cggatctgca tctaccccta cgacgtgccc gactacgcct    1800
gatgactcga ggcgcgcc                                                  1818
```

<210> SEQ ID NO 4
<211> LENGTH: 593
<212> TYPE: PRT
<213> ORGANISM: Artificial Sequence
<220> FEATURE:
<223> OTHER INFORMATION: IgE-H1-HATanitgen amino acid seqeunce

<400> SEQUENCE: 4

```
Met Asp Trp Thr Trp Ile Leu Phe Leu Val Ala Ala Thr Arg Val
1               5                   10                  15

His Ser Met Lys Ala Ile Leu Val Val Leu Leu Tyr Thr Phe Ala Thr
            20                  25                  30

Ala Asn Ala Asp Thr Leu Cys Ile Gly Tyr His Ala Asn Asn Ser Thr
        35                  40                  45

Asp Thr Val Asp Thr Val Leu Glu Lys Asn Val Thr Val Thr His Ser
    50                  55                  60

Val Asn Leu Leu Glu Asp Lys His Asn Gly Lys Leu Cys Lys Leu Arg
65                  70                  75                  80

Gly Val Ala Pro Leu His Leu Gly Lys Cys Asn Ile Ala Gly Trp Ile
                85                  90                  95

Leu Gly Asn Pro Glu Cys Glu Ser Leu Ser Thr Ala Ser Ser Trp Ser
            100                 105                 110

Tyr Ile Val Glu Thr Ser Ser Ser Asp Asn Gly Thr Cys Tyr Pro Gly
        115                 120                 125

Asp Phe Ile Asp Tyr Glu Glu Leu Arg Glu Gln Leu Ser Ser Val Ser
    130                 135                 140

Ser Phe Glu Arg Phe Glu Ile Phe Pro Lys Thr Ser Ser Trp Pro Asn
145                 150                 155                 160

His Asp Ser Asn Lys Gly Val Thr Ala Ala Cys Pro His Ala Gly Ala
                165                 170                 175

Lys Ser Phe Tyr Lys Asn Leu Ile Trp Leu Val Lys Lys Gly Asn Ser
            180                 185                 190

Tyr Pro Lys Leu Ser Lys Ser Tyr Ile Asn Asp Lys Gly Lys Glu Val
        195                 200                 205

Leu Val Leu Trp Gly Ile His His Pro Ser Thr Ser Ala Asp Gln Gln
    210                 215                 220

Ser Leu Tyr Gln Asn Ala Asp Ala Tyr Val Phe Val Gly Ser Ser Arg
225                 230                 235                 240

Tyr Ser Lys Lys Phe Lys Pro Glu Ile Ala Ile Arg Pro Lys Val Arg
                245                 250                 255

Asp Gln Glu Gly Arg Met Asn Tyr Tyr Trp Thr Leu Val Glu Pro Gly
            260                 265                 270

Asp Lys Ile Thr Phe Glu Ala Thr Gly Asn Leu Val Val Pro Arg Tyr
        275                 280                 285

Ala Phe Ala Met Glu Arg Asn Ala Gly Ser Gly Ile Ile Ile Ser Asp
    290                 295                 300

Thr Pro Val His Asp Cys Asn Thr Thr Cys Gln Thr Pro Lys Gly Ala
305                 310                 315                 320

Ile Asn Thr Ser Leu Pro Phe Gln Asn Ile His Pro Ile Thr Ile Gly
                325                 330                 335
```

Lys Cys Pro Lys Tyr Val Lys Ser Thr Lys Leu Arg Leu Ala Thr Gly
                340                 345                 350

Leu Arg Asn Val Pro Ser Ile Gln Ser Arg Gly Leu Phe Gly Ala Ile
            355                 360                 365

Ala Gly Phe Ile Glu Gly Gly Trp Thr Gly Met Val Asp Gly Trp Tyr
370                 375                 380

Gly Tyr His His Gln Asn Glu Gln Gly Ser Gly Tyr Ala Ala Asp Leu
385                 390                 395                 400

Lys Ser Thr Gln Asn Ala Ile Asp Glu Ile Thr Asn Lys Val Asn Ser
                405                 410                 415

Val Ile Glu Lys Met Asn Thr Gln Phe Thr Ala Val Gly Lys Glu Phe
            420                 425                 430

Asn His Leu Glu Lys Arg Ile Glu Asn Leu Asn Lys Lys Val Asp Asp
        435                 440                 445

Gly Phe Leu Asp Ile Trp Thr Tyr Asn Ala Glu Leu Leu Val Leu Leu
    450                 455                 460

Glu Asn Glu Arg Thr Leu Asp Tyr His Asp Ser Asn Val Lys Asn Leu
465                 470                 475                 480

Tyr Glu Lys Val Arg Ser Gln Leu Lys Asn Asn Ala Lys Glu Ile Gly
                485                 490                 495

Asn Gly Cys Phe Glu Phe Tyr His Lys Cys Asp Asn Thr Cys Met Glu
            500                 505                 510

Ser Val Lys Asn Gly Thr Tyr Asp Tyr Pro Lys Tyr Ser Glu Glu Ala
        515                 520                 525

Lys Leu Asn Arg Glu Glu Ile Asp Gly Val Lys Leu Glu Ser Thr Arg
    530                 535                 540

Ile Tyr Gln Ile Leu Ala Ile Tyr Ser Thr Val Ala Ser Ser Leu Val
545                 550                 555                 560

Leu Val Val Ser Leu Gly Ala Ile Ser Phe Trp Met Cys Ser Asn Gly
                565                 570                 575

Ser Leu Gln Cys Arg Ile Cys Ile Tyr Pro Tyr Asp Val Pro Asp Tyr
            580                 585                 590

Ala

<210> SEQ ID NO 5
<211> LENGTH: 4739
<212> TYPE: DNA
<213> ORGANISM: Artificial Sequence
<220> FEATURE:
<223> OTHER INFORMATION: pGX2009 HS09 DNA sequence

<400> SEQUENCE: 5

| | | |
|---|---|---|
| gctgcttcgc gatgtacggg ccagatatac gcgttgacat tgattattga ctagttatta | 60 |
| atagtaatca attacggggt cattagttca tagcccatat atggagttcc gcgttacata | 120 |
| acttacggta atggcccgc ctggctgacc gcccaacgac ccccgcccat tgacgtcaat | 180 |
| aatgacgtat gttcccatag taacgccaat agggactttc cattgacgtc aatgggtgga | 240 |
| gtatttacgg taaactgccc acttggcagt acatcaagtg tatcatatgc caagtacgcc | 300 |
| ccctattgac gtcaatgacg gtaaatggcc cgcctggcat tatgcccagt acatgacctt | 360 |
| atgggacttt cctacttggc agtacatcta cgtattagtc atcgctatta ccatggtgat | 420 |
| gcggttttgg cagtacatca atgggcgtgg atagcggttt gactcacggg gatttccaag | 480 |
| tctccacccc attgacgtca atgggagttt gttttggcac caaaatcaac gggactttcc | 540 |

```
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagcttggt    720
accgagctcg gatccgccac catggactgg acctggattc tgttcctggt ggctgctgcc    780
actagagtgc acagcatgaa ggctatcctc gtcgtgctgc tgtacacctt cgccaccgcc    840
aacgccgata ccctgtgcat cggctaccac gccaacaaca gcaccgacac cgtggatacc    900
gtgctggaaa agaacgtgac cgtgacccac agcgtgaacc tgctggaaga taagcacaac    960
ggcaagctgt gcaagctgag aggcgtggcc cctctgcacc tgggcaagtg caatatcgcc   1020
ggctggattc tgggcaaccc cgagtgcgag agcctgtcta ccgctagctc ctggtcctac   1080
atcgtggaga caagcagcag cgacaacggc acctgttacc ccggcgactt catcgactac   1140
gaggaactgc gggagcagct gagcagcgtg tccagcttcg agcggttcga gatcttcccc   1200
aagaccagct cctggcccaa ccacgacagc aacaagggcg tgaccgccgc ctgtcctcac   1260
gctggcgcca agagcttcta caagaacctg atctggctgg tcaagaaggg caacagctac   1320
cccaagctga gcaagagcta catcaacgac aagggcaaag aggtcctcgt cctctggggc   1380
atccaccacc ctagcaccag cgccgaccag cagagcctgt accagaacgc cgacgcctac   1440
gtgttcgtgg gctcatctcg gtacagcaag aagttcaagc ccgagatcgc catcagaccc   1500
aaagtgcggg accaggaagg ccggatgaac tactactgga ccctggtgga gcccggcgac   1560
aagatcacct tcgaggccac cggcaatctg gtggtgccca gatacgcctt cgccatggaa   1620
agaaacgccg gcagcggcat catcatcagc gacaccccccg tgcacgactg caacaccacc   1680
tgtcagaccc ccaagggcgc catcaacacc agcctgccct tccagaacat ccaccccatc   1740
accatcggca agtgccctaa gtacgtgaag tccactaagc tcagactggc caccggcctg   1800
agaaacgtgc ccagcatcca gagcagaggc ctgtttggcg ccattgccgg ctttatcgag   1860
ggcggctgga ccggaatggt ggacgggtgg tacggctacc accaccagaa tgagcagggc   1920
agcggctacg ccgccgacct gaagtccaca cagaacgcca tcgacgagat caccaacaaa   1980
gtgaacagcg tgatcgagaa gatgaacacc cagttcaccg ccgtgggcaa agagttcaac   2040
cacctggaaa agcggatcga gaacctgaac aagaaggtgg acgacggctt cctggacatc   2100
tggacctaca acgccgagct gctggtgctg ctggaaaacg agcggaccct ggactaccac   2160
gactccaacg tgaagaatct gtacgagaaa gtgcggagcc agctgaagaa caacgccaaa   2220
gagatcggca acggctgctt cgagttctac cacaagtgcg acaacacctg tatggaaagc   2280
gtgaagaacg gcacctacga ctaccccaag tacagcgagg aagccaagct gaaccgggaa   2340
gagatcgacg gcgtgaagct ggaaagcacc cggatctacc agatcctggc catctactct   2400
actgtggcca gctcactggt gctggtggtg tccctgggcg ccatctcctt ttggatgtgc   2460
tccaacggca gcctgcagtg ccggatctgc atctaccccct acgacgtgcc cgactacgcc   2520
tgatgactcg agtctagagg gcccgtttaa acccgctgat cagcctcgac tgtgccttct   2580
agttgccagc catctgttgt ttgcccctcc cccgtgcctt ccttgaccct ggaaggtgcc   2640
actcccactg tccttttccta ataaaatgag gaaattgcat cgcattgtct gagtaggtgt   2700
cattctattc tggggggtgg ggtggggcag gacagcaagg gggaggattg ggaagacaat   2760
agcaggcatg ctggggatgc ggtgggctct atggcttcta ctgggcggtt ttatggacag   2820
caagcgaacc ggaattgcca gctggggcgc cctctggtaa ggttgggaag ccctgcaaag   2880
taaactggat ggctttcttg ccgccaagga tctgatggcg caggggatca agctctgatc   2940
```

```
aagagacagg atgaggatcg tttcgcatga ttgaacaaga tggattgcac gcaggttctc   3000
cggccgcttg ggtggagagg ctattcggct atgactgggc acaacagaca atcggctgct   3060
ctgatgccgc cgtgttccgg ctgtcagcgc aggggcgccc ggttcttttt gtcaagaccg   3120
acctgtccgg tgccctgaat gaactgcaag acgaggcagc gcggctatcg tggctggcca   3180
cgacgggcgt tccttgcgca gctgtgctcg acgttgtcac tgaagcggga agggactggc   3240
tgctattggg cgaagtgccg gggcaggatc tcctgtcatc tcaccttgct cctgccgaga   3300
aagtatccat catggctgat gcaatgcggc ggctgcatac gcttgatccg gctacctgcc   3360
cattcgacca ccaagcgaaa catcgcatcg agcgagcacg tactcggatg gaagccggtc   3420
ttgtcgatca ggatgatctg gacgaagagc atcaggggct cgcgccagcc gaactgttcg   3480
ccaggctcaa ggcgagcatg cccgacggcg aggatctcgt cgtgacccat ggcgatgcct   3540
gcttgccgaa tatcatggtg gaaaatggcc gcttttctgg attcatcgac tgtggccggc   3600
tgggtgtggc ggaccgctat caggacatag cgttggctac ccgtgatatt gctgaagagc   3660
ttggcggcga atgggctgac cgcttcctcg tgctttacgg tatcgccgct cccgattcgc   3720
agcgcatcgc cttctatcgc cttcttgacg agttcttctg aattattaac gcttacaatt   3780
tcctgatgcg gtattttctc cttacgcatc tgtgcggtat ttcacaccgc atcaggtggc   3840
acttttcggg gaaatgtgcg cggaacccct atttgtttat ttttctaaat acattcaaat   3900
atgtatccgc tcatgagaca ataaccctga taaatgcttc aataatagca cgtgctaaaa   3960
cttcattttt aatttaaaag gatctaggtg aagatccttt ttgataatct catgaccaaa   4020
atcccttaac gtgagttttc gttccactga gcgtcagacc ccgtagaaaa gatcaaagga   4080
tcttcttgag atcctttttt tctgcgcgta atctgctgct tgcaaacaaa aaaaccaccg   4140
ctaccagcgg tggtttgttt gccggatcaa gagctaccaa ctctttttcc gaaggtaact   4200
ggcttcagca gagcgcagat accaaatact gttcttctag tgtagccgta gttaggccac   4260
cacttcaaga actctgtagc accgcctaca tacctcgctc tgctaatcct gttaccagtg   4320
gctgctgcca gtggcgataa gtcgtgtctt accgggttgg actcaagacg atagttaccg   4380
gataaggcgc agcggtcggg ctgaacgggg ggttcgtgca cacagcccag cttggagcga   4440
acgacctaca ccgaactgag atacctacag cgtgagctat gagaaagcgc cacgcttccc   4500
gaagggagaa aggcggacag gtatccggta agcggcaggg tcggaacagg agagcgcacg   4560
agggagcttc cagggggaaa cgcctggtat ctttatagtc ctgtcgggtt tcgccacctc   4620
tgacttgagc gtcgattttt gtgatgctcg tcaggggggc ggagcctatg gaaaaacgcc   4680
agcaacgcgg cctttttacg gttcctggcc ttttgctggc cttttgctca catgttctt    4739
```

```
<210> SEQ ID NO 6
<211> LENGTH: 1719
<212> TYPE: DNA
<213> ORGANISM: Artificial Sequence
<220> FEATURE:
<223> OTHER INFORMATION: Influenza H2 antigen DNA sequence

<400> SEQUENCE: 6
ggtaccaagc ttgccaccat ggccatcatc tacctgatcc tgctgttcac cgccgtgcgg     60
ggcgaccaga tctgcatcgg ctaccacgcc aacaacagca ccgagaaggt ggacaccatc    120
ctggaacgga acgtgaccgt gacccacgcc aaggacatcc tggaaaagac ccacaacggc    180
aagctgtgca agctgaacgg catccccccc ctggaactgg gcgactgcag cattgccggc    240
```

-continued

```
tggctgctgg gcaaccccga gtgcgaccgg ctgctgtccg tgcccgagtg gagctacatc    300
atggaaaaag agaacccccg ggacggcctg tgctaccccg gcagcttcaa cgactacgag    360
gaactgaagc acctgctgtc cagcgtgaag cacttcgaga aggtgaaaat cctgcccaag    420
gaccggtgga cccagcacac caccaccggc ggcagcagag cctgtgccgt gagcggcaac    480
cccagcttct tccggaacat ggtgtggctg accaagaagg gcagcaacta ccccgtggcc    540
aagggcagct acaacaacac ctccggagaa cagatgctga tcatctgggg cgtgcaccac    600
cccaacgacg agacagagca gcggaccctg taccagaacg tgggcaccta cgtgagcgtg    660
ggcaccagca ccctgaacaa gcggagcacc cccgagatcg ccacccggcc caaggtgaac    720
ggcctgggca gccggatgga attcagctgg accctgctgg acatgtggga caccatcaac    780
ttcgagagca ccggcaacct gatcgccccc gagtacggct tcaagatcag caagcggggc    840
agcagcggca tcatgaaaac cgagggcacc ctggaaaact gcgagacaaa gtgccagacc    900
cccctgggcg ccatcaacac caccctgccc ttccacaacg tgcaccccct gaccatcggc    960
gagtgcccca agtacgtgaa gagcgagaag ctggtgctgg ccaccggcct gcggaacgtg   1020
ccccagatcg agagcagggg cctgttcggc gccattgccg gattcatcga gggcggctgg   1080
cagggcatgg tggacgggtg gtacggctac caccacagca acgaccaggg cagcggctac   1140
gccgccgaca aagagagcac ccagaaggcc ttcgacggca tcaccaacaa ggtgaacagc   1200
gtgatcgaga agatgaacac ccagttcgag gccgtgggca aagagttcag caacctggaa   1260
cggcggctgg aaaacctgaa caagaaaatg gaagatggct tcctggacgt gtggacctac   1320
aacgccgagc tgctggtgct gatggaaaac gagaggaccc tggacttcca cgacagcaac   1380
gtgaagaacc tgtacgacaa agtgcggatg cagctgcggg acaacgtgaa agagctgggc   1440
aacggctgct tcgagttcta ccacaagtgc gacgacgagt gcatgaactc cgtgaagaac   1500
ggcacctacg actaccctaa gtacgaggaa gagtccaagc tgaaccggaa cgagatcaag   1560
ggcgtgaagc tgtccagcat gggcgtgtac cagatcctgg ccatctacgc caccgtggcc   1620
ggcagcctga gcctggctat tatgatggct ggcatcagct tttggatgtg cagcaacggc   1680
agcctgcagt gccggatctg catctgatga ctcgagctc                          1719
```

<210> SEQ ID NO 7
<211> LENGTH: 562
<212> TYPE: PRT
<213> ORGANISM: Artificial Sequence
<220> FEATURE:
<223> OTHER INFORMATION: Influenza H2 amino acid sequence

<400> SEQUENCE: 7

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
```

```
                100             105             110
Tyr Glu Glu Leu Lys His Leu Leu Ser Ser Val Lys His Phe Glu Lys
            115                 120                 125

Val Lys Ile Leu Pro Lys Asp Arg Trp Thr Gln His Thr Thr Thr Gly
            130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
            195                 200                 205

Gly Thr Tyr Val Ser Val Gly Thr Ser Thr Leu Asn Lys Arg Ser Thr
            210                 215                 220

Pro Glu Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
                260                 265                 270

Arg Gly Ser Ser Gly Ile Met Lys Thr Glu Gly Thr Leu Glu Asn Cys
            275                 280                 285

Glu Thr Lys Cys Gln Thr Pro Leu Gly Ala Ile Asn Thr Thr Leu Pro
            290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
            355                 360                 365

Asp Gln Gly Ser Gly Tyr Ala Ala Asp Lys Glu Ser Thr Gln Lys Ala
            370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
            435                 440                 445

Asp Phe His Asp Ser Asn Val Lys Asn Leu Tyr Asp Lys Val Arg Met
450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Ser Lys Leu Asn Arg Asn Glu
            500                 505                 510

Ile Lys Gly Val Lys Leu Ser Ser Met Gly Val Tyr Gln Ile Leu Ala
            515                 520                 525
```

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile

<210> SEQ ID NO 8
<211> LENGTH: 4628
<212> TYPE: DNA
<213> ORGANISM: Artificial Sequence
<220> FEATURE:
<223> OTHER INFORMATION: pGX2006 H2HA DNA sequence

<400> SEQUENCE: 8

| | | | | | |
|---|---|---|---|---|---|
| gactcttcgc | gatgtacggg | ccagatatac | gcgttgacat | tgattattga | ctagttatta | 60 |
| atagtaatca | attacggggt | cattagttca | tagcccatat | atggagttcc | gcgttacata | 120 |
| acttacggta | aatggcccgc | ctggctgacc | gcccaacgac | ccccgcccat | tgacgtcaat | 180 |
| aatgacgtat | gttcccatag | taacgccaat | agggactttc | cattgacgtc | aatgggtgga | 240 |
| gtatttacgg | taaactgccc | acttggcagt | acatcaagtg | tatcatatgc | caagtacgcc | 300 |
| ccctattgac | gtcaatgacg | gtaaatggcc | cgcctggcat | tatgcccagt | acatgacctt | 360 |
| atgggacttt | cctacttggc | agtacatcta | cgtattagtc | atcgctatta | ccatggtgat | 420 |
| gcggttttgg | cagtacatca | atgggcgtgg | atagcggttt | gactcacggg | gatttccaag | 480 |
| tctccacccc | attgacgtca | atgggagttt | gttttggcac | caaaatcaac | gggactttcc | 540 |
| aaaatgtcgt | aacaactccg | ccccattgac | gcaaatgggc | ggtaggcgtg | tacggtggga | 600 |
| ggtctatata | agcagagctc | tctggctaac | tagagaaccc | actgcttact | ggcttatcga | 660 |
| aattaatacg | actcactata | gggagaccca | agctggctag | cgtttaaact | taagcttgcc | 720 |
| accatggcca | tcatctacct | gatcctgctg | ttcaccgccg | tgcggggcga | ccagatctgc | 780 |
| atcggctacc | acgccaacaa | cagcaccgag | aaggtggaca | ccatcctgga | acggaacgtg | 840 |
| accgtgaccc | acgccaagga | catcctggaa | aagaccacaa | acggcaagct | gtgcaagctg | 900 |
| aacggcatcc | ccccctgga | actgggcgac | tgcagcattg | ccggctggct | gctgggcaac | 960 |
| cccgagtgcg | accggctgct | gtccgtgccc | gagtggagct | acatcatgga | aaaagagaac | 1020 |
| ccccgggacg | gcctgtgcta | ccccggcagc | ttcaacgact | acgaggaact | gaagcacctg | 1080 |
| ctgtccagcg | tgaagcactt | cgagaaggtg | aaaatcctgc | caaggaccg | gtggacccag | 1140 |
| cacaccacca | ccggcggcag | cagagcctgt | gccgtgagcg | gcaaccccag | cttcttccgg | 1200 |
| aacatggtgt | ggctgaccaa | gaagggcagc | aactacccg | tggccaaggg | cagctacaac | 1260 |
| aacacctccg | gagaacagat | gctgatcatc | tggggcgtgc | accacccaa | cgacgagaca | 1320 |
| gagcagcgga | ccctgtacca | gaacgtgggc | acctacgtga | gcgtgggcac | cagcacctg | 1380 |
| aacaagcgga | gcacccccga | gatcgccacc | cggcccaagg | tgaacggcct | gggcagccgg | 1440 |
| atggaattca | gctggaccct | gctggacatg | tgggacacca | tcaacttcga | gagcaccggc | 1500 |
| aacctgatcg | ccccgagta | cggcttcaag | atcagcaagc | ggggcagcag | cggcatcatg | 1560 |
| aaaaccgagg | gcaccctgga | aaactgcgag | acaaagtgcc | agacccccct | gggcgccatc | 1620 |
| aacaccaccc | tgcccttcca | caacgtgcac | ccctgacca | tcggcgagtg | cccaagtac | 1680 |
| gtgaagagcg | agaagctggt | gctggccacc | ggcctgcgga | acgtgcccca | gatcgagagc | 1740 |
| aggggcctgt | tcggcgccat | tgccggattc | atcgagggcg | gctggcaggg | catggtggac | 1800 |

```
gggtggtacg gctaccacca cagcaacgac cagggcagcg gctacgccgc cgacaaagag    1860
agcacccaga aggccttcga cggcatcacc aacaaggtga acagcgtgat cgagaagatg    1920
aacacccagt tcgaggccgt gggcaaagag ttcagcaacc tggaacggcg gctggaaaac    1980
ctgaacaaga aaatggaaga tggcttcctg gacgtgtgga cctacaacgc cgagctgctg    2040
gtgctgatgg aaaacgagag gaccctggac ttccacgaca gcaacgtgaa gaacctgtac    2100
gacaaagtgc ggatgcagct gcgggacaac gtgaaagagc tgggcaacgg ctgcttcgag    2160
ttctaccaca gtgcgacga cgagtgcatg aactccgtga agaacggcac ctacgactac    2220
cctaagtacg aggaagagtc caagctgaac cggaacgaga tcaagggcgt gaagctgtcc    2280
agcatgggcg tgtaccagat cctggccatc tacgccaccg tggccggcag cctgagcctg    2340
gctattatga tggctggcat cagcttttgg atgtgcagca acggcagcct gcagtgccgg    2400
atctgcatct gatgactcga gtctagaggg cccgtttaaa cccgctgatc agcctcgact    2460
gtgccttcta gttgccagcc atctgttgtt tgccc ctccc ccgtgccttc cttgaccctg    2520
gaaggtgcca ctcccactgt cctttcctaa taaaatgagg aaattgcatc gcattgtctg    2580
agtaggtgtc attctattct ggggggtggg gtggggcagg acagcaaggg ggaggattgg    2640
gaagacaata gcaggcatgc tggggatgcg gtgggctcta tggcttctac tgggcggttt    2700
tatggacagc aagcgaaccg gaattgccag ctggggcgcc ctctggtaag gttgggaagc    2760
cctgcaaagt aaactggatg gctttcttgc cgccaaggat ctgatggcgc aggggatcaa    2820
gctctgatca agagacagga tgaggatcgt ttcgcatgat tgaacaagat ggattgcacg    2880
caggttctcc ggccgcttgg gtggagaggc tattcggcta tgactgggca acagacaa     2940 tcggctgctc tgatgccgcc gtgttccggc tgtcagcgca ggggcgcccg gttcttttg     3000 tcaagaccga cctgtccggt gccctgaatg aactgcaaga cgaggcagcg cggctatcgt    3060
ggctggccac gacgggcgtt ccttgcgcag ctgtgctcga cgttgtcact gaagcgggaa    3120
gggactggct gctattgggc gaagtgccgg ggcaggatct cctgtcatct caccttgctc    3180
ctgccgagaa agtatccatc atggctgatg caatgcggcg gctgcatacg cttgatccgg    3240
ctacctgccc attcgaccac caagcgaaac atcgcatcga gcgagcacgt actcggatgg    3300
aagccggtct tgtcgatcag gatgatctgg acgaagagca tcaggggctc gcgccagccg    3360
aactgttcgc caggctcaag gcgagcatgc ccgacggcga ggatctcgtc gtgacccatg    3420
gcgatgcctg cttgccgaat atcatggtgg aaaatggccg cttttctgga ttcatcgact    3480
gtggccggct gggtgtggcg gaccgctatc aggacatagc gttggctacc cgtgatattg    3540
ctgaagagct tggcggcgaa tgggctgacc gcttcctcgt gctttacggt atcgccgctc    3600
ccgattcgca gcgcatcgcc ttctatcgcc ttcttgacga gttcttctga attattaacg    3660
cttacaattt cctgatgcgg tattttctcc ttacgcatct gtgcggtatt tcacaccgca    3720
tcaggtggca cttttcgggg aaatgtgcgc ggaacccta tttgtttatt tttctaaata    3780
cattcaaata tgtatccgct catgagacaa taaccctgat aaatgcttca ataatagcac    3840
gtgctaaaac ttcatttta atttaaaagg atctaggtga agatccttt tgataatctc     3900 atgaccaaaa tcccttaacg tgagttttcg ttccactgag cgtcagaccc cgtagaaaag    3960
atcaaaggat cttcttgaga tccttttttt ctgcgcgtaa tctgctgctt gcaaacaaaa    4020
aaaccaccgc taccagcggt ggtttgtttg ccggatcaag agctaccaac tcttttccg     4080 aaggtaactg gcttcagcag agcgcagata ccaaatactg ttcttctagt gtagccgtag    4140
ttaggccacc acttcaagaa ctctgtagca ccgcctacat acctcgctct gctaatcctg    4200
```

```
ttaccagtgg ctgctgccag tggcgataag tcgtgtctta ccgggttgga ctcaagacga    4260
tagttaccgg ataaggcgca gcggtcgggc tgaacggggg gttcgtgcac acagcccagc    4320
ttggagcgaa cgacctacac cgaactgaga tacctacagc gtgagctatg agaaagcgcc    4380
acgcttcccg aagggagaaa ggcggacagg tatccgtaa gcggcagggt cggaacagga     4440
gagcgcacga gggagcttcc aggggggaaac gcctggtatc tttatagtcc tgtcgggttt   4500
cgccacctct gacttgagcg tcgattttg tgatgctcgt caggggggcg agcctatgg      4560 aaaaacgcca gcaacgcggc cttttacgg ttcctggcct tttgctggcc ttttgctcac     4620
atgttctt                                                             4628
```

<210> SEQ ID NO 9
<211> LENGTH: 1695
<212> TYPE: DNA
<213> ORGANISM: Artificial Sequence
<220> FEATURE:
<223> OTHER INFORMATION: Influenza U2 DNA sequence

<400> SEQUENCE: 9

```
aaggccaagc tgctggtgct gctgtgcacc ttcgccgcca ccaacgccga caccatctgc      60
atcggctacc acgccaacaa cagcaccgac accgtggata ccgtgctgga aaagaacgtg     120
accgtgaccc cagcgtgaa cctgctggaa gataagcaca acggcaagct gtgcaagctg      180
aagggaatcg ccccctgca gctgggcaag tgcaatatcg ccggctggat tctgggcaac     240
cccgagtgcg agagcctgag cagcaagagc agctggtcct acatcgtgga accccccaac   300
agcgagaacg gcacctgtta ccccggcgac ttcgccgact acgaggaact gcgcgagcag   360
ctgagcagcg tgtccagctt cgagagattc gagatcttcc ccaagaccag cagctggccc   420
aaccacgacg tgaccaaggg cgtgaccgct agctgtagcc acgcaggcgc cagcagcttc   480
tacaagaacc tgctgtggct gaccaagaag aacggcagct accccaagct gagcaagagc   540
tacatcaaca acaaagaaaa agaggtgctg gtcctctggg gcgtccacca ccccagcaca   600
atcgccgacc agcagagcct gtaccagaac gagaacgcct acgtgtccgt gggcagcagc   660
cactacagcc ggaagttcac ccccgagatc gccaagcggc ccaaagtgcg ggaccaggaa   720
ggccggatca actactactg gaccctgctg gaacccggcg acaccatcat cttcgaggcc   780
aacggcaacc tgatcgcccc cagatacgcc ttcgccctga gcagaggctt cggcagcggc   840
atcatcatca gcaacgcccc catgcacgac tgcgacacca gtgccagac ccctcagggc   900 gccatcaaca gcagcctgcc cttccagaac atcacccccg tgaccatcgg cgagtgcccc   960
aaatacgtgc ggagcaccaa gctgcggatg gccaccggcc tgcggaacat ccccagcatc  1020
cagagcagag gcctgttcgg cgccattgcc ggcttcatcg agggcggctg gaccggaatg  1080
gtggacgggt ggtacggcta ccaccaccag aatgagcagg gcagcggcta cgccgccgac  1140
cagaagtcca cccagaacgc catcgacggc atcaccaaca agtgaacag cgtgatcgag   1200 aagatgaaca cccagttcac cgccgtgggc aaagagttca caagctgga aaagcggatg   1260 gaaaacctga caagaaggt ggacgacggc ttcctggaca tctggaccta caacgccgaa   1320
ctgctcgtgc tgctggaaaa cgagcggacc ctggacttcc acgacagcaa cgtgaagaac  1380
ctgtacgaga aagtgaagtc ccagctgaag aacaacgcca agagatcgg caacggctgc   1440 ttcgagttct accacaagtg caacaacgag tgcatggaaa gcgtgaagaa cggaacctac   1500
gactacccca gtacagcga ggaaagcaag ctgaaccggg aagagatcga cggcgtgaag   1560
```

-continued

```
ctggaatcca tgggcgtgta ccagatcctg gccatctaca gcaccgtggc tagcagcctg      1620
gtgctgctgg tgtccctggg cgccatctcc ttttggatgt gctccaacgg cagcctgcag      1680
tgccggatct gcatc                                                      1695
```

<210> SEQ ID NO 10
<211> LENGTH: 565
<212> TYPE: PRT
<213> ORGANISM: Artificial Sequence
<220> FEATURE:
<223> OTHER INFORMATION: Influenza U2 amino acid sequence

<400> SEQUENCE: 10

```
Lys Ala Lys Leu Leu Val Leu Leu Cys Thr Phe Ala Ala Thr Asn Ala
1               5                   10                  15

Asp Thr Ile Cys Ile Gly Tyr His Ala Asn Asn Ser Thr Asp Thr Val
                20                  25                  30

Asp Thr Val Leu Glu Lys Asn Val Thr Val Thr His Ser Val Asn Leu
            35                  40                  45

Leu Glu Asp Lys His Asn Gly Lys Leu Cys Lys Leu Lys Gly Ile Ala
    50                  55                  60

Pro Leu Gln Leu Gly Lys Cys Asn Ile Ala Gly Trp Ile Leu Gly Asn
65                  70                  75                  80

Pro Glu Cys Glu Ser Leu Ser Ser Lys Ser Ser Trp Ser Tyr Ile Val
                85                  90                  95

Glu Thr Pro Asn Ser Glu Asn Gly Thr Cys Tyr Pro Gly Asp Phe Ala
                100                 105                 110

Asp Tyr Glu Glu Leu Arg Glu Gln Leu Ser Ser Val Ser Ser Phe Glu
            115                 120                 125

Arg Phe Glu Ile Phe Pro Lys Thr Ser Ser Trp Pro Asn His Asp Val
    130                 135                 140

Thr Lys Gly Val Thr Ala Ser Cys Ser His Ala Gly Ala Ser Ser Phe
145                 150                 155                 160

Tyr Lys Asn Leu Leu Trp Leu Thr Lys Lys Asn Gly Ser Tyr Pro Lys
                165                 170                 175

Leu Ser Lys Ser Tyr Ile Asn Asn Lys Glu Lys Glu Val Leu Val Leu
            180                 185                 190

Trp Gly Val His His Pro Ser Thr Ile Ala Asp Gln Gln Ser Leu Tyr
        195                 200                 205

Gln Asn Glu Asn Ala Tyr Val Ser Val Gly Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
                260                 265                 270

Leu Ser Arg Gly Phe Gly Ser Gly Ile Ile Ile Ser Asn Ala Pro Met
            275                 280                 285

His Asp Cys Asp Thr Lys Cys Gln Thr Pro Gln Gly Ala Ile Asn Ser
    290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Ala Thr Gly Leu Arg Asn
                325                 330                 335
```

-continued

```
Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asp Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Lys Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
    450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asn Glu Cys Met Glu Ser Val Lys
                485                 490                 495
Asn Gly Thr Tyr Asp Tyr Pro Lys Tyr Ser Glu Glu Ser Lys Leu Asn
            500                 505                 510
Arg Glu Glu Ile Asp Gly Val Lys Leu Glu Ser Met Gly Val Tyr Gln
        515                 520                 525
Ile Leu Ala Ile Tyr Ser Thr Val Ala Ser Ser Leu Val Leu Leu Val
    530                 535                 540
Ser Leu Gly Ala Ile Ser Phe Trp Met Cys Ser Asn Gly Ser Leu Gln
545                 550                 555                 560
Cys Arg Ile Cys Ile
                565

<210> SEQ ID NO 11
<211> LENGTH: 1809
<212> TYPE: DNA
<213> ORGANISM: Artificial Sequence
<220> FEATURE:
<223> OTHER INFORMATION: IgE-U2-HATAntigen DNA Sequence

<400> SEQUENCE: 11
ggtaccggat ccgccaccat ggactggacc tggattctgt tcctggtcgc cgctgctacc      60
cgggtgcact ctaaggccaa gctgctggtg ctgctgtgca ccttcgccgc caccaacgcc     120
gacaccatct gcatcggcta ccacgccaac aacagcaccg acaccgtgga taccgtgctg     180
gaaaagaacg tgaccgtgac ccacagcgtg aacctgctgg aagataagca caacggcaag     240
ctgtgcaagc tgaagggaat cgccccccctg cagctgggca agtgcaatat cgccggctgg    300
attctgggca accccgagtg cgagagcctg agcagcaaga gcagctggtc ctacatcgtg     360
gaaaccccca acagcgagaa cggcacctgt taccccggcg acttcgccga ctacgaggaa     420
ctgcgcgagc agctgagcag cgtgtccagc ttcgagagat tcgagatctt ccccaagacc     480
agcagctggc ccaaccacga cgtgaccaag ggcgtgaccg ctagctgtag ccacgcaggc     540
gccagcagct tctacaagaa cctgctgtgg ctgaccaaga agaacggcag ctaccccaag     600
ctgagcaaga gctacatcaa caacaaagaa aaagaggtgc tggtcctctg gggcgtccac     660
caccccagca caatcgccga ccagcagagc ctgtaccaga acgagaacgc ctacgtgtcc     720
```

-continued

```
gtgggcagca gccactacag ccggaagttc accccgaga tcgccaagcg gcccaaagtg      780
cgggaccagg aaggccggat caactactac tggaccctgc tggaacccgg cgacaccatc      840
atcttcgagg ccaacggcaa cctgatcgcc cccagatacg ccttcgccct gagcagaggc      900
ttcggcagcg gcatcatcat cagcaacgcc cccatgcacg actgcgacac caagtgccag      960
accccctcagg gcgccatcaa cagcagcctg cccttccaga catccacccc cgtgaccatc     1020
ggcgagtgcc ccaaatacgt gcggagcacc aagctgcgga tggccaccgg cctgcggaac     1080
atccccagca tccagagcag aggcctgttc ggcgccattg ccggcttcat cgagggcggc     1140
tggaccggaa tggtggacgg cgtggtacgg caccaccacc agaatgagca gggcagcggc     1200
tacgccgccg accagaagtc cacccagaac gccatcgacg catcaccaa caaagtgaac      1260
agcgtgatcg agaagatgaa cacccagttc accgccgtgg gcaaagagtt caacaagctg     1320
gaaaagcgga tggaaaacct gaacaagaag gtggacgacg gcttcctgga catctggacc     1380
tacaacgccg aactgctcgt gctgctggaa aacgagcgga ccctggactt ccacgacagc     1440
aacgtgaaga acctgtacga aaagtgaag tcccagctga gaacaacgc caagagatc        1500
ggcaacggct gcttcgagtt ctaccacaag tgcaacaacg agtgcatgga aagcgtgaag     1560
aacggaacct acgactaccc caagtacagc gaggaaagca gctgaaccg gaagagatc       1620
gacggcgtga gctggaatc catgggcgtg taccagatcc tggccatcta cagcaccgtg     1680
gctagcagcc tggtgctgct ggtgtccctg ggcgccatct cctttggat gtgctccaac      1740
ggcagcctgc agtgccggat ctgcatctac ccctacgacg tgcccgacta cgcctgatga     1800
ctcgagctc                                                             1809
```

<210> SEQ ID NO 12
<211> LENGTH: 592
<212> TYPE: PRT
<213> ORGANISM: Artificial Sequence
<220> FEATURE:
<223> OTHER INFORMATION: IgE-U2-HATantigen amino acid Sequence

<400> SEQUENCE: 12

Met Asp Trp Thr Trp Ile Leu Phe Leu Val Ala Ala Thr Arg Val
1               5                   10                  15

His Ser Lys Ala Lys Leu Leu Val Leu Leu Cys Thr Phe Ala Ala Thr
            20                  25                  30

Asn Ala Asp Thr Ile Cys Ile Gly Tyr His Ala Asn Asn Ser Thr Asp
        35                  40                  45

Thr Val Asp Thr Val Leu Glu Lys Asn Val Thr Val Thr His Ser Val
    50                  55                  60

Asn Leu Leu Glu Asp Lys His Asn Gly Lys Leu Cys Lys Leu Lys Gly
65                  70                  75                  80

Ile Ala Pro Leu Gln Leu Gly Lys Cys Asn Ile Ala Gly Trp Ile Leu
                85                  90                  95

Gly Asn Pro Glu Cys Glu Ser Leu Ser Ser Lys Ser Ser Trp Ser Tyr
            100                 105                 110

Ile Val Glu Thr Pro Asn Ser Glu Asn Gly Thr Cys Tyr Pro Gly Asp
        115                 120                 125

Phe Ala Asp Tyr Glu Glu Leu Arg Glu Gln Leu Ser Ser Val Ser Ser
    130                 135                 140

Phe Glu Arg Phe Glu Ile Phe Pro Lys Thr Ser Ser Trp Pro Asn His
145                 150                 155                 160

Asp Val Thr Lys Gly Val Thr Ala Ser Cys Ser His Ala Gly Ala Ser

```
            165                 170                 175
Ser Phe Tyr Lys Asn Leu Leu Trp Leu Thr Lys Lys Asn Gly Ser Tyr
                180                 185                 190
Pro Lys Leu Ser Lys Ser Tyr Ile Asn Asn Lys Glu Lys Glu Val Leu
            195                 200                 205
Val Leu Trp Gly Val His His Pro Ser Thr Ile Ala Asp Gln Gln Ser
    210                 215                 220
Leu Tyr Gln Asn Glu Asn Ala Tyr Val Ser Val Gly Ser Ser His Tyr
225                 230                 235                 240
Ser Arg Lys Phe Thr Pro Glu Ile Ala Lys Arg Pro Lys Val Arg Asp
                245                 250                 255
Gln Glu Gly Arg Ile Asn Tyr Tyr Trp Thr Leu Leu Glu Pro Gly Asp
                260                 265                 270
Thr Ile Ile Phe Glu Ala Asn Gly Asn Leu Ile Ala Pro Arg Tyr Ala
                275                 280                 285
Phe Ala Leu Ser Arg Gly Phe Gly Ser Gly Ile Ile Ser Asn Ala
            290                 295                 300
Pro Met His Asp Cys Asp Thr Lys Cys Gln Thr Pro Gln Gly Ala Ile
305                 310                 315                 320
Asn Ser Ser Leu Pro Phe Gln Asn Ile His Pro Val Thr Ile Gly Glu
                325                 330                 335
Cys Pro Lys Tyr Val Arg Ser Thr Lys Leu Arg Met Ala Thr Gly Leu
                340                 345                 350
Arg Asn Ile Pro Ser Ile Gln Ser Arg Gly Leu Phe Gly Ala Ile Ala
                355                 360                 365
Gly Phe Ile Glu Gly Gly Trp Thr Gly Met Val Asp Gly Trp Tyr Gly
            370                 375                 380
Tyr His His Gln Asn Glu Gln Gly Ser Gly Tyr Ala Ala Asp Gln Lys
385                 390                 395                 400
Ser Thr Gln Asn Ala Ile Asp Gly Ile Thr Asn Lys Val Asn Ser Val
                405                 410                 415
Ile Glu Lys Met Asn Thr Gln Phe Thr Ala Val Gly Lys Glu Phe Asn
                420                 425                 430
Lys Leu Glu Lys Arg Met Glu Asn Leu Asn Lys Lys Val Asp Asp Gly
            435                 440                 445
Phe Leu Asp Ile Trp Thr Tyr Asn Ala Glu Leu Leu Val Leu Leu Glu
            450                 455                 460
Asn Glu Arg Thr Leu Asp Phe His Asp Ser Asn Val Lys Asn Leu Tyr
465                 470                 475                 480
Glu Lys Val Lys Ser Gln Leu Lys Asn Asn Ala Lys Glu Ile Gly Asn
                485                 490                 495
Gly Cys Phe Glu Phe Tyr His Lys Cys Asn Asn Glu Cys Met Glu Ser
                500                 505                 510
Val Lys Asn Gly Thr Tyr Asp Tyr Pro Lys Tyr Ser Glu Glu Ser Lys
            515                 520                 525
Leu Asn Arg Glu Glu Ile Asp Gly Val Lys Leu Glu Ser Met Gly Val
            530                 535                 540
Tyr Gln Ile Leu Ala Ile Tyr Ser Thr Val Ala Ser Ser Leu Val Leu
545                 550                 555                 560
Leu Val Ser Leu Gly Ala Ile Ser Phe Trp Met Cys Ser Asn Gly Ser
                565                 570                 575
Leu Gln Cys Arg Ile Cys Ile Tyr Pro Tyr Asp Val Pro Asp Tyr Ala
            580                 585                 590
```

<210> SEQ ID NO 13
<211> LENGTH: 1749
<212> TYPE: DNA
<213> ORGANISM: Artificial Sequence
<220> FEATURE:
<223> OTHER INFORMATION: BHA DNA Sequence

<400> SEQUENCE: 13

```
aaggccatca tcgtgctgct gatggtggtc acaagcaacg ccgaccggat ctgcaccggc      60
atcaccagca gcaacagccc ccacgtggtc aaaaccgcca cccagggcga agtgaacgtg     120
accggcgtga tccccctgac caccaccccc accaagagcc acttcgccaa cctgaagggc     180
accaagaccc ggggaaagct gtgccccaag tgcctgaact gcaccgacct ggacgtggcc     240
ctgggcagac ctatgtgcgt gggcaccacc cctagcgcca aggccagcat cctgcacgaa     300
gtgcggcccg tgaccagcgg ctgcttcccc atcatgcacg accggaccaa gatccggcag     360
ctccccaacc tgctgcgggg ctacgagaac atccggctga gcacccagaa cgtgatcaac     420
gccgagaagg cccctggcgg cccttacaga ctgggcacaa gcggctcttg ccccaacgcc     480
accagcaaga gcggcttttt cgccacaatg gcctgggccg tgcccaagga caacaacaag     540
accgccacca ccccctgac cgtggaagtg ccctacatct gcaccgaggg cgaggaccag     600
atcaccgtgt ggggcttcca cagcgataac aagacccaga tgaagaacct gtacggcgac     660
agcaaccccc agaagttcac cagctccgcc aacggcgtga ccacccacta cgtgtcccag     720
atcggcggct tccccgacca gacagaggat ggcggcctgc cccagagcgg cagaatcgtg     780
gtggactaca tggtgcagaa gcccggcaag accggcacca tcgtgtacca gcggggcatc     840
ctgctgcccc agaaagtgtg gtgcgccagc ggccggtcca agtgatcaa gggcagcctg     900
cctctgatcg gcgaggccga ttgcctgcac gagaagtacg gcggcctgaa caagagcaag     960
ccctactaca ccggcgagca cgccaaagcc atcggcaact gccccatctg ggtcaaaacc    1020
cccctgaagc tggccaacgg caccaagtac cggcctcccg ccaagctgct gaaagagcgg    1080
ggcttcttcg gcgctatcgc cggctttctg gaaggcggct gggagggcat gatcgccggc    1140
tggcacggct acacatctca cggcgctcat ggcgtggccg tggccgctga tctgaagtcc    1200
acccaggaag ccatcaacaa gatcaccaag aacctgaaca gcctgagcga gctggaagtg    1260
aagaatctgc agcggctgag cggcgccatg gacgagctgc acaacgagat cctggaactg    1320
gacgagaagg tggacgacct gcgggccgac accatctcca gccagatcga gctggccgtg    1380
ctgctgtcca acgagggcat catcaacagc gaggacgagc atcctggc cctggaacgg    1440
aagctgaaga gatgctgggc cctagcgcc gtggacatcg caacggctg cttcgagaca    1500
aagcacaagt gcaaccagac ctgcctggac cggatcgctg ccggcacctt caacgccggc    1560
gagttcagcc tgcccacctt cgacagcctg aacatcaccg ccgccagcct gaacgacgac    1620
ggcctggaca accacaccat cctgctgtac tacagcaccg cagcctccag cctggccgtg    1680
accctgatga tcgccatctt catcgtgtac atggtgtctc gggacaacgt gtcctgcagc    1740
atctgcctg                                                           1749
```

<210> SEQ ID NO 14
<211> LENGTH: 583
<212> TYPE: PRT
<213> ORGANISM: Artificial Sequence
<220> FEATURE:
<223> OTHER INFORMATION: BHA Amino Acid Sequence

<400> SEQUENCE: 14

```
Lys Ala Ile Ile Val Leu Leu Met Val Thr Ser Asn Ala Asp Arg
1               5                   10                  15

Ile Cys Thr Gly Ile Thr Ser Ser Asn Ser Pro His Val Val Lys Thr
                20                  25                  30

Ala Thr Gln Gly Glu Val Asn Val Thr Gly Val Ile Pro Leu Thr Thr
            35                  40                  45

Thr Pro Thr Lys Ser His Phe Ala Asn Leu Lys Gly Thr Lys Thr Arg
        50                  55                  60

Gly Lys Leu Cys Pro Lys Cys Leu Asn Cys Thr Asp Leu Asp Val Ala
65                  70                  75                  80

Leu Gly Arg Pro Met Cys Val Gly Thr Thr Pro Ser Ala Lys Ala Ser
                85                  90                  95

Ile Leu His Glu Val Arg Pro Val Thr Ser Gly Cys Phe Pro Ile Met
            100                 105                 110

His Asp Arg Thr Lys Ile Arg Gln Leu Pro Asn Leu Leu Arg Gly Tyr
        115                 120                 125

Glu Asn Ile Arg Leu Ser Thr Gln Asn Val Ile Asn Ala Glu Lys Ala
130                 135                 140

Pro Gly Gly Pro Tyr Arg Leu Gly Thr Ser Gly Ser Cys Pro Asn Ala
145                 150                 155                 160

Thr Ser Lys Ser Gly Phe Phe Ala Thr Met Ala Trp Ala Val Pro Lys
                165                 170                 175

Asp Asn Asn Lys Thr Ala Thr Asn Pro Leu Thr Val Glu Val Pro Tyr
            180                 185                 190

Ile Cys Thr Glu Gly Glu Asp Gln Ile Thr Val Trp Gly Phe His Ser
        195                 200                 205

Asp Asn Lys Thr Gln Met Lys Asn Leu Tyr Gly Asp Ser Asn Pro Gln
210                 215                 220

Lys Phe Thr Ser Ser Ala Asn Gly Val Thr Thr His Tyr Val Ser Gln
225                 230                 235                 240

Ile Gly Gly Phe Pro Asp Gln Thr Glu Asp Gly Gly Leu Pro Gln Ser
                245                 250                 255

Gly Arg Ile Val Val Asp Tyr Met Val Gln Lys Pro Gly Lys Thr Gly
            260                 265                 270

Thr Ile Val Tyr Gln Arg Gly Ile Leu Leu Pro Gln Lys Val Trp Cys
        275                 280                 285

Ala Ser Gly Arg Ser Lys Val Ile Lys Gly Ser Leu Pro Leu Ile Gly
290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
        355                 360                 365

Phe Leu Glu Gly Gly Trp Glu Gly Met Ile Ala Gly Trp His Gly Tyr
370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415
```

-continued

```
Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580

<210> SEQ ID NO 15
<211> LENGTH: 1865
<212> TYPE: DNA
<213> ORGANISM: Artificial Sequence
<220> FEATURE:
<223> OTHER INFORMATION: IgE-BHA-HATantigen DNA Sequence

<400> SEQUENCE: 15
ggtaccggat ccgccaccat ggactggacc tggattctgt tcctggtggc cgctgccaca      60
cgggtgcaca gcaaggccat catcgtgctg ctgatggtgg tcacaagcaa cgccgaccgg     120
atctgcaccg gcatcaccag cagcaacagc ccccacgtgg tcaaaaccgc cacccagggc     180
gaagtgaacg tgaccggcgt gatccccctg accaccaccc ccaccaagag ccacttcgcc     240
aacctgaagg gcaccaagac ccggggaaag ctgtgcccca agtgcctgaa ctgcaccgac     300
ctggacgtgg ccctgggcag acctatgtgc gtgggcacca cccctagcgc caaggccagc     360
atcctgcacg aagtgcggcc cgtgaccagc ggctgcttcc ccatcatgca cgaccggacc     420
aagatccggc agctccccaa cctgctgcgg ggctacgaga acatccggct gagcacccag     480
aacgtgatca acgccgagaa ggcccctggc ggcccttaca gactgggcac aagcggctct     540
tgccccaacg ccaccagcaa gagcggcttt ttcgccacaa tggcctgggc cgtgcccaag     600
gacaacaaca agaccgccac caaccccctg accgtggaag tgccctacat ctgcaccgag     660
ggcgaggacc agatcaccgt gtggggcttc cacagcgata acaagaccca gatgaagaac     720
ctgtacggcg acagcaaccc ccagaagttc accagctccg ccaacggcgt gaccacccac     780
tacgtgtccc agatcggcgg cttccccgac cagacagagg atggcggcct gccccagagc     840
ggcagaatcg tggtggacta catggtgcag aagcccggca agaccggcac catcgtgtac     900
cagcggggca tcctgctgcc ccagaaagtg tggtgcgcca gcggccggtc caaagtgatc     960
aagggcagcc tgcctctgat cggcgaggcc gattgcctgc acgagaagta cggcggcctg    1020
aacaagagca agccctacta caccggcgag cacgccaaag ccatcggcaa ctgccccatc    1080
```

```
tgggtcaaaa ccccccctgaa gctggccaac ggcaccaagt accggcctcc cgccaagctg   1140
ctgaaagagc ggggcttctt cggcgctatc gccggctttc tggaaggcgg ctgggagggc   1200
atgatcgccg gctggcacgg ctacacatct cacggcgctc atggcgtggc cgtggccgct   1260
gatctgaagt ccacccagga agccatcaac aagatcacca agaacctgaa cagcctgagc   1320
gagctggaag tgaagaatct gcagcggctg agcggcgcca tggacgagct gcacaacgag   1380
atcctggaac tggacgagaa ggtggacgac ctgcgggccg acaccatctc cagccagatc   1440
gagctggccg tgctgctgtc caacgagggc atcatcaaca gcgaggacga gcatctgctg   1500
gccctggaac ggaagctgaa gaagatgctg ggccctagcg ccgtggacat cggcaacggc   1560
tgcttcgaga caaagcacaa gtgcaaccag acctgcctgg accggatcgc tgccggcacc   1620
ttcaacgccg gcgagttcag cctgcccacc ttcgacagcc tgaacatcac cgccgccagc   1680
ctgaacgacg acggcctgga caaccacacc atcctgctgt actacagcac cgcagcctcc   1740
agcctggccg tgaccctgat gatcgccatc ttcatcgtgt acatggtgtc tcgggacaac   1800
gtgtcctgca gcatctgcct gtacccctac gacgtgcccg actacgctga tgactcgagc   1860
tcctc                                                                1865
```

<210> SEQ ID NO 16
<211> LENGTH: 610
<212> TYPE: PRT
<213> ORGANISM: Artificial Sequence
<220> FEATURE:
<223> OTHER INFORMATION: IgE-BHA-HATantigen Amino Acid Sequence

<400> SEQUENCE: 16

```
Met Asp Trp Thr Trp Ile Leu Phe Leu Val Ala Ala Ala Thr Arg Val
1               5                   10                  15

His Ser Lys Ala Ile Ile Val Leu Leu Met Val Val Thr Ser Asn Ala
            20                  25                  30

Asp Arg Ile Cys Thr Gly Ile Thr Ser Ser Asn Ser Pro His Val Val
        35                  40                  45

Lys Thr Ala Thr Gln Gly Glu Val Asn Val Thr Gly Val Ile Pro Leu
    50                  55                  60

Thr Thr Thr Pro Thr Lys Ser His Phe Ala Asn Leu Lys Gly Thr Lys
65                  70                  75                  80

Thr Arg Gly Lys Leu Cys Pro Lys Cys Leu Asn Cys Thr Asp Leu Asp
                85                  90                  95

Val Ala Leu Gly Arg Pro Met Cys Val Gly Thr Thr Pro Ser Ala Lys
            100                 105                 110

Ala Ser Ile Leu His Glu Val Arg Pro Val Thr Ser Gly Cys Phe Pro
        115                 120                 125

Ile Met His Asp Arg Thr Lys Ile Arg Gln Leu Pro Asn Leu Leu Arg
    130                 135                 140

Gly Tyr Glu Asn Ile Arg Leu Ser Thr Gln Asn Val Ile Asn Ala Glu
145                 150                 155                 160

Lys Ala Pro Gly Gly Pro Tyr Arg Leu Gly Thr Ser Gly Ser Cys Pro
                165                 170                 175

Asn Ala Thr Ser Lys Ser Gly Phe Phe Ala Thr Met Ala Trp Ala Val
            180                 185                 190

Pro Lys Asp Asn Asn Lys Thr Ala Thr Asn Pro Leu Thr Val Glu Val
        195                 200                 205

Pro Tyr Ile Cys Thr Glu Gly Glu Asp Gln Ile Thr Val Trp Gly Phe
```

His Ser Asp Asn Lys Thr Gln Met Lys Asn Leu Tyr Gly Asp Ser Asn
225                 230                 235                 240

Pro Gln Lys Phe Thr Ser Ser Ala Asn Gly Val Thr Thr His Tyr Val
            245                 250                 255

Ser Gln Ile Gly Gly Phe Pro Asp Gln Thr Glu Asp Gly Gly Leu Pro
                260                 265                 270

Gln Ser Gly Arg Ile Val Val Asp Tyr Met Val Gln Lys Pro Gly Lys
            275                 280                 285

Thr Gly Thr Ile Val Tyr Gln Arg Gly Ile Leu Leu Pro Gln Lys Val
        290                 295                 300

Trp Cys Ala Ser Gly Arg Ser Lys Val Ile Lys Gly Ser Leu Pro Leu
305                 310                 315                 320

Ile Gly Glu Ala Asp Cys Leu His Glu Lys Tyr Gly Gly Leu Asn Lys
                325                 330                 335

Ser Lys Pro Tyr Tyr Thr Gly Glu His Ala Lys Ala Ile Gly Asn Cys
                340                 345                 350

Pro Ile Trp Val Lys Thr Pro Leu Lys Leu Ala Asn Gly Thr Lys Tyr
            355                 360                 365

Arg Pro Pro Ala Lys Leu Leu Lys Glu Arg Gly Phe Phe Gly Ala Ile
        370                 375                 380

Ala Gly Phe Leu Glu Gly Gly Trp Glu Gly Met Ile Ala Gly Trp His
385                 390                 395                 400

Gly Tyr Thr Ser His Gly Ala His Gly Val Ala Val Ala Ala Asp Leu
                405                 410                 415

Lys Ser Thr Gln Glu Ala Ile Asn Lys Ile Thr Lys Asn Leu Asn Ser
            420                 425                 430

Leu Ser Glu Leu Glu Val Lys Asn Leu Gln Arg Leu Ser Gly Ala Met
        435                 440                 445

Asp Glu Leu His Asn Glu Ile Leu Glu Leu Asp Glu Lys Val Asp Asp
450                 455                 460

Leu Arg Ala Asp Thr Ile Ser Ser Gln Ile Glu Leu Ala Val Leu Leu
465                 470                 475                 480

Ser Asn Glu Gly Ile Ile Asn Ser Glu Asp Glu His Leu Leu Ala Leu
                485                 490                 495

Glu Arg Lys Leu Lys Lys Met Leu Gly Pro Ser Ala Val Asp Ile Gly
            500                 505                 510

Asn Gly Cys Phe Glu Thr Lys His Lys Cys Asn Gln Thr Cys Leu Asp
        515                 520                 525

Arg Ile Ala Ala Gly Thr Phe Asn Ala Gly Glu Phe Ser Leu Pro Thr
530                 535                 540

Phe Asp Ser Leu Asn Ile Thr Ala Ala Ser Leu Asn Asp Asp Gly Leu
545                 550                 555                 560

Asp Asn His Thr Ile Leu Leu Tyr Tyr Ser Thr Ala Ala Ser Ser Leu
                565                 570                 575

Ala Val Thr Leu Met Ile Ala Ile Phe Ile Val Tyr Met Val Ser Arg
            580                 585                 590

Asp Asn Val Ser Cys Ser Ile Cys Leu Tyr Pro Tyr Asp Val Pro Asp
        595                 600                 605

Tyr Ala
610

<210> SEQ ID NO 17

-continued

```
<211> LENGTH: 18
<212> TYPE: PRT
<213> ORGANISM: Artificial Sequence
<220> FEATURE:
<223> OTHER INFORMATION: IgE Leader Amino Acid Sequence

<400> SEQUENCE: 17

Met Asp Trp Thr Trp Ile Leu Phe Leu Val Ala Ala Thr Arg Val
1               5                   10                  15

His Ser

<210> SEQ ID NO 18
<211> LENGTH: 9
<212> TYPE: PRT
<213> ORGANISM: Artificial Sequence
<220> FEATURE:
<223> OTHER INFORMATION: HA tag amino acid sequence

<400> SEQUENCE: 18

Tyr Pro Tyr Asp Val Pro Asp Tyr Ala
1               5

<210> SEQ ID NO 19
<211> LENGTH: 1698
<212> TYPE: DNA
<213> ORGANISM: Artificial Sequence
<220> FEATURE:
<223> OTHER INFORMATION: pGX2012 H1HA-ConBris DNA Sequence

<400> SEQUENCE: 19
atgaaggtga aactgctggt gctgctgtgc accttcaccg ccacctacgc cgacaccatc      60
tgcatcggct accacgccaa caacagcacc gacaccgtgg ataccgtgct ggaaaagaac     120
gtgaccgtga cccacagcgt gaacctgctg aaaacagcc acaacggcaa gctgtgcctg     180
ctgaagggaa tcgcccccct gcagctgggc aattgcagcg tggccggctg gattctgggc     240
aaccccgagt gcgagctgct gatcagcaaa gagtcctggt cctacatcgt ggaaaagccc     300
aaccccgaga acggcacctg ttaccccggc cacttcgccg actacgagga actgcgcgag     360
cagctgagca gcgtgtccag cttcgagaga ttcgagatct cccccaaaga gtctagctgg     420
cccaaccaca ccgtgacagg cgtgtccgcc agctgctccc acaacggcga gagcagcttc     480
taccggaacc tgctgtggct gaccggcaag aacggcctgt accccaacct gagcaagagc     540
tatgccaaca caaagaaaa agaggtgctg gtgctgtggg gcgtgcacca ccccccaac     600 atcggcgacc agaaggccct gtaccacacc gagaacgcct acgtgtccgt ggtgtccagc     660
cactacagcc ggaagttcac ccccgagatc gccaagcggc ccaaagtgcg ggaccaggaa     720
ggccggatca actactactg gaccctgctg gaacccggcg acaccatcat cttcgaggcc     780
aacggcaacc tgatcgcccc cagatacgcc ttcgccctga cagaggctt cggcagcggc     840 atcatcaaca gcaacgcccc catggacaag tgcgacgcca gtgccagac cccccagggc     900 gccatcaaca gctccctgcc cttccagaac gtgcaccccg tgaccatcgg cgagtgcccc     960
aaatacgtgc ggagcgccaa gctgcggatg gtgacaggcc tgcggaacat cccccagcatc    1020 cagagcagag gcctgttcgg cgccattgcc ggcttcatcg agggcggctg gaccggaatg    1080
gtggacgggt ggtacggcta ccaccaccag aacgagcagg gcagcggcta cgccgccgac    1140
cagaagtcca cccagaacgc catcaacggc atcaccaaca agtgaacag cgtgatcgag    1200 aagatgaaca cccagttcac cgccgtgggc aagagttca acaagctgga acggcggatg    1260
gaaaacctga acaagaaggt ggacgacggc tttatcgaca tctggaccta caacgccgag    1320
```

```
ctgctggtcc tgctggaaaa cgagcggacc ctggacttcc acgacagcaa cgtgaagaac    1380
ctgtacgaga aagtgaagtc ccagctgaag aacaacgcca agagatcgg caacggctgc     1440 ttcgagttct accacaagtg caacgacgag tgcatggaaa gcgtgaagaa tggcacctac    1500
gactacccca gtacagcga ggaaagcaag ctgaaccgcg agaagatcga cggcgtgaag     1560
ctggaatcca tgggcgtgta ccagatcctg gccatctaca gcaccgtggc cagcagcctg    1620
gtcctgctgg tgtccctggg cgccatctcc ttttggatgt gctccaacgg cagcctgcag    1680
tgccggatct gcatctga                                                  1698
```

<210> SEQ ID NO 20
<211> LENGTH: 565
<212> TYPE: PRT
<213> ORGANISM: Artificial Sequence
<220> FEATURE:
<223> OTHER INFORMATION: pGX2012 H1HA-ConBris Protein Sequence

<400> SEQUENCE: 20

```
Met Lys Val Lys Leu Val Leu Leu Cys Thr Phe Thr Ala Thr Tyr
  1               5                  10                  15

Ala Asp Thr Ile Cys Ile Gly Tyr His Ala Asn Asn Ser Thr Asp Thr
                 20                  25                  30

Val Asp Thr Val Leu Glu Lys Asn Val Thr Val Thr His Ser Val Asn
             35                  40                  45

Leu Leu Glu Asn Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ile Ser Lys Glu Ser Trp Ser Tyr Ile
                 85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
            195                 200                 205

His Thr Glu Asn Ala Tyr Val Ser Val Val Ser Ser His Tyr Ser Arg
210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
            275                 280                 285
```

```
Asp Lys Cys Asp Ala Lys Cys Gln Thr Pro Gln Gly Ala Ile Asn Ser
    290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Gln Lys Ser Thr
370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Ile
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                485                 490                 495
Asn Gly Thr Tyr Asp Tyr Pro Lys Tyr Ser Glu Glu Ser Lys Leu Asn
            500                 505                 510
Arg Glu Lys Ile Asp Gly Val Lys Leu Glu Ser Met Gly Val Tyr Gln
        515                 520                 525
Ile Leu Ala Ile Tyr Ser Thr Val Ala Ser Ser Leu Val Leu Leu Val
530                 535                 540
Ser Leu Gly Ala Ile Ser Phe Trp Met Cys Ser Asn Gly Ser Leu Gln
545                 550                 555                 560
Cys Arg Ile Cys Ile
                565

<210> SEQ ID NO 21
<211> LENGTH: 1701
<212> TYPE: DNA
<213> ORGANISM: Artificial Sequence
<220> FEATURE:
<223> OTHER INFORMATION: pGX2015 H1HA-ConTT DNA Sequence

<400> SEQUENCE: 21
aaggcaaaac tgctggtgct gctgtgcgca ttcaccgcca catacgctga cacaatctgc      60
attggctatc acgccaacaa ttccactgac accgtggata ctgtcctgga gaagaacgtg     120
acagtcactc acagcgtgaa cctgctggaa gattcccata tggaaagct gtgccggctg      180 aaaggcatcg ctcctctgca gctggggaac tgctctgtgg cagggtggat ctgggaaat     240 ccagagtgtg aaagcctgtt ttccaaggag tcatggagct acatcgccga cccccaac      300 cctgaaaatg gcacatgcta ccctgggtat ttcgctgact atgaggaact gcgggagcag     360
ctgagctccg tgtctagttt cgagagattt gaaatcttcc caaggaatc aagctggccc     420 aaccacaccg tgacaaaggg agtcactgcc tcctgttctc ataacggcaa atcctctttt    480
```

```
taccgaaatc tgctgtggct gacagagaaa aacggcctgt acccaaatct gagtaagtca    540
tacgtgaaca ataaggagaa agaagtgctg gtcctgtggg gggtccacca tcectccaac    600 atcggagacc agcgcgccat ctaccacacc gagaatgctt acgtgagcgt ggtcagttca    660
cattacagcc ggcggttcac ccctgagatc gccaagcgac caaaagtgcg ggaccaggaa    720
ggcaggatta actactattg gactctgctg gagccagggg ataccatcat tttcgaagca    780
aacgaaaatc tgatcgcccc ctggtatgca tttgccctga gtcgcggatt cggctcaggg    840
atcattacct ctaatgcaag tatgggcgag tgcgatgcca agtgtcagac accacagggg    900
gctatcaaca gctccctgcc cttccagaat gtgcaccctg tcaccattgg agagtgcccc    960
aaatacgtga agcacaaa gctgaggatg gtcactggcc tgcgcaacat cccttcaatt    1020
cagagccgag gcctgtttgg ggctatcgca ggcttcattg agggcgggtg gaccgggatg   1080
atcgacggat ggtacggcta tcaccatcag aatgaacagg gatcaggcta cgccgctgat   1140
cagaagagca cacagaacgc aatcaatggg attactaaca aagtgaatag cgtcatcgag   1200
aagatgaaca ctcagtttac cgccgtggga aaggagttca acaagctgga gaggcgcatg   1260
gaaaacctga ataagaaagt ggacgatggc tttctggata tttggactta caacgctgag   1320
ctgctggtgc tgctggagaa tgaaagaacc ctggacttcc acgattccaa cgtgaagaat   1380
ctgtatgaaa aggtcaaatc tcagctgaag aacaatgcaa aagagatcgg aacggatgt    1440 ttcgagttct accataaatg caacaatgag tgtatggaat ctgtgaaaaa cgggacctac   1500
gactatccca gtattccga ggaatctaag ctgaataggg agaaaatcga tggagtgaag   1560
ctggaaagta tgggcgtcta ccagatcctg gctatctaca gcacagtggc atctagtctg   1620
gtgctgctgg tcagcctggg cgctatctcc ttctggatgt gctcaaatgg gtctctgcag   1680
tgccgcatct gtatctaatg a                                              1701
```

<210> SEQ ID NO 22
<211> LENGTH: 565
<212> TYPE: PRT
<213> ORGANISM: Artificial Sequence
<220> FEATURE:
<223> OTHER INFORMATION: pGX2015 H1HA-ConTT Protein Sequence

<400> SEQUENCE: 22

```
Lys Ala Lys Leu Leu Val Leu Leu Cys Ala Phe Thr Ala Thr Tyr Ala
1               5                   10                  15

Asp Thr Ile Cys Ile Gly Tyr His Ala Asn Asn Ser Thr Asp Thr Val
            20                  25                  30

Asp Thr Val Leu Glu Lys Asn Val Thr Val Thr His Ser Val Asn Leu
        35                  40                  45

Leu Glu Asp Ser His Asn Gly Lys Leu Cys Arg Leu Lys Gly Ile Ala
    50                  55                  60

Pro Leu Gln Leu Gly Asn Cys Ser Val Ala Gly Trp Ile Leu Gly Asn
65                  70                  75                  80

Pro Glu Cys Glu Ser Leu Phe Ser Lys Glu Ser Trp Ser Tyr Ile Ala
                85                  90                  95

Glu Thr Pro Asn Pro Glu Asn Gly Thr Cys Tyr Pro Gly Tyr Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Glu Ser Ser Trp Pro Asn His Thr Val
    130                 135                 140
```

```
Thr Lys Gly Val Thr Ala Ser Cys Ser His Asn Gly Lys Ser Ser Phe
145                 150                 155                 160

Tyr Arg Asn Leu Leu Trp Leu Thr Glu Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Ser Asn Ile Gly Asp Gln Arg Ala Ile Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Ser Met
        275                 280                 285

Gly Glu Cys Asp Ala Lys Cys Gln Thr Pro Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560
```

Cys Arg Ile Cys Ile
            565

<210> SEQ ID NO 23
<211> LENGTH: 1701
<212> TYPE: DNA
<213> ORGANISM: Artificial Sequence
<220> FEATURE:
<223> OTHER INFORMATION: pGX2016 H3HA-V2 DNA Sequence

<400> SEQUENCE: 23

```
atgaagacca tcattgccct gagctacatc ctgtgcctgg tgttcgccca gaagctgccc      60
ggcaacgaca cagcaccgc caccctgtgt ctgggccacc acgccgtgcc caacggcacc     120
ctggtgaaaa ccatcaccaa cgaccagatc gaagtgacca acgccaccga gctggtgcag    180
agcagcagca ccggcagaat ctgcgacagc ccccacagaa tcctggacgg cgagaactgc    240
accctgatcg acgccctgct gggcgatccc cactgcgacg gcttccagaa caaagaatgg    300
gacctgttcg tggaacggtc caaggccta c agcaactgct accccta cga cgtgcccga c   360
tacgccagcc tgagaagcct ggtggccagc agcggcacac tggaattcaa caacgagagc    420
ttcaactgga ccggcgtggc ccagaacggc accagcagcg cctgcaagcg gcggagcgtg    480
aagtccttct tctcccggct gaactggctg caccagctga gtacaagta ccccgccctg     540
aacgtgacca tgcccaacaa tgagaagttc gacaagctgt acatctgggg cgtgcaccac    600
cctagcaccg acagcgacca ccagcctg tacgcccagg ccagcggcag agtgaccgtg      660
tccaccaagc ggagccagca ccgtgatc cccaacatcg gcagcagacc ttgggtccgc      720
ggcgtgtcca gccggatcag catctactgg accatcgtga agcccggcga catcctgctg    780
atcaactcca ccggcaacct gatcgccccc agaggctact tcaagatcag aagcggcaag    840
agcagcatca tgagaagcga cgcccccatc ggcaagtgca cagcgagtg catcacccccc    900
aacggcagca tccccaacga caagcccttc cagaacgtga accggatcac ctacggcgcc    960
tgccccagat acgtgaagca gaacaccctg aagctggcca ccggcatgcg gaacgtgccc   1020
gagaagcaga cccggggcat ctttggcgcc attgccggct tcatcgagaa cggctgggag   1080
ggcatggtgg acgggtggta cggcttccgg caccagaata gcgagggcac aggccaggcc   1140
gccgacctga aaagcaccca ggccgccatc aaccagatca cggcaagct gaaccggctg    1200
atcgaaaaga ccaacgagaa gttccaccag atcgagaaag aattcagcga ggtggaaggc   1260
agaatccagg acctgaaaaa gtacgtggaa gataccaaga tcgacctgtg gtcctacaac   1320
gccgagctgc tggtggccct ggaaaaccag cacaccatcg acctgaccga ctccgagatg   1380
aacaagctgt tcgagcggac ccggaagcag ctgcgcgaga acgccgagga catgggcaac   1440
ggctgcttta gatctacca caagtgcgac aacgcctgca tcggctccat ccggaacggc    1500
acctacgacc acgacgtgta ccgggacgag gccctgaaca accggttcca gatcaagggc   1560
gtggaactga gtccggcta caaggactgg attctgtgga tcagcttcgc catcagctgc    1620
tttctgctgt gcgtggtgct gctgggcttc atcatgtggg cctgccagaa gggcaacatc   1680
cgctgcaaca tctgcatctg a                                             1701
```

<210> SEQ ID NO 24
<211> LENGTH: 566
<212> TYPE: PRT
<213> ORGANISM: Artificial Sequence
<220> FEATURE:
<223> OTHER INFORMATION: pGX2016 H3HA-V2 Protein Sequence

<400> SEQUENCE: 24

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
50                  55                  60

Gly Arg Ile Cys Asp Ser Pro His Arg Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
130                 135                 140

Gly Val Ala Gln Asn Gly Thr Ser Ser Ala Cys Lys Arg Arg Ser Val
145                 150                 155                 160

Lys Ser Phe Phe Ser Arg Leu Asn Trp Leu His Gln Leu Lys Tyr Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Ser Thr Asp Ser Asp Gln Thr
        195                 200                 205

Ser Leu Tyr Ala Gln Ala Ser Gly Arg Val Thr Val Ser Thr Lys Arg
210                 215                 220

Ser Gln Gln Thr Val Ile Pro Asn Ile Gly Ser Arg Pro Trp Val Arg
225                 230                 235                 240

Gly Val Ser Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asn Gln Ile Asn Gly Lys Leu Asn Arg Leu
385                 390                 395                 400

Ile Glu Lys Thr Asn Glu Lys Phe His Gln Ile Glu Lys Glu Phe Ser
                405                 410                 415
```

```
Glu Val Glu Gly Arg Ile Gln Asp Leu Glu Lys Tyr Val Glu Asp Thr
                420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
        450                 455                 460
Glu Arg Thr Arg Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
530                 535                 540
Val Val Leu Leu Gly Phe Ile Met Trp Ala Cys Gln Lys Gly Asn Ile
545                 550                 555                 560
Arg Cys Asn Ile Cys Ile
                565
```

<210> SEQ ID NO 25
<211> LENGTH: 1758
<212> TYPE: DNA
<213> ORGANISM: Artificial Sequence
<220> FEATURE:
<223> OTHER INFORMATION: pGX2014 B-HA-V2 DNA Sequence

<400> SEQUENCE: 25

```
atgaaggcca tcatcgtgct gctgatggtg gtgacaagca acgccgaccg gatctgcacc      60
ggcatcacca gcagcaacag cccccacgtg gtgaaaaccg ccacccaggg cgaagtgaac     120
gtgaccggcg tgatccccct gaccaccacc cccaccaaga gccacttcgc caacctgaag     180
ggcaccgaga cacggggcaa gctgtgtccc aagtgcctga actgcaccga cctggacgtg     240
gccctgggca gacccaagtg caccggcaac atccccagcg ccagagtgtc catcctgcac     300
gaagtgcggc ccgtgacctc cggctgcttc cctatcatgc acgaccggac caagatcaga     360
cagctgccta acctgctgcg gggctacgag cacatccggc tgagcaccca caacgtgatc     420
aacgccgaga cgcccctgg cggcccttac aagatcggca ccagcggaag ctgccccaac     480
gtgacaaacg gcaacggctt cttcgccacc atggcctggg ccgtgcccaa gacgacaac     540
aacaagacag ccaccaacag cctgaccatc gaggtgccct acatctgcac cgagggcgag     600
gaccagatca ccgtgtgggg cttccacagc gacaacgaga cacagatggc caagctgtac     660
ggcgacagca agcccagaa gttcaccagc tccgccaacg gcgtgaccac ccactacgtg     720
tcccagatcg gcggcttccc caaccagacc gaggatggcg gcctgcccca gagcggcaga     780
atcgtggtgg actacatggt gcagaagtcc ggcaagaccg gcaccatcac ctaccagcgg     840
ggcatcctgc tgccccagaa agtgtggtgc gccagcggcc ggtccaaagt gatcaaggga     900
agcctgcccc tgatcggcga ggccgattgc ctgcacgaga gtacggcgg cctgaacaag     960
agcaagccct actacaccgg cgagcacgcc aaggccatcg gcaactgccc catctgggtg    1020
aaaacccccc tgaagctggc caacggcacc aagtaccggc ctcccgccaa gctgctgaaa    1080
gagcggggct tcttcggcgc tatcgccggc tttctggaag cggctgggga gggcatgatc    1140
```

```
gccggctggc acggctacac atctcacggc gctcatggcg tggccgtggc cgccgatctg   1200
aagtccaccc aggaagccat caacaagatc accaagaacc tgaacagcct gagcgagctg   1260
gaagtgaaga acctgcagcg gctgagcggc gccatggacg agctgcacaa cgagatcctg   1320
gaactggacg agaaggtgga cgacctgcgg gccgacacca tctccagcca gatcgagctg   1380
gccgtgctgc tgtccaacga gggcatcatc aacagcgagg acgagcatct gctggccctg   1440
gaacggaagc tgaagaagat gctgggcccc tccgccgtgg aaatcggcaa tggctgcttc   1500
gagacaaagc acaagtgcaa ccagacctgc ctggaccgga tcgctgccgg caccttcgat   1560
gccggcgagt tcagcctgcc caccttcgac agcctgaaca tcaccgccgc cagcctgaac   1620
gacgacggcc tggacaacca caccatcctg ctgtactaca gcaccgccgc ctccagcctg   1680
gccgtgaccc tgatgatcgc catcttcgtg gtgtacatgg tgtccagaga caacgtgtcc   1740
tgcagcatct gcctgtga                                                 1758


<210> SEQ ID NO 26
<211> LENGTH: 585
<212> TYPE: PRT
<213> ORGANISM: Artificial Sequence
<220> FEATURE:
<223> OTHER INFORMATION: pGX2014 B-HA-V2 protein Sequence

<400> SEQUENCE: 26

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
        195                 200                 205

His Ser Asp Asn Glu Thr Gln Met Ala Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255
```

```
Gln Ser Gly Arg Ile Val Val Asp Tyr Met Val Gln Lys Ser Gly Lys
                260                 265                 270
Thr Gly Thr Ile Thr Tyr Gln Arg Gly Ile Leu Leu Pro Gln Lys Val
            275                 280                 285
Trp Cys Ala Ser Gly Arg Ser Lys Val Ile Lys Gly Ser Leu Pro Leu
290                 295                 300
Ile Gly Glu Ala Asp Cys Leu His Glu Lys Tyr Gly Gly Leu Asn Lys
305                 310                 315                 320
Ser Lys Pro Tyr Tyr Thr Gly Glu His Ala Lys Ala Ile Gly Asn Cys
                325                 330                 335
Pro Ile Trp Val Lys Thr Pro Leu Lys Leu Ala Asn Gly Thr Lys Tyr
                340                 345                 350
Arg Pro Pro Ala Lys Leu Leu Lys Glu Arg Gly Phe Phe Gly Ala Ile
            355                 360                 365
Ala Gly Phe Leu Glu Gly Gly Trp Glu Gly Met Ile Ala Gly Trp His
370                 375                 380
Gly Tyr Thr Ser His Gly Ala His Gly Val Ala Val Ala Ala Asp Leu
385                 390                 395                 400
Lys Ser Thr Gln Glu Ala Ile Asn Lys Ile Thr Lys Asn Leu Asn Ser
                405                 410                 415
Leu Ser Glu Leu Glu Val Lys Asn Leu Gln Arg Leu Ser Gly Ala Met
                420                 425                 430
Asp Glu Leu His Asn Glu Ile Leu Glu Leu Asp Glu Lys Val Asp Asp
            435                 440                 445
Leu Arg Ala Asp Thr Ile Ser Ser Gln Ile Glu Leu Ala Val Leu Leu
450                 455                 460
Ser Asn Glu Gly Ile Ile Asn Ser Glu Asp Glu His Leu Leu Ala Leu
465                 470                 475                 480
Glu Arg Lys Leu Lys Lys Met Leu Gly Pro Ser Ala Val Glu Ile Gly
                485                 490                 495
Asn Gly Cys Phe Glu Thr Lys His Lys Cys Asn Gln Thr Cys Leu Asp
                500                 505                 510
Arg Ile Ala Ala Gly Thr Phe Asp Ala Gly Glu Phe Ser Leu Pro Thr
            515                 520                 525
Phe Asp Ser Leu Asn Ile Thr Ala Ala Ser Leu Asn Asp Asp Gly Leu
530                 535                 540
Asp Asn His Thr Ile Leu Leu Tyr Tyr Ser Thr Ala Ala Ser Ser Leu
545                 550                 555                 560
Ala Val Thr Leu Met Ile Ala Ile Phe Val Val Tyr Met Val Ser Arg
                565                 570                 575
Asp Asn Val Ser Cys Ser Ile Cys Leu
                580                 585

<210> SEQ ID NO 27
<211> LENGTH: 1704
<212> TYPE: DNA
<213> ORGANISM: Artificial Sequence
<220> FEATURE:
<223> OTHER INFORMATION: H3HA-V3 DNA Sequence

<400> SEQUENCE: 27
atgaaaacaa tcatcgccct gtcctacatc ctgtgcctgg tctttgccca gaaactgccc        60
gggaacgaca actcaactgc tacactgtgt ctgggccacc atgccgtgcc taacgggacc       120
ctggtcaaga ccattacaaa cgaccagatc gaagtgacta atgctaccga actggtccag       180
```

```
agctcctcta ccggacgcat ttgcgacagc ccacaccgaa tcctggatgg caaaaattgt    240
acactgatcg acgcactgct gggagacccc cattgcgatg gcttccagaa caaggagtgg    300
gatctgtttg tggaacgcag taaagcttac tcaaattgtt accccttatga cgtgcctgat    360 tatgcatccc tgcgatctct ggtcgccagt tcagggactc tggagttcat caacgaagac    420
tttaattgga ccggagtggc tcaggatggc gggtcctacg catgcaagag aggcagtgtc    480
aactcattct ttagcaggct gaattggctg cacaagctgg agtacaaata tcccgccctg    540
aacgtgacta tgcctaacaa tgggaagttc gacaaactgt acatctgggg agtgcaccat    600
ccctccactg actctgatca gacctcactg tatgtccggg ccagcggcag agtgacagtc    660
agcactaagc ggtcccagca gacagtgatc cctaatattg gaagtaggcc atgggtccgc    720
ggcctgagct ccagaatctc aatctactgg acaatcgtga acctggcga tatcctgctg    780 attaacagca ctgggaatct gattgctcca agaggatatt tcaagattag gaccggcaaa    840
tctagtatca tgcggagcga cgcaccaatt ggcaactgct caagcgagtg tattactccc    900
aacgggtcca tcccaaatga taagcccttt cagaacgtga ataggatcac ctacggggcc    960
tgtccccgct atgtcaagca gaacacactg aaactggcta ctggaatgcg aaatgtgcct    1020
gagaaacaga cccggggcat cttcggggct attgcaggct ttatcgagaa cggatgggaa    1080
ggcatggtgg acgggtggta cggattcaga caccagaatt ccgagggaac cggacaggca    1140
gctgacctga agtctacaca ggcagccatc gatcagatta cggcaaact gaataggctg    1200 atcgagaaga caaacgaaaa attccatcag attgagaagg agttcagcga ggtggaaggg    1260
cgcatccagg atctggagaa gtacgtcgaa gacactaaaa ttgatctgtg gtcttataac    1320
gccgagctgc tggtggctct ggaaaatcag cacaccatcg acctgacaga tagtgagatg    1380
aataagctgt tcgaaaagac ccgaaaacag ctgcgggaga acgcagaaga catggggaat    1440
ggatgcttta agatctacca caaatgcgat aacgcctgta tcggctctat taggaatggg    1500
acatacgacc atgacgtgta ccgggacgag gccctgaaca atagatttca gatcaagggg    1560
gtggaactga gagcggata caaggattgg attctgtgga tctctttcgc cattagttgc    1620
tttctgctgt gcgtggtcct gctgggattc attatgtggg cttgtcagaa aggaaatatt    1680
cggtgtaaca tctgcatttg ataa    1704
```

<210> SEQ ID NO 28
<211> LENGTH: 566
<212> TYPE: PRT
<213> ORGANISM: Artificial Sequence
<220> FEATURE:
<223> OTHER INFORMATION: H3HA-V3 protein Sequence

<400> SEQUENCE: 28

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Arg Ile Leu Asp Gly Lys Asn Cys
65                  70                  75                  80

Thr Leu Ile Asp Ala Leu Leu Gly Asp Pro His Cys Asp Gly Phe Gln
```

-continued

```
                85                  90                  95
Asn Lys Glu Trp Asp Leu Phe Val Glu Arg Ser Lys Ala Tyr Ser Asn
            100                 105                 110
Cys Tyr Pro Tyr Asp Val Pro Asp Tyr Ala Ser Leu Arg Ser Leu Val
            115                 120                 125
Ala Ser Ser Gly Thr Leu Glu Phe Ile Asn Glu Asp Phe Asn Trp Thr
130                 135                 140
Gly Val Ala Gln Asp Gly Gly Ser Tyr Ala Cys Lys Arg Gly Ser Val
145                 150                 155                 160
Asn Ser Phe Phe Ser Arg Leu Asn Trp Leu His Lys Leu Glu Tyr Lys
            165                 170                 175
Tyr Pro Ala Leu Asn Val Thr Met Pro Asn Asn Gly Lys Phe Asp Lys
            180                 185                 190
Leu Tyr Ile Trp Gly Val His His Pro Ser Thr Asp Ser Asp Gln Thr
            195                 200                 205
Ser Leu Tyr Val Arg Ala Ser Gly Arg Val Thr Val Ser Thr Lys Arg
            210                 215                 220
Ser Gln Gln Thr Val Ile Pro Asn Ile Gly Ser Arg Pro Trp Val Arg
225                 230                 235                 240
Gly Leu Ser Ser Arg Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
            260                 265                 270
Tyr Phe Lys Ile Arg Thr Gly Lys Ser Ser Ile Met Arg Ser Asp Ala
            275                 280                 285
Pro Ile Gly Asn Cys Ser Ser Glu Cys Ile Thr Pro Asn Gly Ser Ile
290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
            325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
            355                 360                 365
Phe Arg His Gln Asn Ser Glu Gly Thr Gly Gln Ala Ala Asp Leu Lys
            370                 375                 380
Ser Thr Gln Ala Ala Ile Asp Gln Ile Asn Gly Lys Leu Asn Arg Leu
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
            450                 455                 460
Glu Lys Thr Arg Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
            485                 490                 495
Ile Arg Asn Gly Thr Tyr Asp His Asp Val Tyr Arg Asp Glu Ala Leu
            500                 505                 510
```

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
530                 535                 540

Val Val Leu Leu Gly Phe Ile Met Trp Ala Cys Gln Lys Gly Asn Ile
545                 550                 555                 560

Arg Cys Asn Ile Cys Ile
            565

<210> SEQ ID NO 29
<211> LENGTH: 1704
<212> TYPE: DNA
<213> ORGANISM: Artificial Sequence
<220> FEATURE:
<223> OTHER INFORMATION: H3HA-V4 DNA Sequence

<400> SEQUENCE: 29

| | | | |
|---|---|---|---|
| atgaaaacaa tcatcgccct gtcctacatc ctgtgcctgg tctttgctca gaaactgcct | 60 |
| ggaaatgaca actctactgc tacactgtgt ctgggacacc atgcagtgcc aaacggcacc | 120 |
| atcgtcaaaa ccattacaaa cgaccagatc gaagtgacta atgctaccga actggtccag | 180 |
| agctcctcta caggagagat tgcgacagc ccccaccaga tcctggatgg cgaaaattgt | 240 |
| actctgattg acgcactgct gggggaccct cagtgcgatg gattccagaa caagaaatgg | 300 |
| gatctgtttg tggagcggtc caaggcctac tctaattgtt accctatga cgtgcctgat | 360 |
| tatgcttcac tgagaagcct ggtcgcaagt tcaggcaccc tggagttcaa caatgaatcc | 420 |
| tttaactgga cagggtgac tcagaatgga acaagctccg cctgcatccg agatccaac | 480 |
| aattctttct ttagtcgcct gaactggctg acccatctga gttcaaata ccctgccctg | 540 |
| aatgtgacaa tgccaaacaa tgagcagttt gacaagctgt atatctgggg cgtccaccat | 600 |
| ccaggaaccg acaacgatca gatcttcctg tacgctcaag caagtggcag gattaccgtg | 660 |
| agtacaaaac gctcacagca gacagtcatc cctaacattg ggtcaaggcc acgcgtgcga | 720 |
| aatatcccct caagaatcag catctactgg actattgtca gccaggcga tatcctgctg | 780 |
| attaacagca ccgggaatct gatcgccccc agaggatact tcaagattag atctggcaaa | 840 |
| tctagtatca tgaggagtga cgctcccatt ggcaagtgca actcagagtg tattactcct | 900 |
| aacgggagca tcccaaatga taaaccctt cagaacgtga tagaatcac ctacggggca | 960 |
| tgtcctagat atgtcaagca gaacacactg aaactggcca ctggaatgcg caatgtgcca | 1020 |
| gagaagcaga cccgagggat cttcggagcc attgctggct ttatcgagaa cggctgggaa | 1080 |
| gggatggtgg acggatggta cggcttccgg caccagaatt ccgagggaat cggacaggca | 1140 |
| gctgacctga agtctacaca ggcagccatc gatcagatta cgggaaact gaataggctg | 1200 |
| atcggaaaga ctaacgaaaa gttccatcag atcgagaagg aattttccga ggtggaaggc | 1260 |
| cgcatccagg atctggagaa gtacgtcgaa gacaccaaaa ttgatctgtg gtcttataac | 1320 |
| gcagagctgc tggtggccct ggaaaatcag cacactatcg acctgaccga tagtgagatg | 1380 |
| aataagctgt tcgaaaagac taagaaacag ctgcgagaga cgctgaaga catgggaaat | 1440 |
| ggctgcttta gatctacca caatgcgat aacgcatgta tcggatctat tcggaatggc | 1500 |
| acatacgacc atgacgtgta ccgagacgag gccctgaaca tcggtttca gatcaagggc | 1560 |
| gtcgaactga gtccgggta caagattgg attctgtgga ttagcttcgc catttcctgc | 1620 |
| tttctgctgt gcgtggctct gctgggattc attatgtggg cctgtcagaa aggaaatatt | 1680 |

```
cggtgtaaca tttgcatctg ataa                                            1704
```

<210> SEQ ID NO 30
<211> LENGTH: 566
<212> TYPE: PRT
<213> ORGANISM: Artificial Sequence
<220> FEATURE:
<223> OTHER INFORMATION: H3HA-V4 protein Sequence

<400> SEQUENCE: 30

```
Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
```

```
                    355                 360                 365
Phe Arg His Gln Asn Ser Glu Gly Ile Gly Gln Ala Ala Asp Leu Lys
    370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
    450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
    530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 31
<211> LENGTH: 1755
<212> TYPE: DNA
<213> ORGANISM: Artificial Sequence
<220> FEATURE:
<223> OTHER INFORMATION: B-HA-V3 DNA Sequence

<400> SEQUENCE: 31
atgaaggcta ttattgtcct gctgatggtc gtcacatcta acgctgatcg catctgcacc      60
ggaattacct cctctaactc tcctcacgtg gtcaagacag ccactcaggg agaagtgaat     120
gtcaccggcg tgatccctct gaccacaact ccaacaaagt cccactttgc taacctgaag     180
gggaccaaaa caaggggaaa actgtgcccc aactgtctga attgcaccga cctggatgtg     240
gccctggggc gccctatgtg catcggaacc acaccatcag caaaagccag cattctgcac     300
gaggtgcgac ccgtcacttc tggctgcttc cctatcatgc atgaccggac caagattaga     360
cagctgccta atctgctgag ggggtacgaa acatccgcc tgtccactca taacgtgatt     420
aatgctgagc gagcaccagg cgggccatat cgactgggca cttccggatc ttgtcccaac     480
gtgaccagtc gctcaggctt ctttgccaca atggcttggg cagtccctcg agacaacaag     540
actgctacca tcccctgac agtggaagtc ccttacatct gcaccaaagg ggaggaccag     600
attacagtgt ggggatttca cagcgataac aagacacaga tgaaaaatct gtacgggat      660 tccaaccccc agaagttcac cagctccgcc aatggagtga ctacccatta tgtctcccag     720
atcggaggct tccaaaacca gaccgaggac ggggactgc acagtctgg ccgcatcgtg       780 gtcgattaca tggtgcagaa gcctggaaaa acaggcacta tcgtgtacca gcggggagtc     840
```

```
ctgctgccac agaaagtgtg gtgtgcttct ggcagaagta aggtcatcaa aggcagtctg    900
ccactgattg gggaagcaga ctgcctgcac gagaagtatg gcgggctgaa taagtccaaa    960
ccctactata ccggagaaca tgccaaagct atcggcaatt gtccaatttg ggtgaagact   1020
cccctgaaac tggcaaacgg caccaagtac agaccccctg ccaagctgct gaaagagagg   1080
gggttctttg gagcaatcgc cggctttctg gaaggaggct gggaggggat gattgccggc   1140
tggcacgggt atacatctca cggagcacat ggagtggctg tcgcagctga cctgaagagt   1200
acacaggaag ctatcaacaa gatcactaag aacctgaata gcctgtccga gctggaagtg   1260
aaaaatctgc agcgcctgag cggcgccatg gatgagctgc ataacagagat cctggaactg   1320 gacgagaagg tggacgatct gcgggctgat accatctcta gtcagattga actggcagtc   1380
ctgctgagta acgagggaat cattaattca gaggatgaac acctgctggc actgaaaga    1440 aagctgaaga aaatgctggg gcctagcgcc gtggacatcg ggaatggatg cttcgagact   1500
aagcataaat gtaaccagac ctgcctggat aggattgcag ccggcacctt caatgccggg   1560
gagttttccc tgccaacatt cgactctctg aacatcactg ctgcatcact gaatgacgat   1620
ggcctggata accacaccat tctgctgtac tatagcacag ccgcttcaag cctggccgtg   1680
acactgatga tcgctatttt catcgtgtat atggtgtcca gagataatgt ctcctgtagt   1740
atttgcctgt gataa                                                    1755
```

<210> SEQ ID NO 32
<211> LENGTH: 583
<212> TYPE: PRT
<213> ORGANISM: Artificial Sequence
<220> FEATURE:
<223> OTHER INFORMATION: B-HA-V3 protein Sequence

<400> SEQUENCE: 32

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Asn Cys Leu Asn Cys Thr Asp Leu Asp Val
65                  70                  75                  80

Ala Leu Gly Arg Pro Met Cys Ile Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr His Asn Val Ile Asn Ala Glu Arg
    130                 135                 140

Ala Pro Gly Gly Pro Tyr Arg Leu Gly Thr Ser Gly Ser Cys Pro Asn
145                 150                 155                 160

Val Thr Ser Arg Ser Gly Phe Phe Ala Thr Met Ala Trp Ala Val Pro
                165                 170                 175

Arg Asp Asn Lys Thr Ala Thr Asn Pro Leu Thr Val Glu Val Pro Tyr
            180                 185                 190

Ile Cys Thr Lys Gly Glu Asp Gln Ile Thr Val Trp Gly Phe His Ser
```

```
              195                 200                 205
Asp Asn Lys Thr Gln Met Lys Asn Leu Tyr Gly Asp Ser Asn Pro Gln
    210                 215                 220

Lys Phe Thr Ser Ser Ala Asn Gly Val Thr His Tyr Val Ser Gln
225                 230                 235                 240

Ile Gly Gly Phe Pro Asn Gln Thr Glu Asp Gly Gly Leu Pro Gln Ser
                245                 250                 255

Gly Arg Ile Val Val Asp Tyr Met Val Gln Lys Pro Gly Lys Thr Gly
            260                 265                 270

Thr Ile Val Tyr Gln Arg Gly Val Leu Leu Pro Gln Lys Val Trp Cys
        275                 280                 285

Ala Ser Gly Arg Ser Lys Val Ile Lys Gly Ser Leu Pro Leu Ile Gly
    290                 295                 300

Glu Ala Asp Cys Leu His Glu Lys Tyr Gly Gly Leu Asn Lys Ser Lys
305                 310                 315                 320

Pro Tyr Tyr Thr Gly Glu His Ala Lys Ala Ile Gly Asn Cys Pro Ile
                325                 330                 335

Trp Val Lys Thr Pro Leu Lys Leu Ala Asn Gly Thr Lys Tyr Arg Pro
            340                 345                 350

Pro Ala Lys Leu Leu Lys Glu Arg Gly Phe Phe Gly Ala Ile Ala Gly
        355                 360                 365

Phe Leu Glu Gly Gly Trp Glu Gly Met Ile Ala Gly Trp His Gly Tyr
    370                 375                 380

Thr Ser His Gly Ala His Gly Val Ala Val Ala Ala Asp Leu Lys Ser
385                 390                 395                 400

Thr Gln Glu Ala Ile Asn Lys Ile Thr Lys Asn Leu Asn Ser Leu Ser
                405                 410                 415

Glu Leu Glu Val Lys Asn Leu Gln Arg Leu Ser Gly Ala Met Asp Glu
            420                 425                 430

Leu His Asn Glu Ile Leu Glu Leu Asp Glu Lys Val Asp Asp Leu Arg
        435                 440                 445

Ala Asp Thr Ile Ser Ser Gln Ile Glu Leu Ala Val Leu Leu Ser Asn
    450                 455                 460

Glu Gly Ile Ile Asn Ser Glu Asp Glu His Leu Leu Ala Leu Glu Arg
465                 470                 475                 480

Lys Leu Lys Lys Met Leu Gly Pro Ser Ala Val Asp Ile Gly Asn Gly
                485                 490                 495

Cys Phe Glu Thr Lys His Lys Cys Asn Gln Thr Cys Leu Asp Arg Ile
            500                 505                 510

Ala Ala Gly Thr Phe Asn Ala Gly Glu Phe Ser Leu Pro Thr Phe Asp
        515                 520                 525

Ser Leu Asn Ile Thr Ala Ala Ser Leu Asn Asp Asp Gly Leu Asp Asn
    530                 535                 540

His Thr Ile Leu Leu Tyr Tyr Ser Thr Ala Ala Ser Ser Leu Ala Val
545                 550                 555                 560

Thr Leu Met Ile Ala Ile Phe Ile Val Tyr Met Val Ser Arg Asp Asn
                565                 570                 575

Val Ser Cys Ser Ile Cys Leu
            580

<210> SEQ ID NO 33
<211> LENGTH: 1761
<212> TYPE: DNA
<213> ORGANISM: Artificial Sequence
```

<220> FEATURE:
<223> OTHER INFORMATION: B-HA-V4 DNA Sequence

<400> SEQUENCE: 33

| | |

```
            20                  25                  30
Thr Ala Thr Gln Gly Glu Val Asn Val Thr Gly Val Ile Pro Leu Thr
            35                  40                  45
Thr Thr Pro Thr Lys Ser His Phe Ala Asn Leu Lys Gly Thr Lys Thr
    50                  55                  60
Arg Gly Lys Leu Cys Pro Lys Cys Leu Asn Cys Thr Asp Leu Asp Val
65                  70                  75                  80
Ala Leu Gly Arg Pro Lys Cys Thr Gly Asn Ile Pro Ser Ala Lys Val
                85                  90                  95
Ser Ile Leu His Glu Val Arg Pro Val Thr Ser Gly Cys Phe Pro Ile
                    100                 105                 110
Met His Asp Arg Thr Lys Ile Arg Gln Leu Pro Asn Leu Leu Arg Gly
                115                 120                 125
Tyr Glu His Ile Arg Leu Ser Thr His Asn Val Ile Asn Ala Glu Lys
                130                 135                 140
Ala Pro Gly Gly Pro Tyr Lys Ile Gly Thr Ser Gly Ser Cys Pro Asn
145                 150                 155                 160
Val Thr Asn Gly Asn Gly Phe Phe Ala Thr Met Ala Trp Ala Val Pro
                    165                 170                 175
Lys Asn Asp Asn Asn Lys Thr Ala Thr Asn Ser Leu Thr Ile Glu Val
                180                 185                 190
Pro Tyr Ile Cys Thr Glu Gly Glu Asp Gln Ile Thr Val Trp Gly Phe
                195                 200                 205
His Ser Asp Asn Glu Thr Gln Met Ala Lys Leu Tyr Gly Asp Ser Lys
                210                 215                 220
Pro Gln Lys Phe Thr Ser Ser Ala Asn Gly Val Thr Thr His Tyr Val
225                 230                 235                 240
Ser Gln Ile Gly Gly Phe Pro Asn Gln Thr Glu Asp Gly Gly Leu Pro
                    245                 250                 255
Gln Ser Gly Arg Ile Val Val Asp Tyr Met Val Gln Lys Ser Gly Lys
                260                 265                 270
Thr Gly Thr Ile Thr Tyr Gln Arg Gly Ile Leu Leu Pro Gln Lys Val
                275                 280                 285
Trp Cys Ala Ser Gly Arg Ser Lys Val Ile Lys Gly Ser Leu Pro Leu
                290                 295                 300
Ile Gly Glu Ala Asp Cys Leu His Glu Lys Tyr Gly Gly Leu Asn Lys
305                 310                 315                 320
Ser Lys Pro Tyr Tyr Thr Gly Glu His Ala Lys Ala Ile Gly Asn Cys
                    325                 330                 335
Pro Ile Trp Val Lys Thr Pro Leu Lys Leu Ala Asn Gly Thr Lys Tyr
                340                 345                 350
Arg Pro Pro Ala Lys Leu Leu Lys Glu Arg Gly Phe Phe Gly Ala Ile
                355                 360                 365
Ala Gly Phe Leu Glu Gly Gly Trp Glu Gly Met Ile Ala Gly Trp His
                370                 375                 380
Gly Tyr Thr Ser His Gly Ala His Gly Val Ala Val Ala Ala Asp Leu
385                 390                 395                 400
Lys Ser Thr Gln Glu Ala Ile Asn Lys Ile Thr Lys Asn Leu Asn Ser
                    405                 410                 415
Leu Ser Glu Leu Glu Val Lys Asn Leu Gln Arg Leu Ser Gly Ala Met
                420                 425                 430
Asp Glu Leu His Asn Glu Ile Leu Glu Leu Asp Glu Lys Val Asp Asp
                435                 440                 445
```

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asn Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 35
<211> LENGTH: 1728
<212> TYPE: DNA
<213> ORGANISM: Artificial Sequence
<220> FEATURE:
<223> OTHER INFORMATION: H1U consensus DNA sequence

<400> SEQUENCE: 35
ggtaccaagc ttgccaccat gaaggtgaaa ctgctggtgc tgctgtgcac cttcaccgcc      60
acctacgccg acaccatctg catcggctac acgccaacaa acagcaccga caccgtggat     120
accgtgctgg aaaagaacgt gaccgtgacc cacagcgtga acctgctgga agatagccac     180
aacggcaagc tgtgcctgct gaaaggcatc gcccccctgc agctgggcaa ctgcagcgtg     240
gccggctgga tcctgggcaa ccccgagtgc gagctgctga tttccaaaga agctggtcc      300 tacatcgtgg agaccccaa ccccgagaac ggcacctgct accccggcta cttcgccgac     360
tacgaggaac tgcgggagca gctgtccagc gtgagcagct cgagcggtt cgagatcttc     420 cccaaagaga gcagctggcc caaccacacc gtgaccggcg tgagcgccag ctgctcccac     480
aatggcaaga gcagcttcta ccggaacctg ctgtggctga ccggcaagaa cggcctgtac     540
cccaacctga gcaagagcta cgccaataac aaagaaaagg aagtgctggt gctgtggggc     600
gtgcaccacc ccccaacat cggcgaccag cgggccctgt accacaccga gaacgcctac     660
gtgagcgtgg tgtccagcca ctacagccgg cggttcaccc ccgagatcgc caagcggccc     720
aaagtgcggg accaggaagg ccggatcaac tactactgga ccctgctgga accggcgac      780 accatcatct cgaggccaa cggcaacctg atcgccccca gatacgcctt cgccctgagc     840
cggggcttcg gcagcggcat catcaccagc aacgccccca tggacgagtg cgacgccaag     900
tgccagaccc ctcagggagc tattaacagc agcctgccct ccagaacgt gcaccccgtg      960 accatcggcg agtgccccaa gtacgtgcgc agcgccaagc tgcggatggt gaccggcctg    1020
cggaacatcc ccagcatcca gagcagggc ctgttcggcg ccatcgccgg cttcatcgag    1080
ggcggctgga ccggcatggt ggacgggtgg tacggctacc accaccagaa cgagcagggc    1140
agcggctacg ccgccgacca aagagcacc cagaacgcca tcaacggcat caccaacaag    1200
gtgaacagcg tgatcgagaa gatgaacacc cagttcaccg ccgtgggcaa agagttcaac    1260

```
aagctggaac ggcggatgga aaacctgaac aagaaggtgg acgacggctt cctggacatc   1320
tggacctaca acgccgagct gctggtgctg ctggaaaacg agcggaccct ggacttccac   1380
gacagcaacg tgaagaacct gtacgagaag gtgaaaagcc agctgaagaa caacgccaaa   1440
gagatcggca acggctgctt cgagttctac cacaagtgca acgacgagtg catggaaagc   1500
gtgaagaatg caacctacga ctaccccaag tacagcgagg aaagcaagct gaaccgggag   1560
aagatcgacg gcgtgaagct ggaaagcatg ggcgtgtacc agatcctggc catctacagc   1620
accgtcgctt ccagcctcgt cctgctcgtg tccctgggcg ccatctcctt ttggatgtgc   1680
agcaacggca gcctgcagtg ccggatctgc atctgatgac tcgagctc                1728
```

```
<210> SEQ ID NO 36
<211> LENGTH: 565
<212> TYPE: PRT
<213> ORGANISM: Artificial Sequence
<220> FEATURE:
<223> OTHER INFORMATION: H1U consensus protein sequence

<400> SEQUENCE: 36
```

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Thr Ser Asn Ala Pro Met
```

|  |  |  |  |  | 275 |  |  |  | 280 |  |  |  |  | 285 |  |  |
|---|---|---|---|---|---|---|---|---|---|---|---|---|---|---|---|---|
| Asp | Glu | Cys | Asp | Ala | Lys | Cys | Gln | Thr | Pro | Gln | Gly | Ala | Ile | Asn | Ser |
|  |  |  |  |  | 290 |  |  |  | 295 |  |  |  |  | 300 |  |

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

```
<210> SEQ ID NO 37
<211> LENGTH: 1731
<212> TYPE: DNA
<213> ORGANISM: Artificial Sequence
<220> FEATURE:
<223> OTHER INFORMATION: H3HA1 consensus DNA sequence

<400> SEQUENCE: 37
```

| ggtaccaagc | ttgccaccat | gaaaaccatc | atcgccctga | gctacatcct | gtgcctggtg | 60 |
|---|---|---|---|---|---|---|
| ttcgcccaga | agctgcccgg | caacgacaac | agcaccgcca | ccctgtgtct | gggccaccac | 120 |
| gccgtgccca | acggcaccat | cgtgaaaaca | atcaccaacg | accagatcga | ggtgaccaac | 180 |
| gccaccgagc | tggtgcagag | cagcagcacc | ggcggcatct | gcgacagccc | ccaccagatc | 240 |
| ctggacggcg | agaactgcac | cctgatcgac | gccctgctgg | gcgaccctca | gtgcgacggc | 300 |
| ttccagaaca | aaaagtggga | cctgttcgtg | gagcggagca | aggcctacag | caactgctac | 360 |
| ccctacgacg | tgcccgacta | cgccagcctg | cggagcctgg | tggccagcag | cggcacactg | 420 |

-continued

```
gaattcaaca acgagagctt caactggacc ggcgtgaccc agaacggcac cagcagcgcc    480
tgcaagcggc ggagcaacaa cagcttcttt tccagactga actggctgac ccacctgaag    540
ttcaagtacc ccgccctgaa cgtgaccatg cccaacaatg agaagttcga caagctgtac    600
atctggggcg tgcaccaccc cggcaccgac aatgaccaga tcagcctgta cgcccaggcc    660
agcggccgga tcaccgtgag caccaagcgg agccagcaga ccgtgatccc caacatcggc    720
agccggccca gagtgagaga catccccagc cggatcagca tctactggac aatcgtgaag    780
cccggcgaca tcctgctgat caactccacc ggcaacctga tcgcccccag gggctacttc    840
aagatcagaa gcggcaagag cagcatcatg cggagcgacg cccccatcgg caagtgcaac    900
agcgagtgca tcacccccaa tggcagcatc cccaacgaca gcccttcca gaacgtgaac     960 cggatcacct acgcgcctg ccccagatac gtgaagcaga cacccctgaa gctggccacc    1020
ggcatgcgga acgtgcccga gaagcagacc cggggcatct tcggcgccat cgccggcttc    1080
atcgagaacg gctgggaggg catggtggac ggtggtacg gcttccggca ccagaactcc     1140
gagggcatcg ccaggccgc cgacctgaag agcacccagg ccgccatcaa ccagatcaac    1200
ggcaagctga accggctgat cggcaagacc aacgagaagt tccaccagat cgaaaaagaa    1260
ttcagcgagg tggagggccg gatccaggac ctggaaaagt acgtggagga caccaagatc    1320
gacctgtgga gctacaacgc cgagctgctg gtcgccctgg aaaaccagca caccatcgac    1380
ctgaccgaca gcgagatgaa caagctgttc gagcggacca gaagcagct gcgggagaac    1440 gccgaggaca tgggcaacgg ctgctttaag atctaccaca agtgcgacaa cgcctgcatc    1500
ggcagcatcc ggaacggcac ctacgaccac gacgtgtacc gggacgaggc cctgaacaac    1560
cggttccaga tcaagggcgt ggagctgaag agcggctaca aggactggat cctgtggatc    1620
agcttcgcca tcagctgctt tctgctgtgc gtggccctgc tgggattcat catgtgggcc    1680
tgccagaagg gcaacatccg ctgcaacatc tgcatctgat gactcgagct c             1731
```

<210> SEQ ID NO 38
<211> LENGTH: 566
<212> TYPE: PRT
<213> ORGANISM: Artificial Sequence
<220> FEATURE:
<223> OTHER INFORMATION: H3HA1 consensus protein sequence

<400> SEQUENCE: 38

```
Met Lys Thr Ile Ile Ala Leu Ser Tyr Ile Leu Cys Leu Val Phe Ala
1               5                  10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125
```

```
Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Ser Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asp Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
```

-continued 545 550 555 560

Arg Cys Asn Ile Cys Ile
565

<210> SEQ ID NO 39
<211> LENGTH: 1686
<212> TYPE: DNA
<213> ORGANISM: Artificial Sequence
<220> FEATURE:
<223> OTHER INFORMATION: DNA sequence of H7HA

<400> SEQUENCE: 39
atgaacactc agatcctggt cttcgcactg attgccatta ttccaacaaa tgctgacaaa 60
atctgcctgg gacatcatgc tgtgagcaac gggaccaaag tgaataccct gacagagcga 120
ggagtcgaag tggtcaacgc cactgagacc gtggaacgaa ctaatatccc ccggatttgc 180
agcaagggca aacggaccgt ggatctgggc cagtgtgggc tgctgggaac aatcactggg 240
ccccctcagt gcgatcagtt cctggagttt tccgccgacc tgatcattga gcggagagaa 300
ggatctgacg tgtgctaccc tggcaagttc gtcaacgagg aagctctgag gcagatcctg 360
cgagagagcg gcgggattga caaagaagca atgggcttca cctactccgg catcagaact 420
aatggagcca cctcagcttg caggcgcagc ggcagctcct tctatgccga gatgaagtgg 480
ctgctgtcca acacagacaa tgccgctttt ccccagatga ctaagtctta taaaaacacc 540
aggaaaagtc ctgcactgat cgtgtggggc attcaccatt ccgtctctac agccgaacag 600
actaagctgt acgggtctgg aaacaaactg gtgaccgtcg gatctagtaa ttatcagcag 660
agcttcgtgc catccccagg agcaaggcca caggtcaacg gactgagcgg gcgcatcgat 720
tttcactggc tgatgctgaa ccctaatgac accgtgacat tcagttttaa tggcgcattc 780
atcgccccag atagagcctc atttctgagg ggcaagtcca tggggattca gtctggagtg 840
caggtcgatg ctaactgcga gggcgactgt taccatagtg gaggcactat catttcaaac 900
ctgccattcc agaatatcga ctctcgcgca gtggggaagt gtccccgcta tgtcaaacag 960
cgaagtctgc tgctggccac aggaatgaag aatgtgcctg agatcccaaa aggcagaggg 1020
ctgttcggcg ctatcgcagg gtttattgag aacggatggg aaggcctgat tgatgggtgg 1080
tacggcttcc ggcaccagaa tgcccaggga gagggcacag cagccgatta taagagtact 1140
cagtcagcta tcgaccagat taccggcaag ctgaaccgcc tgatcgaaaa aacaaatcag 1200
cagttcgagc tgattgataa cgagttcaac gaggtggaaa agcagatcgg caacgtcatt 1260
aattggaccc gggacagcat cacagaagtg tggtcctaca acgctgagct gctggtcgca 1320
atggaaaatc agcataccat tgatctggca gacagcgaga tggataagct gtatgaacga 1380
gtgaaacggc agctgagaga gaacgctgag gaagacggga caggatgttt cgaaatcttt 1440
cacaagtgcg acgatgactg tatggcttca attcggaaca atacttacga ccatagcaaa 1500
tatcgggagg aagcaatgca gaatagaatc cagattgatc ctgtgaagct gtcaagcggc 1560
tacaaagacg tgatcctgtg gttctctttt ggggccagtt gcttcatcct gctggctatt 1620
gtcatgggac tggtgttcat ctgcgtcaaa aatggaaata tgcggtgtac tatctgtatc 1680
tgataa 1686

<210> SEQ ID NO 40
<211> LENGTH: 560
<212> TYPE: PRT
<213> ORGANISM: Artificial Sequence
<220> FEATURE:

<223> OTHER INFORMATION: Protein sequence of H7HA

<400> SEQUENCE: 40

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400
```

-continued

```
Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
        450                 455                 460

Leu Arg Glu Asn Ala Glu Asp Gly Thr Gly Cys Phe Glu Ile Phe
465                 470                 475                 480

His Lys Cys Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
        530                 535                 540

Val Phe Ile Cys Val Lys Asn Gly Asn Met Arg Cys Thr Ile Cys Ile
545                 550                 555                 560
```